US007871767B2

(12) United States Patent
Penger et al.

(10) Patent No.: US 7,871,767 B2

(45) Date of Patent: Jan. 18, 2011

(54) POLYMORPHISMS IN THE HUMAN GENE FOR CYTOCHROME P450 POLYPEPTIDE 2C8 AND THEIR USE IN DIAGNOSTIC APPLICATIONS

(75) Inventors: Anja Penger, Tutzing (DE); Reimund Sprenger, Weilheim (DE); Ulrich Brinkmann, Weilheim (DE)

(73) Assignee: PGxHealth, LLC, Newton, MA (US)

( * ) Notice: Subject to any disclaimer, the term of this patent is extended or adjusted under 35 U.S.C. 154(b) by 512 days.

(21) Appl. No.: 10/479,225

(22) PCT Filed: May 31, 2002

(86) PCT No.: PCT/EP02/06000

§ 371 (c)(1),
(2), (4) Date: Apr. 8, 2004

(87) PCT Pub. No.: WO02/099099

PCT Pub. Date: Dec. 12, 2002

(65) Prior Publication Data

US 2006/0172291 A1 Aug. 3, 2006

(30) Foreign Application Priority Data

Jun. 1, 2001 (EP) ................................. 01112899

(51) Int. Cl.

| | |
|---|---|
| ***C12Q 1/68*** | (2006.01) |
| ***C12Q 1/44*** | (2006.01) |
| ***C12P 19/34*** | (2006.01) |
| ***G01N 33/53*** | (2006.01) |
| ***C07H 21/04*** | (2006.01) |
| *C12N 9/00* | (2006.01) |

(52) U.S. Cl. ............................. 435/6; 435/7.1; 435/19; 435/91.2; 435/91.5; 435/91.52; 435/183; 536/23.2; 536/23.5; 536/25.32

(58) Field of Classification Search ....................... None
See application file for complete search history.

(56) References Cited

U.S. PATENT DOCUMENTS 5,403,708 A * 4/1995 Brennan et al. ................ 435/6

FOREIGN PATENT DOCUMENTS

WO WO 00/58508 A 10/2000
WO WO 02/08412 A 1/2002

OTHER PUBLICATIONS

Bahudar, N. et al. CYP2C8 polymorphisms in Caucasians and their relationship with paclitaxel 6alpha-hydroxylase activity in human liver microsomes. Biochemical Pharmacology 64:1579-1589 (Dec. 2002).*

(Continued)

*Primary Examiner*—Diana B Johannsen

(74) *Attorney, Agent, or Firm*—McCarter & English, LLP

(57) ABSTRACT

The present invention relates to a polymorphic CYP2C8-polynucleotide. Moreover, the invention relates to genes or vectors comprising the polynucleotides of the invention and to a host cell genetically engineered with the polynucleotide or gene of the invention. Further, the invention relates to methods for producing molecular variant polypeptides or fragments thereof, methods for producing cells capable of expressing a molecular variant polypeptide and to a polypeptide or fragment thereof encoded by the polynucleotide or the gene of the invention or which is obtainable by the method or from the cells produced by the method of the invention. Furthermore, the invention relates to an antibody which binds specifically the polypeptide of the invention. Moreover, the invention relates to a transgenic non-human animal. The invention also relates to a solid support comprising one or a plurality of the above mentioned polynucleotides, genes, vectors, polypeptides, antibodies or host cells. Furthermore, methods of identifying a polymorphism, identifying and obtaining a prodrug or drug or an inhibitor are also encompassed by the present invention. In addition, the invention relates to methods for producing of a pharmaceutical composition and to methods of diagnosing a disease. Further, the invention relates to a method of detection of the polynucleotide of the invention. Furthermore, comprised by the present invention are a diagnostic and a pharmaceutical composition. Even more, the invention relates to uses of the polynucleotides, genes, vectors, polypeptides or antibodies of the invention. Finally, the invention relates to a diagnostic kit.

4 Claims, 10 Drawing Sheets

OTHER PUBLICATIONS

Klose, T.S., Blaisdell, J.A. & Goldstein, J.A. Gene structure of CYP2C8 and extrahepatic distribution of the human CYP2Cs. J. Biochem Mol Toxicol 13, 289-95 (1999).
Gray, IC., Nobile, C., Muresu, R., Ford, S. & Spurr, N.K. A 2.4-megabase physical map spanning the CYP2C gene cluster on chromosome 10q24. Genomics 28, 328-32 (1995).
Goldstein, J.A. & de Morais, S.M. Biochemistry and molecular biology of the human CYP2C subfamily. Pharmacogenetics 4, 285-99 (1994).
Finta, C. & Zaphiropoulos, P.G. The human CYP2C locus: A prototype for intergenic and exon repetition splicing events [In Process Citation]. Genomics 63, 433-8 (2000).
Mechetner, E. et al. Levels of multidrug resistance (MDR1) P-glycoprotein expression by human breast correlate with in vitro resistance to taxol and doxorubicin. Clin Cancer Res 4, 389-98. (1998).
Tracy, T.S., Korzekwa, K.R., Gonzalez, F.J. & Wainer, I.W. Cytochrome P450 isoforms involved in metabolism of the enantiomers of verapamil and norverapamil. Br J Clin Pharmacol 47, 545-52. (1999).
Malinowski, J.M. & Bolesta, S. Rosiglitazone in the treatment of type 2 diabetes mellitus: a critical review. Clin Ther 22, 1151-68; discussion 1149-50. (2000).
Wrighton, S.A. et al. Purification of a human liver cytochrome P-450 immunochemically related to several cytochromes P-450 purified from untreated rats. J Clin Invest 80, 1017-22. (1987).
Relling, M.V., Aoyama, T., Gonzalez, F.J. & Meyer, U.A. Tolbutamide and mephenytoin hydroxylation by human cytochrome P450s in the CYP2C subfamily. J Pharmacol Exp Ther 252, 442-7. (1990).
Kerr, B.M. et al. Human liver carbamazepine metabolism. Role of CYP3A4 and CYP2C8 in 10,11-epoxide formation. Biochem Pharmacol 47, 1969-79 (1994).
Yun, C.H., Shimada, T. & Guengerich, F.P. Roles of human liver cytochrome P4502C and 3A enzymes in the 3-hydroxylation of benzo(a)pyrene. Cancer Res 52, 1868-74 (1992).
Leo, M.A., Kim, C.I. & Lieber, CS. NAD+-dependent retinol dehydrogenase in liver microsomes. Arch Biochem Biophys 259, 241-9. (1987).
Morel, F. et al. Expression of cytochrome P-450 enzymes in cultured human hepatocytes. Eur J Biochem 191, 437-44 (1990).
Thum, T. & Borlak, J. Cytochrome P450 mono-oxygenase gene expression and protein activity in cultures of adult cardiomyocytes of the rat. Br J Pharmacol 130, 1745-52. (2000).
Fisslthaler, B. et al. Cytochrome P450 2C is an EDHF synthase in coronary arteries. Nature 401, 493-7 (1999).
Fleming, I. et al. Endothelium-derived hyperpolarizing factor synthase (Cytochrome P450 2C9) is a functionally significant source of reactive oxygen species in coronary arteries. Circ Res 88, 44-51. (2001).
Meyer, U.A. & Zanger, U.M. Molecular mechanisms of genetic polymorphisms of drug metabolism, Annu Rev Pharmacol Toxicol 37, 270-96. (1997).
West, W.L., Knight, E.M., Pradhan, S. & Hinds, T.S. Interpatient variability: genetic predisposition and other genetic factors. J Clin Pharmocol 37, 635-48. (1997).
Marshall, A. Laying the foundations for personalized medicines. Nat Biotechnol 15, 954-7. (1997).
Marshall, A. Getting the right drug into the right patient. Nat Biotechnol 15, 1249-52 (1997).
Bertz, R.J. & Granneman, G.R. Use of in vitro and in vivo data to estimate the likelihood of metabolic pharmacokinetic interactions. Clin Phamacokinet 32, 210-58. (1997).
Engel, G., Hofmann, U. & Kroemer, H.K. Prediction of CYP2D6-mediated polymorphic drug metabolism (sparteine type) based on in vitro investigations. J Chromatogr B Biomed Appl 678, 93-103. (1996).
Olszewski, K.A., Kolinski, A. & Skolnick, J. Folding simulations and computer redesign of protein A three-helix bundle motifs. Proteins 25, 286-99. (1996).
Hoffman, D.L., Laiter, S., Singh, R.K., Vaisman, II & Tropsha, A. Rapid protein structure classification using one-dimensional structure profiles on the bioSCAN parallel computer. Comput Appl Biosci 11, 675-9. (1995).
Monge, A., Lathrop, E.J., Gunn, J.R., Shenkin, P.S. & Friesner, R.A. Computer modeling of protein folding: conformational and energetic analysis of reduced and detailed protein models. J Mol Biol 247, 995-1012. (1995).
Renouf, D.V. & Hounsell, E.F. Molecular modelling of glycoproteins by homology with non-glycosylated protein domains, computer simulated glycosylation and molecular dynamics. Adv Exp Med Biol 376, 37-45. (1995).
Fassina, G. & Melli, M. Identification of interactive sites of proteins and protein receptors by computer-assisted searches for complementary peptide sequences. Immunomethods 5, 114-20. (1994).
Berry, A, & Brenner, S.E. A prototype computer system for de novo protein design. Biochem Soc Trans 22, 1033-6. (1994).
Wodak, S.J. Computer-aided design in protein engineering. Ann NY Acad Sci 501, 1-13. (1987).
Pabo, C.O. & Suchanek, E.G. Computer-aided model-building strategies for protein design. Biochemistry 25, 5987-91. (1986).
Ostresh, J.M., Blondelle, S.E., Dorner, B. & Houghten, R.A. Generation and use of nonsupport-bound peptide and peptidomimetic combinatorial libraries. Methods Enzymol 267, 220-34. (1996).
Dorner, B., Husar, G.M., Ostresh, J.M. & Houghten, R.A. The synthesis of peptidomimetic combinatorial libraries through successive amide alkylations. Bioorg Med Chem 4, 709-15. (1996).
Rose, R.B., Craik, C.S., Douglas, N.L. & Stroud, R.M. Three-dimensional structures of HIV-1 and SIV protease product complexes. Biochemistry 35, 12933-44. (1996).
Rutenber, E.E. et al. A new class of HIV-1 protease inhibitor: the crystallographic structure, inhibition and chemical synthesis of an aminimide peptide isostere. Bioorg Med Chem 4, 1545-58. (1996).
Meyer, U.A. Overview of enzymes of drug metabolism. J Pharmacokinet Biopharm 24, 449-59. (1996).
Vallett, S.M., Sanchez, H.B., Rosenfeld, J.M. & Osborne, T.F. A direct role for sterol regulatory element binding protein in activation of 3-hydroxy-3-methylglutaryl coenzyme A reductase gene. J Biol Chem 271, 12247-53. (1996).
Dai et al., “Genetic polymorphisms of human CYP2C8 and their effects on metabolism of anticancer drug: Paclitaxel”, FASEB Journal, (May 11, 2000) vol. 14, No. 8, p. 162, Publisher: Federation Amer. Soc. Exp. Biol., Rockville, MD, XP009002862, ISSN: 0892-6638.
Dai, “Allelic frequencies of human CYP2C8 and genetic linkage among different ethnic populations”, FASEB Journal, vol. 15, No. 4, Mar. 7, 2001, p. A575, Annual Meeting of the Federation of American Societies for Experimental Biology on Experimental Biology 2001, XP009002845, ISSN: 0892-6638.
Dai, “Cardiovascular effects of polymorphic human CYP2C8s and the metabolism of arachidonic acid”, FASEB Journal, vol. 15, No. 5, Mar. 8, 2001, p. A918, Annual Meeting of the Federation of American Societies for Experimental Biology on Experimental Biology 2001, XP009002846, ISSN: 0892-6638.
Dai et al., “Polymorphisms in Human CYP2C8 Decrease metabolism of the Anticancer Drug Paclitaxel and Arachidonic Acid”, Pharmacogenetics, Chapman & Hall, London, GB, vol. 11, No. 7, Oct. 2001, pp. 597-607, XP009002859, ISSN: 0960-314X.
Soyama et al., “Non-synonymous Single Nucleotide Alterations Found in the CYP2C8 Gene Result in Reduced In Vitro Paclitaxel Metabolism”, Biological & Pharmaceutical Bulletin (of Japan), Pharmaceutical Society of Japan, vol. 24, No. 12, Dec. 2001, pp. 1427-1430, XP001121633, ISSN: 0918-6158.
Goldstein, “Clinical relevance of genetic polymorphisms in the human CYP2C subfamily”, British Journal of Clinical Pharmacology, vol. 52, No. 4, Oct. 2001, pp. 349-355, XP001121634, ISSN: 0306-5251.
Goldstein, J.A., Dai, D. Genetic polymorphisms of human CYP2C8 and their effects on metabolism of anticancer drug taxol. MDO 2000: 13th International Symposium on Microsomes and Drug Oxidations. Jul. 10-14, 2000, Stresa-Lago Maggiore, Italy. Abstract NIEHS, Research Triangle Park, North Caroline 27709.

* cited by examiner

Cyp2C8, positions G-1207A, -640/641delAT, G270A and A206G

AF136830.1 GI:6707879

```
catttttaatc cactggtgct agaattatta actaaattaa tgtttatttt gaaagtcact  61
gattagatta atccacaagt attgaatttt agtcaatctt ggtggcccgg tttaactgga  121
tgttttgctt aaaaggaagg cagcaagatg caggggttat ggtttccagc cccagcttgg  181
tcacttgcat tctgtgtgtc cttagctaaa gtactgaatc tccatggtct aactttctcc  241
tctctaaact gggaataatt ttacagtggg caaagataat tgagagaata aaaagagatg  301
tgatgagtgt gaaaattctc tgtaaatttg tcataatgtc tataaacata atcgataaaa  361
cattgtataa ctgggtctaa tattttctta atgaaagagc tggaaataac tgtactggtc  421
aatttagaat aaaggtaatc ttttcagagc atgcctttgt atacacactt tgttattagt  481
gatctagtaa tgttcataaa tccagttgta tttagatctt catgaccatt gactatcagt  541
tcccatttca ggtctgcaca ttgcagtggt tctgtgccct gggtccattc agtgatttcc  601
ctgtgttcca tcttctgttg aatccacaac tgttgttctg tgtataattt ctcttccttg  661
ctgtgtatga ttacattcta ttatttgtaa caataacaga ccaaaaacaa tagaagcagc  721
catgtctgga ggtgactgga aggtggagaa gccatagatt ttcaagccct gtgccataaa  781
ttatgtgaga ttggcccttt ccttaatagt gctgaacaac tttcacttgt gaggtgatgc  841
agaggggaga actctaattt ttatttcttc ttttgagcgt ctccggtcct cttatcctta  901
taaacaaata acggacttct atttaatgtg aagcctgttg ctttctgaac agagtcaagg  961
tggcgtatct tcagagtaac taatgtctgg ggtttgtttt gtttttctaa aattgttctt  1021
gagccagctg tggtgtaagt ggtaatgaac cccaatgggt atcagaagat ctctgctcaa  1081
atcccggttt taccggcaat gagctgtgtg gcactgacag gtgtcctgtt ctcccagagt  1141
ttctttccca atttgaaaaa taaaaaatga taatctttat actccagtct cttttaatga  1201
tgaatataca tttatatata tacttttata tatttaatat aatatttaat agtataaata  1261
tgtatttatg ttattattat gtaataatgt atgtaacact ccctgctaat tcagtttgtc  1321
tctttgacat gtaaagtaaa taatcaccta ttattataat aatgtaataa taacacaaat  1381
attattatgt aataacatat atatttatgt atattgttta tatacattta aatatatata  1441
aatatacatt tattagctaa taatttgata tatgtatggt aattcaacat gtatgagtta  1501
tattcactat ttcatgttta ggcagctgta ttttaagtga actatactaa atatttgaaa  1561
ggcttttgtt atcaagggct aagtctccta ttttttgata tagcattaca atgtacattt  1621
tttatacaca aaatatagaa tacactgatt tccctcaagg tcataaattc ccaactggtc  1681
attaatctga gaatattgaa ttttgagtat attctaacat agaatcattt acttcagtgt  1741
ttctccatca tcacagcaca ttggaacaac cagggacttt taattaaaaa tacctgggct  1801
ccaatccaat acaattaaac cagaatctcc tagattggca ctggaaagaa ggagtaggac  1861
aaaagaacat tttatttcta tccatgggcc aaagtccact cagaaaaaaa gtataaattg  1921
gatctaggtg attgtttact ttacatgtca aagagacaca cactaaatta gcagggagtg  1981
ttataaaaac tttggagtgc aagctcacag ctgtcttaat aagaagagaa ggcttcaatg  2041
gaaccttttg tggtcctggt gctgtgtctc tcttttatgc ttctcttttc actctgg
```

AF136831.1 GI:6707880

```
cagagctgta ggagaaggaa gctccctcct ggccccactc ctcttcctat tattggaaat  61
atgctacaga tagatgttaa ggacatctgc aaatctttca ccaatgtaag tctgccttat  121
gttcctccag ccaattgcaa agggtaagtt atttgactgc tatttttaga caaaatatat  181
tcctggaagc acactattat aatagatcat tgtaaagcaa aatactccct ctgaacttct  241
ttgatgtttc ttttgtcttc ctattttttt ttttttttga gacggagtct cgctctattg  301
cccaggctgg agtgcagtgg cactatctcc actcactgca agctctgcct cccaggttca  361
caccattctc ctgcctcagc ctcccccgag taactgggac tacaggtgcc ctccaccatg  421
cccggctaat tttttgtatg
```

AF136832.1 GI:6707881

```
agtttcttca tttttaaaac aggtcaaatg aatgtgctga atgtgttgaa gtgaggatga  61
actgtgtgat ttgtgtacca attgcctggg tcattgcgtg gcacatcaca ggccatctat  121
aagtggcagc tataacaatc accatcacat ttatgtacaa aattcagaaa tatcgaatct  181
atgtgtggca aatatgaaca ttaaaaaata caatgaaaat gtcagtctga atcatacata  241
gtatttggag caaatagcga cttattttgc tgctatttgc atttcctttc ccagttctca  301
aaagtctatg gtcctgtgtt caccgtgtat tttggcatga atcccatagt ggtgtttcat  361
ggatatgagg cagtgaagga agc
```

```
tactaaagga cttggtaggt gcacatattt ctgtgtcagc tttggtaact ggggtgaggg   61
ggatggaaaa cagagcccta aaaagcttct cagcagagct tagcctatct gcatggctgc   121
cgagtgttgc agcactttct tccttggctg tgaattctcc cagtttctgc cccttttttt   181
attaggaatc atttccagca atggaaagag atggaaggag atccggcgtt tctccctcac   241
aaccttgcgg aattttggga tggggaagag gagcattgag gaccgtgttc aagaggaagc   301
tcactgcctt gtggaggagt tgagaaaaac caagggtggg tgactctact ctgcgtcatt   361
gaccttaaca gttacctgtc ttcactagtg acgtccttgg aaacatttca ggggtggcca   421
ggtcttcatt gcgcatcctg gttgtcagcc ctcaggtggt gga
```

AF136834.2 GI:7544370

```
atgctcaact catatttaag gtaaaagtaa tgtgtttatt tcatccatgc tgattttttt   61
tggacacatg gggaatttgt aagatatgtt taaaatttct aaatttcctt tatgtcttaa   121
cagatgcaaa tcttttaaat atttattttt taataatttt tttaaaaatt tttaaatctt   181
tagcttcacc ctgtgatccc actttcatcc tgggctgtgc tccctgcaat gtgatctgct   241
ccg
```

AF136835.1 GI:6707884

```
tcaggattct gaactcccca tggatccagg taaggccaag attttatttt ccttggaaac   61
catttattca aggttgtagg gaagacttgg tttaaaaatg agaaaattga tactaaaatg   121
cttttataca ataaaaatga tgtatgagtg aagaaaataa ttaccacctt tgatttcctg   181
ttcaaaattt tcagcctcca atctttaggt acagaaaatt gctatatgtg cacaataaaa   241
atttccccat cagaagtgca aggggtcagg gaattccctt tcctagccaa gcaaagctgt   301
gaacagatgg cacctggaaa attgggtcac tcccacccta atactgtgct tttctagtgg   361
tcttagtaaa
```

AF136836.1 GI:6707885

```
tgggagatat acctaatgta tatgacgagt tattgggtgc agtacaccaa cctggcacat   61
gtatacatat gtgacaaacc tgcactttgt gcacatatac cctagaactt aaagtataat   121
aaaaaatgta tatatgtata aaaatttccc ttcaaaatgg acatgatgtc ttattcatat   181
ttatagttat aatttcaatc agggcttggt gtaagataca tatatcttat gacatgttta   241
tatttaatat tcttttctct tttaggtctg caataatttc cctctactca ttga
```

AF136837.1 GI:6707886

```
acaacaaagt gcttaaaaat gttgctctta cacgaagtta cattagggag aaagtaaaag   61
aacaccaagc atcactggat gttaacaatc ctcgggactt tatcgattgc ttcctgatca   121
aaatggagca ggtaagatat tagcaacaga tcagtatttt gatttcttgt ccattttgtg   181
attcatcgaa tccttctgta atttactaag gatgtttaaa tgatcaggcc agtaatgctt   241
gacaagcatc ttaattactt attgtattta tgggcctgca ctaaacatca tggaaaatac   301
aaaattgtcc aatggctaga atgcata
```

AF136838.1 GI:6707887

```
ataacacaaa ttgaagtaag acagggcatc ggtatacttc tgcttttatt tctggggaaa   61
gaaatattct gtgtgactaa cctaagcagc gaatgatttc atgaatggaa cttgtaggtc   121
tgtcaggaaa taaagtttga gtcaactgat ctgcagtttc tgccatacca cacagttgct   181
ttttctaata ctgtactgtc cagtatctct tttggctaac tttaaaaaat agtatgtttt   241
ttaaaattta gtgtatttag atatactggc acataatttg tcagataatt gcatgaaatc   301
acttctagga aaaggacaac caaaagtcag aattcaatat tgaaaa
```

AF136839.1 GI:6707888

```
tcctgctcct gctgaagcac ccagaggtca caggtaggac cacagatgat gaacaaagtg   61
aatttcagaa caatgctgag aagatggtgc cagtatcctc caccttgttt ctctcagaga   121
aggctcattc tttaaatttc tgtgtcatca gctgtaatct gtctaaattt gatgacacaa   181
tttaaaatga catctttgt
```

Fig. 7B

AF136840.1 GI:6707889
tatattatgg taattctttt tatatggctg gttgtacttc tggacatgta actcatgttt 61
gtaatgttgc tgggattttt atatcatgtt aatgtggcca tgaattgcta tgacaaatgt 121
tccatatatc ttcgtttcca tcagttcttt cttgtgtctt gtcagctaaa gtccaggaag 181
agattgatca tgtaattggc agacacagga gcccctgcat gcaggatagg agccacatgc 241
cttacac AF136841.1 GI:6707890
gccccatgca gtgaccactg atactaagtt cagaaactac ctcatcccca aggtaagctt 61
gtttctctta cactatattt ctgtacttct gaaatttcca tagtgctggt ttggttccaa 121
ccctctaaca acacaagatg agagaagtgc aaaactcata catgtggcag cttga AF136842.1 GI:6707891
ccaccactgg ccttaagctg atccatgtaa attactgtgt ctggctggac ctgagtttcc 61
tcatctatag atcaacgtta tggcgctacg tgatgtccac tacttctcct cacttctgga 121
cttctttata aatcagatta tctgttttgt tacttccagg gcacaaccat aatggcatta 181
ctgacttccg tgctacatga tgacaaagaa tttcctaatc caaata AF136843.1 GI:6707892
tttcctaatc caaatatctt tgaccctggc cactttctag ataagaatgg caactttaag 61
aaaagtgact acttcatgcc tttctcagca ggtaatagaa actcgtttcc atttgtattt 121
aaaggaaaga gagaactttt tggaattagt tggaatttac atggcacctc ctctggggct 181
ggtagaattg ctatttgtcc atgatcaaga gcaccactct taacacccat gtgctccacc 241
ctcacaatac accatcatta ttgggccaga tagcggggct tgcaggagtt aactctgttg AF136844.1 GI:67078933
aatatgtctc tttttgtaca tttgtttgtc ccaccatcca ttaatcaatc catcatgtca 61
tccatccatt catccacatg ttcattcatc tacccaatca ttaatcaatt atttactgca 121
tattctgttt gtgcaagtca caaatgactg tttgtcacag tcacagttaa acacaaggag 181
taactacttc ctttctttgt tatcttcagg aaaacgaatt tgtgcaggag aaggacttgc 241
ccgcatgg AF136845.1 GI:6707894
tctgcttcat ccctgtctga agaatgctag cccatctggc tgccgatctg ctatcacctg 61
caactctttt tttatcaagg acattcccac tattatgtct tctctgacct ctcatcaaat 121
cttcccattc actcaatatc ccataagcat ccaaactcca ttaaggagag ttgttcaggt 181
cactgcacaa atatatctgc aattattcat actctgtaac acttgtatta attgctgcat 241
atgctaatac ttttctaatg ctgacttttt aatatgttat cactgtaaaa cacagaaaag NM_000770.1 GI:4503220 mRNA
agtgcaagct cacagctgtc ttaataagaa gagaaggctt caatggaacc ttttgtggtc 61
ctggtgctgt gtctctcttt tatgcttctc ttttcactct ggagacagag ctgtaggaga 121
aggaagctcc ctcctggccc cactcctctt cctattattg gaaatatgct acagatagat 181
gttaaggaca tctgcaaatc tttcaccaat ttctcaaaag tctatggtcc tgtgttcacc 241
gtgtattttg gcatgaatcc catagtggtg tttcatggat atgaggcagt gaaggaagcc 301
ctgattgata atggagagga gttttctgga agaggcaatt ccccaatatc tcaaagaatt 361
actaaaggac ttggaatcat ttccagcaat ggaaagagat ggaaggagat ccggcgtttc 421
tccctcacaa ccttgcggaa ttttgggatg gggaagagga gcattgagga ccgtgttcaa 481
gaggaagctc actgccttgt ggaggagttg agaaaaacca aggcttcacc ctgtgatccc 541
actttcatcc tgggctgtgc tccctgcaat gtgatctgct ccgttgtttt ccagaaacga 601
tttgattata aagatcagaa ttttctcacc ctgatgaaaa gattcaatga aaacttcagg 661
attctgaact ccccatggat ccaggtctgc aataatttcc ctctactcat tgattgtttc 721
ccaggaactc acaacaaagt gcttaaaaat gttgctctta cacgaagtta cattagggag 781
aaagtaaaag aacaccaagc atcactggat gttaacaatc ctcgggactt tatcgattgc 841
ttcctgatca aaatggagca ggaaaaggac aaccaaaagt cagaattcaa tattgaaaac 901
ttggttggca ctgtagctga tctatttgtt gctggaacag agacaacaag caccactctg 961
agatatggac tcctgctcct gctgaagcac ccagaggtca cagctaaagt ccaggaagag 1021

Fig. 7C

```
attgatcatg taattggcag acacaggagc ccctgcatgc aggataggag ccacatgcct 1081
tacactgatg ctgtagtgca cgagatccag agatacagtg accttgtccc caccggtgtg 1141
ccccatgcag tgaccactga tactaagttc agaaactacc tcatccccaa gggcacaacc 1201
ataatggcat tactgacttc cgtgctacat gatgacaaag aatttcctaa tccaaatatc 1261
tttgaccctg gccactttct agataagaat ggcaacttta agaaaagtga ctacttcatg 1321
cctttctcag caggaaaacg aatttgtgca ggagaaggac ttgcccgcat ggagctattt 1381
ttatttctaa ccacaatttt acagaacttt aacctgaaat ctgttgatga tttaaagaac 1441
ctcaatacta ctgcagttac caaagggatt gtttctctgc caccctcata ccagatctgc 1501
ttcatccctg tctgaagaat gctagcccat ctggctgctg atctgctatc acctgcaact 1561
ctttttttat caaggacatt cccactatta tgtcttctct gacctctcat caaatcttcc 1621
cattcactca atatcccata agcatccaaa ctccattaag gagagttgtt caggtcactg 1681
cacaaatata tctgcaatta ttcatactct gtaacacttg tattaattgc tgcatatgct 1741
aatacttttc taatgctgac tttttaatat gttatcactg taaaacacag aaaagtgatt 1801
aatgaatgat aatttagatc catttctttt gtgaatgtgc taaataaaaa gtgttattaa 1861
ttgcta
```

NP_000761.2 GI:13787189

```
MEPFVVLVLC LSFMLLFSLW RQSCRRRKLP PGPTPLPIIG NMLQIDVKDI CKSFTNFSKV 61
YGPVFTVYFG MNPIVVFHGY EAVKEALIDN GEEFSGRGNS PISQRITKGL GIISSNGKRW 121
KEIRRFSLTN LRNFGMGKRS IEDRVQEEAH CLVEELRKTK ASPCDPTFIL GCAPCNVICS 181
VVFQKRFDYK DQNFLTLMKR FNENFRILNS PWIQVCNNFP LLIDCFPGTH NKVLKNVALT 241
RSYIREKVKE HQASLDVNNP RDFMDCFLIK MEQEKDNQKS EFNIENLVGT VADLFVAGTE 301
TTSTTLRYGL LLLLKHPEVT AKVQEEIDHV IGRHRSPCMQ DRSHMPYTDA VVHEIQRYSD 361
LVPTGVPHAV TTDTKFRNYL IPKGTTIMAL LTSVLHDDKE FPNPNIFDPG HFLDKNGNFK 421
KSDYFMPFSA GKRICAGEGL ARMELFLFLT TILQNFNLKS VDDLKNLNTT AVTKGIVSLP 481
PSYQICFIPV
```

Fig. 7D

SEQUENCE LISTING

<160> NUMBER OF SEQ ID NOS: 417

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Met Gly Lys Arg Ser Ile Glu
1 5

<210> SEQ ID NO 2
<211> LENGTH: 7
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 2

Met Gly Lys Lys Ser Ile Glu
1               5


<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Lys Thr Lys Ala Ser Pro
1               5


<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Lys Thr Lys Ala Ser Pro
1               5


<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ile Cys Ser Val Val Phe Gln
1               5


<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Cys Ser Ile Val Phe Gln
1               5


<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ile Leu Asn Ser Pro Trp
1               5
```

-continued

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

Ala Ile Leu Ser Ser Pro Trp
1 5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Arg Ser Tyr Ile Arg Glu Lys
1 5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Arg Ser Tyr Val Arg Glu Lys
1 5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Pro Arg Asp Phe Ile Asp Cys
1 5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Pro Arg Asp Leu Ile Asp Cys
1 5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

```
Arg Asp Phe Ile Asp Cys Phe
1               5


<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Asp Phe Met Asp Cys Phe
1               5


<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Cys Phe Leu Ile Lys Met Glu
1               5


<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Phe Leu Phe Lys Met Glu
1               5


<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Val Pro Thr Gly Val Pro His
1               5


<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Val Pro Thr Ser Val Pro His
1               5


<210> SEQ ID NO 19
<211> LENGTH: 7
<212> TYPE: PRT
<213> ORGANISM: Artificial Sequence
```

-continued

<220> FEATURE:
<223> OTHER INFORMATION: Description of Artificial Sequence: Synthetic
peptide

<400> SEQUENCE: 19

His Asp Asp Lys Glu Phe Pro
1 5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 20

His Asp Asp Arg Glu Phe Pro
1 5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 21

Phe Asp Pro Gly His Phe Leu
1 5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 22

Phe Asp Pro Gly His Phe Leu
1 5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Met Pro Phe Ser Ala Gly Lys
1 5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Met Pro Phe Ser Ala Gly Lys
1 5

-continued

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
attttagtca atcttggtgg cccg 24

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
ttcaacagaa gatggaacac aggga 25

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
tcatgaccat tgactatcag ttccc 25

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
tgatacccat tggggttcat tacc 24

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
aacagagtca aggtggcgta tcttc 25

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
caatattctc agattaatga ccagttggg 29

-continued

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
agacttagcc cttgataaca aaagcc 26

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
gtttaggcag ctgtatttta agtgaac 27

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
actccaaagt ttttataaca ctccc 25

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
ggcactggaa agaaggagta ggac 24

<210> SEQ ID NO 35
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
gatctattat aatagtgtgc ttccagg 27

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 36
ttgtgtacca attgcctggg tc 22

<210> SEQ ID NO 37

-continued

<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 37
tttttagggc tctgttttcc atcc 24

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 38
gagcttagcc tatctgcatg gctg 24

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
acctggccac ccctgaaatg 20

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
tccatgctga ttttttttgg acac 24

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 41
ctgacccctt gcacttctga tg 22

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
tgacgagtta ttgggtgcag tacac 25

<210> SEQ ID NO 43
<211> LENGTH: 23

-continued

<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
ttccatgatg tttagtgcag gcc 23

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
ttgaagtaag acagggcatc gg 22

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
agaaacaagg tggaggatac tggc 24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 46
ggccatgaat tgctatgaca aatg 24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 47
ggttggaacc aaaccagcac tatg 24

<210> SEQ ID NO 48
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 48
ctggctggac ctgagtttcc tc 22

<210> SEQ ID NO 49
<211> LENGTH: 20
<212> TYPE: DNA

-continued

```
<213> ORGANISM: Artificial Sequence
<220> FEATURE:
<223> OTHER INFORMATION: Description of Artificial Sequence: Synthetic
      primer

<400> SEQUENCE: 49

ttaactcctg caagccccgc                                                20


<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

gtacatttgt ttgtcccacc atcc                                           24


<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51

tgcagtgacc tgaacaactc tcct                                           24


<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52

gatgtgatga gtgtgaaaat                                                20


<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(11)
<223> OTHER INFORMATION: This region may or may not be present

<400> SEQUENCE: 53

gatgtgatga gtgtgaaaat                                                20


<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54

gatgtgatgt gtgaaaat                                                  18
```

-continued

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 55
attttcacac tcatcacatc 20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (10)..(11)
<223> OTHER INFORMATION: This region may or may not be present

<400> SEQUENCE: 56
attttcacac tcatcacatc 20

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 57 attttcaca catcacatc 18

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 58
ggaaataact gtactggtc 19

<210> SEQ ID NO 59
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 59
ggaaataacw gtactggtc 19

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 60

-continued ggaaataaca gtactggtc 19

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 61
gaccagtaca gttatttcc 19

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 62
gaccagtacw gttatttcc 19

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 63
gaccagtact gttatttcc 19

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 64
ggtctgcaca ttgcagtgg 19

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 65
ggtctgcacr ttgcagtgg 19

<210> SEQ ID NO 66
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 66
ggtctgcacg ttgcagtgg 19

-continued

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 67
ccactgcaat gtgcagacc 19

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 68
ccactgcaay gtgcagacc 19

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 69
ccactgcaac gtgcagacc 19

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 70
aaaacaatag aagcagcca 19

<210> SEQ ID NO 71
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 71
aaaacaatak aagcagcca 19

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 72
aaaacaatat aagcagcca 19

-continued

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 73
tggctgcttc tattgtttt 19

<210> SEQ ID NO 74
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 74
tggctgcttm tattgtttt 19

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 75
tggctgctta tattgtttt 19

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 76
agtgctgaac aactttcac 19

<210> SEQ ID NO 77
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 77
agtgctgaam aactttcac 19

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 78
agtgctgaaa aactttcac 19

-continued

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 79
gtgaaagttg ttcagcact 19

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 80
gtgaaagttk ttcagcact 19

<210> SEQ ID NO 81
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 81
gtgaaagttt ttcagcact 19

<210> SEQ ID NO 82
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 82
aacaactttc acttgtgag 19

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 83
aacaactttm acttgtgag 19

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 84
aacaacttta acttgtgag 19

<210> SEQ ID NO 85

-continued

<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 85
ctcacaagtg aaagttgtt 19

<210> SEQ ID NO 86
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 86
ctcacaagtk aaagttgtt 19

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 87
ctcacaagtt aaagttgtt 19

<210> SEQ ID NO 88
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 88
ttcacttgtg aggtgatgc 19

<210> SEQ ID NO 89
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 89
ttcacttgtr aggtgatgc 19

<210> SEQ ID NO 90
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
ttcacttgta aggtgatgc 19

<210> SEQ ID NO 91
<211> LENGTH: 19

-continued

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 91
gcatcacctc acaagtgaa 19

<210> SEQ ID NO 92
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 92
gcatcaccty acaagtgaa 19

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 93
gcatcacctt acaagtgaa 19

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 94
cttttgagcg tctccggtc 19

<210> SEQ ID NO 95
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 95
cttttgagcr tctccggtc 19

<210> SEQ ID NO 96
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 96
cttttgagca tctccggtc 19

<210> SEQ ID NO 97
<211> LENGTH: 19
<212> TYPE: DNA

-continued

<213> ORGANISM: Artificial Sequence
<220> FEATURE:
<223> OTHER INFORMATION: Description of Artificial Sequence: Synthetic
oligonucleotide

<400> SEQUENCE: 97
gaccggagac gctcaaaag 19

<210> SEQ ID NO 98
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 98
gaccggagay gctcaaaag 19

<210> SEQ ID NO 99
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 99
gaccggagat gctcaaaag 19

<210> SEQ ID NO 100
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 100
gcgtctccgg tcctcttat 19

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 101
gcgtctccgk tcctcttat 19

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 102
gcgtctccgt tcctcttat 19

<210> SEQ ID NO 103
<211> LENGTH: 19
<212> TYPE: DNA
<213> ORGANISM: Artificial Sequence -continued
<220> FEATURE:
<223> OTHER INFORMATION: Description of Artificial Sequence: Synthetic
oligonucleotide

<400> SEQUENCE: 103
ataagaggac cggagacgc 19

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 104
ataagaggam cggagacgc 19

<210> SEQ ID NO 105
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 105
ataagaggaa cggagacgc 19

<210> SEQ ID NO 106
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 106
accccaatgg gtatcagaa 19

<210> SEQ ID NO 107
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 107
accccaatgr gtatcagaa 19

<210> SEQ ID NO 108
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 108
accccaatga gtatcagaa 19

<210> SEQ ID NO 109
<211> LENGTH: 19
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 109
ttctgatacc cattggggt 19

<210> SEQ ID NO 110
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ttctgatacy cattggggt 19

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ttctgatact cattggggt 19

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gtatttatgt tattattatg t 21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)..(12)
<223> OTHER INFORMATION: This region may or may not be present

<400> SEQUENCE: 113
gtatttatgt tattattatg t 21

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
gtatttatgt tattatgt 18

<210> SEQ ID NO 115
<211> LENGTH: 21

-continued

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 115
acataataat aacataaata c 21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (10)..(12)
<223> OTHER INFORMATION: This region may or may not be present

<400> SEQUENCE: 116
acataataat aacataaata c 21

<210> SEQ ID NO 117
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 117
acataataac ataaatac 18

<210> SEQ ID NO 118
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 118
tgtaataaca tatatattta 20

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (10)..(11)
<223> OTHER INFORMATION: This region may or may not be present

<400> SEQUENCE: 119
tgtaataaca tatatattta 20

<210> SEQ ID NO 120
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide -continued

<400> SEQUENCE: 120
tgtaataaca tatattta 18

<210> SEQ ID NO 121
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 121
taaatatata tgttattaca 20

<210> SEQ ID NO 122
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (10)..(11)
<223> OTHER INFORMATION: This region may or may not be present

<400> SEQUENCE: 122
taaatatata tgttattaca 20

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 123
taaatatatg ttattaca 18

<210> SEQ ID NO 124
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 124
ttttttatat acaaaatat 19

<210> SEQ ID NO 125
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 125
ttttttatay acaaaatat 19

<210> SEQ ID NO 126
<211> LENGTH: 19
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 126 tttttatac acaaaatat 19

<210> SEQ ID NO 127
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
atattttgta tataaaaaa 19

<210> SEQ ID NO 128
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
atattttgtr tataaaaaa 19

<210> SEQ ID NO 129
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
atattttgtg tataaaaaa 19

<210> SEQ ID NO 130
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
ggtcataaat tcccaactg 19

<210> SEQ ID NO 131
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ggtcataaak tcccaactg 19

<210> SEQ ID NO 132
<211> LENGTH: 19
<212> TYPE: DNA
<213> ORGANISM: Artificial Sequence
<220> FEATURE:
<223> OTHER INFORMATION: Description of Artificial Sequence: Synthetic -continued

```
      oligonucleotide

<400> SEQUENCE: 132

ggtcataaag tcccaactg                                                19


<210> SEQ ID NO 133
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133

cagttgggaa tttatgacc                                                19


<210> SEQ ID NO 134
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134

cagttgggam tttatgacc                                                19


<210> SEQ ID NO 135
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135

cagttgggac tttatgacc                                                19


<210> SEQ ID NO 136
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136

acattggaac aaccaggga                                                19


<210> SEQ ID NO 137
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137

acattggaay aaccaggga                                                19


<210> SEQ ID NO 138
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 138
acattggaaa aaccaggga 19

<210> SEQ ID NO 139
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 139
tccctggttg ttccaatgt 19

<210> SEQ ID NO 140
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 140
tccctggttr ttccaatgt 19

<210> SEQ ID NO 141
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 141
tccctggttt ttccaatgt 19

<210> SEQ ID NO 142
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 142
aattaaaaat acctgggc 18

<210> SEQ ID NO 143
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (10)
<223> OTHER INFORMATION: This base may or may not be present

<400> SEQUENCE: 143
aattaaaaaa tacctgggc 19

<210> SEQ ID NO 144
<211> LENGTH: 19
<212> TYPE: DNA
<213> ORGANISM: Artificial Sequence -continued
<220> FEATURE:
<223> OTHER INFORMATION: Description of Artificial Sequence: Synthetic
oligonucleotide

<400> SEQUENCE: 144
aattaaaaaa tacctgggc 19

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 145
gcccaggtat ttttaatt 18

<210> SEQ ID NO 146
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (10)
<223> OTHER INFORMATION: This base may or may not be present

<400> SEQUENCE: 146
gcccaggtat tttttaatt 19

<210> SEQ ID NO 147
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 147
gcccaggtat tttttaatt 19

<210> SEQ ID NO 148
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 148
ctatccatgg gccaaagtc 19

<210> SEQ ID NO 149
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 149
ctatccatgr gccaaagtc 19

<210> SEQ ID NO 150

-continued

<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 150
ctatccatga gccaaagtc 19

<210> SEQ ID NO 151
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 151
gactttggcc catggatag 19

<210> SEQ ID NO 152
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 152
gactttggcy catggatag 19

<210> SEQ ID NO 153
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 153
gactttggct catggatag 19

<210> SEQ ID NO 154
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 154
ccactcagaa aaaaagtat 19

<210> SEQ ID NO 155
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 155
ccactcagam aaaaagtat 19

<210> SEQ ID NO 156
<211> LENGTH: 19

-continued

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 156
ccactcagac aaaaagtat 19

<210> SEQ ID NO 157
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 157
atactttttt tctgagtgg 19

<210> SEQ ID NO 158
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 158
atactttttk tctgagtgg 19

<210> SEQ ID NO 159
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 159
atactttttg tctgagtgg 19

<210> SEQ ID NO 160
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 160
acatgtcaaa gagacacac 19

<210> SEQ ID NO 161
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 161
acatgtcaam gagacacac 19

<210> SEQ ID NO 162
<211> LENGTH: 19
<212> TYPE: DNA

-continued

<213> ORGANISM: Artificial Sequence
<220> FEATURE:
<223> OTHER INFORMATION: Description of Artificial Sequence: Synthetic
oligonucleotide

<400> SEQUENCE: 162
acatgtcaac gagacacac 19

<210> SEQ ID NO 163
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 163
gtgtgtctct ttgacatgt 19

<210> SEQ ID NO 164
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 164
gtgtgtctck ttgacatgt 19

<210> SEQ ID NO 165
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 165
gtgtgtctcg ttgacatgt 19

<210> SEQ ID NO 166
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 166
attcagaaat atcgaatct 19

<210> SEQ ID NO 167
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 167
attcagaaay atcgaatct 19

<210> SEQ ID NO 168
<211> LENGTH: 19
<212> TYPE: DNA
<213> ORGANISM: Artificial Sequence -continued
<220> FEATURE:
<223> OTHER INFORMATION: Description of Artificial Sequence: Synthetic
      oligonucleotide

<400> SEQUENCE: 168
attcagaaac atcgaatct 19

<210> SEQ ID NO 169
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
agattcgata tttctgaat 19

<210> SEQ ID NO 170
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
agattcgatr tttctgaat 19

<210> SEQ ID NO 171
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
agattcgatg tttctgaat 19

<210> SEQ ID NO 172
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
agcaaatagc gacttattt 19

<210> SEQ ID NO 173
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
agcaaatagy gacttattt 19

<210> SEQ ID NO 174
<211> LENGTH: 19
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 174
agcaaatagt gacttattt                                                19

<210> SEQ ID NO 175
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
aaataagtcg ctatttgct                                                19

<210> SEQ ID NO 176
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
aaataagtcr ctatttgct                                                19

<210> SEQ ID NO 177
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
aaataagtca ctatttgct                                                19

<210> SEQ ID NO 178
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
atggctgccg agtgttgca                                                19

<210> SEQ ID NO 179
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
atggctgccr agtgttgca                                                19

<210> SEQ ID NO 180
<211> LENGTH: 19
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 180
atggctgcca agtgttgca 19

<210> SEQ ID NO 181
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 181
tgcaacactc ggcagccat 19

<210> SEQ ID NO 182
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 182
tgcaacacty ggcagccat 19

<210> SEQ ID NO 183
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 183
tgcaacactt ggcagccat 19

<210> SEQ ID NO 184
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 184
tccttggctg tgaattctc 19

<210> SEQ ID NO 185
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 185
tccttggctr tgaattctc 19

<210> SEQ ID NO 186
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide -continued

<400> SEQUENCE: 186
tccttggcta tgaattctc 19

<210> SEQ ID NO 187
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 187
gagaattcac agccaagga 19

<210> SEQ ID NO 188
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 188
gagaattcay agccaagga 19

<210> SEQ ID NO 189
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 189
gagaattcat agccaagga 19

<210> SEQ ID NO 190
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 190 cctttttta ttaggaat 18

<210> SEQ ID NO 191
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (10)
<223> OTHER INFORMATION: This base may or may not be present

<400> SEQUENCE: 191
cctttttttt attaggaat 19

<210> SEQ ID NO 192
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 192 ccttttttt attaggaat 19

<210> SEQ ID NO 193
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 193
attcctaata aaaaaagg 18

<210> SEQ ID NO 194
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (10)
<223> OTHER INFORMATION: This base may or may not be present

<400> SEQUENCE: 194
attcctaata aaaaaaagg 19

<210> SEQ ID NO 195
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 195
attcctaata aaaaaaagg 19

<210> SEQ ID NO 196
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 196 cttttttat taggaatca 19

<210> SEQ ID NO 197
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 197 cttttttay taggaatca 19

<210> SEQ ID NO 198

-continued

<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 198 cttttttac taggaatca 19

<210> SEQ ID NO 199
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 199
tgattcctaa taaaaaaag 19

<210> SEQ ID NO 200
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 200
tgattcctar taaaaaaag 19

<210> SEQ ID NO 201
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 201
tgattcctag taaaaaaag 19

<210> SEQ ID NO 202
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 202
tggggaagag gagcattga 19

<210> SEQ ID NO 203
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 203
tggggaagar gagcattga 19

<210> SEQ ID NO 204
<211> LENGTH: 19

-continued

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 204
tggggaagaa gagcattga 19

<210> SEQ ID NO 205
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 205
tcaatgctcc tcttcccca 19

<210> SEQ ID NO 206
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 206
tcaatgctcy tcttcccca 19

<210> SEQ ID NO 207
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 207
tcaatgctct tcttcccca 19

<210> SEQ ID NO 208
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 208
aaaaaccaag ggtgggtga 19

<210> SEQ ID NO 209
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 209
aaaaaccaar ggtgggtga 19

<210> SEQ ID NO 210
<211> LENGTH: 19
<212> TYPE: DNA

-continued

<213> ORGANISM: Artificial Sequence
<220> FEATURE:
<223> OTHER INFORMATION: Description of Artificial Sequence: Synthetic
oligonucleotide

<400> SEQUENCE: 210
aaaaaccaaa ggtgggtga 19

<210> SEQ ID NO 211
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 211
tcacccaccc ttggttttt 19

<210> SEQ ID NO 212
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 212
tcacccaccy ttggttttt 19

<210> SEQ ID NO 213
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 213
tcacccacct ttggttttt 19

<210> SEQ ID NO 214
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 214
cagttacctg tcttcacta 19

<210> SEQ ID NO 215
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 215
cagttaccts tcttcacta 19

<210> SEQ ID NO 216
<211> LENGTH: 19
<212> TYPE: DNA
<213> ORGANISM: Artificial Sequence -continued
<220> FEATURE:
<223> OTHER INFORMATION: Description of Artificial Sequence: Synthetic
      oligonucleotide

<400> SEQUENCE: 216
cagttacctc tcttcacta 19

<210> SEQ ID NO 217
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
tagtgaagac aggtaactg 19

<210> SEQ ID NO 218
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 218
tagtgaagas aggtaactg 19

<210> SEQ ID NO 219
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
tagtgaagag aggtaactg 19

<210> SEQ ID NO 220
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
tgtaagatat gtttaaaat 19

<210> SEQ ID NO 221
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: This base may or may not be present

<400> SEQUENCE: 221
tgtaagatat gtttaaaat 19

<210> SEQ ID NO 222

-continued

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222

tgtaagatag tttaaaat                                                18


<210> SEQ ID NO 223
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223

attttaaaca tatcttaca                                               19


<210> SEQ ID NO 224
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: This base may or may not be present

<400> SEQUENCE: 224

attttaaaca tatcttaca                                               19


<210> SEQ ID NO 225
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225

attttaaact atcttaca                                                18


<210> SEQ ID NO 226
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226

ataatttttt taaaaattt                                               19


<210> SEQ ID NO 227
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 227

ataattttw taaaaattt                                                19
```

-continued

<210> SEQ ID NO 228
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 228
ataattttta taaaaattt 19

<210> SEQ ID NO 229
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 229
aaatttttaa aaaaattat 19

<210> SEQ ID NO 230
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 230
aaatttttaw aaaaattat 19

<210> SEQ ID NO 231
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 231
aaatttttat aaaaattat 19

<210> SEQ ID NO 232
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 232
taattttttt aaaaatttt 19

<210> SEQ ID NO 233
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 233
taattttttw aaaaatttt 19

-continued

<210> SEQ ID NO 234
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 234
taatttttta aaaaatttt 19

<210> SEQ ID NO 235
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 235
aaaattttta aaaaaatta 19

<210> SEQ ID NO 236
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 236 aaaattttw aaaaaatta 19

<210> SEQ ID NO 237
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 237 aaaattttt aaaaaatta 19

<210> SEQ ID NO 238
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 238
atctgctccg ttgttttcc 19

<210> SEQ ID NO 239
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 239
atctgctccr ttgttttcc 19

-continued

<210> SEQ ID NO 240
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 240
atctgctcca ttgttttcc 19

<210> SEQ ID NO 241
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 241
ggaaaacaac ggagcagat 19

<210> SEQ ID NO 242
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 242
ggaaaacaay ggagcagat 19

<210> SEQ ID NO 243
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 243
ggaaaacaat ggagcagat 19

<210> SEQ ID NO 244
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 244
ggattctgaa ctccccatg 19

<210> SEQ ID NO 245
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 245
ggattctgar ctccccatg 19

<210> SEQ ID NO 246

-continued

<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 246
ggattctgag ctccccatg 19

<210> SEQ ID NO 247
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 247
catggggagt tcagaatcc 19

<210> SEQ ID NO 248
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 248
catggggagy tcagaatcc 19

<210> SEQ ID NO 249
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 249
catggggagc tcagaatcc 19

<210> SEQ ID NO 250
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 250
tgatttcctg ttcaaaatt 19

<210> SEQ ID NO 251
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 251
tgatttcctr ttcaaaatt 19

<210> SEQ ID NO 252
<211> LENGTH: 19

-continued

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 252
tgatttccta ttcaaaatt 19

<210> SEQ ID NO 253
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 253
aattttgaac aggaaatca 19

<210> SEQ ID NO 254
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 254
aattttgaay aggaaatca 19

<210> SEQ ID NO 255
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 255
aattttgaat aggaaatca 19

<210> SEQ ID NO 256
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 256
acttaaagta taataaaaa 19

<210> SEQ ID NO 257
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 257
acttaaagtr taataaaaa 19

<210> SEQ ID NO 258
<211> LENGTH: 19
<212> TYPE: DNA

-continued

<213> ORGANISM: Artificial Sequence
<220> FEATURE:
<223> OTHER INFORMATION: Description of Artificial Sequence: Synthetic
      oligonucleotide

<400> SEQUENCE: 258
acttaaagtg taataaaaa 19

<210> SEQ ID NO 259
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 259
tttttattat actttaagt 19

<210> SEQ ID NO 260
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 260
tttttattay actttaagt 19

<210> SEQ ID NO 261
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 261
tttttattac actttaagt 19

<210> SEQ ID NO 262
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 262
aaaatgtata tatgtataa 19

<210> SEQ ID NO 263
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 263
aaaatgtatr tatgtataa 19

<210> SEQ ID NO 264
<211> LENGTH: 19
<212> TYPE: DNA
<213> ORGANISM: Artificial Sequence -continued
<220> FEATURE:
<223> OTHER INFORMATION: Description of Artificial Sequence: Synthetic
      oligonucleotide

<400> SEQUENCE: 264
aaaatgtatg tatgtataa 19

<210> SEQ ID NO 265
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 265
ttatacatat atacatttt 19

<210> SEQ ID NO 266
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 266
ttatacatay atacatttt 19

<210> SEQ ID NO 267
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 267
ttatacatac atacatttt 19

<210> SEQ ID NO 268
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 268
atgatgtctt attcatatt 19

<210> SEQ ID NO 269
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 269
atgatgtcty attcatatt 19

<210> SEQ ID NO 270
<211> LENGTH: 19
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 270
atgatgtctc attcatatt 19

<210> SEQ ID NO 271
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 271
aatatgaata agacatcat 19

<210> SEQ ID NO 272
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 272
aatatgaatr agacatcat 19

<210> SEQ ID NO 273
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 273
aatatgaatg agacatcat 19

<210> SEQ ID NO 274
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 274
tttatagtta taatttcaa 19

<210> SEQ ID NO 275
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 275
tttatagttr taatttcaa 19

<210> SEQ ID NO 276
<211> LENGTH: 19
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 276
tttatagttg taatttcaa 19

<210> SEQ ID NO 277
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 277
ttgaaattat aactataaa 19

<210> SEQ ID NO 278
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 278
ttgaaattay aactataaa 19

<210> SEQ ID NO 279
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 279
ttgaaattac aactataaa 19

<210> SEQ ID NO 280
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 280
cgaagttaca ttagggaga 19

<210> SEQ ID NO 281
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 281
cgaagttacr ttagggaga 19

<210> SEQ ID NO 282
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide -continued

<400> SEQUENCE: 282
cgaagttacg ttagggaga 19

<210> SEQ ID NO 283
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 283
tctccctaat gtaacttcg 19

<210> SEQ ID NO 284
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 284
tctccctaay gtaacttcg 19

<210> SEQ ID NO 285
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 285
tctccctaac gtaacttcg 19

<210> SEQ ID NO 286
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 286
tcgggacttt atcgattgc 19

<210> SEQ ID NO 287
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 287
tcgggacttk atcgattgc 19

<210> SEQ ID NO 288
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide -continued

<400> SEQUENCE: 288
tcgggacttg atcgattgc 19

<210> SEQ ID NO 289
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 289
gcaatcgata aagtcccga 19

<210> SEQ ID NO 290
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 290
gcaatcgatm aagtcccga 19

<210> SEQ ID NO 291
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 291
gcaatcgatc aagtcccga 19

<210> SEQ ID NO 292
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 292
ggactttatc gattgcttc 19

<210> SEQ ID NO 293
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 293
ggactttats gattgcttc 19

<210> SEQ ID NO 294
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 294

-continued ggactttatg gattgcttc 19

<210> SEQ ID NO 295
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 295
gaagcaatcg ataaagtcc 19

<210> SEQ ID NO 296
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 296
gaagcaatcs ataaagtcc 19

<210> SEQ ID NO 297
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 297
gaagcaatcc ataaagtcc 19

<210> SEQ ID NO 298
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 298
tgcttcctga tcaaaatgg 19

<210> SEQ ID NO 299
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 299
tgcttcctgw tcaaaatgg 19

<210> SEQ ID NO 300
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 300

-continued

```
tgcttcctgt tcaaaatgg                                                19


<210> SEQ ID NO 301
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 301

ccattttgat caggaagca                                                19


<210> SEQ ID NO 302
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 302

ccattttgaw caggaagca                                                19


<210> SEQ ID NO 303
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 303

ccattttgaa caggaagca                                                19


<210> SEQ ID NO 304
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 304

gtccccaccg gtgtgcccc                                                19


<210> SEQ ID NO 305
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 305

gtccccaccr gtgtgcccc                                                19


<210> SEQ ID NO 306
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306

gtccccacca gtgtgcccc                                                19
```

-continued

<210> SEQ ID NO 307
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 307
ggggcacacc ggtggggac 19

<210> SEQ ID NO 308
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 308
ggggcacacy ggtggggac 19

<210> SEQ ID NO 309
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 309
ggggcacact ggtggggac 19

<210> SEQ ID NO 310
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 310
atgatgacaa agaatttcc 19

<210> SEQ ID NO 311
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 311
atgatgacar agaatttcc 19

<210> SEQ ID NO 312
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 312
atgatgacag agaatttcc 19

-continued

<210> SEQ ID NO 313
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 313
ggaaattctt tgtcatcat 19

<210> SEQ ID NO 314
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 314
ggaaattcty tgtcatcat 19

<210> SEQ ID NO 315
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 315
ggaaattctc tgtcatcat 19

<210> SEQ ID NO 316
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 316
tgaccctggc cactttcta 19

<210> SEQ ID NO 317
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 317
tgaccctggy cactttcta 19

<210> SEQ ID NO 318
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 318
tgaccctggt cactttcta 19

-continued

<210> SEQ ID NO 319
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 319
tagaaagtgg ccagggtca 19

<210> SEQ ID NO 320
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 320
tagaaagtgr ccagggtca 19

<210> SEQ ID NO 321
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 321
tagaaagtga ccagggtca 19

<210> SEQ ID NO 322
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 322
gcctttctca gcaggtaat 19

<210> SEQ ID NO 323
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 323
gcctttctcr gcaggtaat 19

<210> SEQ ID NO 324
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 324
gcctttctcg gcaggtaat 19

<210> SEQ ID NO 325

-continued

<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 325
attacctgct gagaaaggc 19

<210> SEQ ID NO 326
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 326
attacctgcy gagaaaggc 19

<210> SEQ ID NO 327
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 327
attacctgcc gagaaaggc 19

<210> SEQ ID NO 328
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 328
tacatggcac ctcctctgg 19

<210> SEQ ID NO 329
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 329
tacatggcam ctcctctgg 19

<210> SEQ ID NO 330
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 330
tacatggcaa ctcctctgg 19

<210> SEQ ID NO 331
<211> LENGTH: 19

-continued

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 331
ccagaggagg tgccatgta 19

<210> SEQ ID NO 332
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 332
ccagaggagk tgccatgta 19

<210> SEQ ID NO 333
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 333
ccagaggagt tgccatgta 19

<210> SEQ ID NO 334
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 334
ttgctatttg tccatgatc 19

<210> SEQ ID NO 335
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 335
ttgctatttr tccatgatc 19

<210> SEQ ID NO 336
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 336
ttgctattta tccatgatc 19

<210> SEQ ID NO 337
<211> LENGTH: 19
<212> TYPE: DNA

-continued

<213> ORGANISM: Artificial Sequence
<220> FEATURE:
<223> OTHER INFORMATION: Description of Artificial Sequence: Synthetic
      oligonucleotide

<400> SEQUENCE: 337
gatcatggac aaatagcaa 19

<210> SEQ ID NO 338
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 338
gatcatggay aaatagcaa 19

<210> SEQ ID NO 339
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 339
gatcatggat aaatagcaa 19

<210> SEQ ID NO 340
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 340
gatcaagagc accactctt 19

<210> SEQ ID NO 341
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 341
gatcaagagy accactctt 19

<210> SEQ ID NO 342
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
gatcaagagt accactctt 19

<210> SEQ ID NO 343
<211> LENGTH: 19
<212> TYPE: DNA
<213> ORGANISM: Artificial Sequence -continued
<220> FEATURE:
<223> OTHER INFORMATION: Description of Artificial Sequence: Synthetic
oligonucleotide

<400> SEQUENCE: 343
aagagtggtg ctcttgatc 19

<210> SEQ ID NO 344
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 344
aagagtggtr ctcttgatc 19

<210> SEQ ID NO 345
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 345
aagagtggta ctcttgatc 19

<210> SEQ ID NO 346
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 346
caccactctt aacacccat 19

<210> SEQ ID NO 347
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 347
caccactcty aacacccat 19

<210> SEQ ID NO 348
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 348
caccactctc aacacccat 19

<210> SEQ ID NO 349
<211> LENGTH: 19
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 349
atgggtgtta agagtggtg 19

<210> SEQ ID NO 350
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 350
atgggtgttr agagtggtg 19

<210> SEQ ID NO 351
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 351
atgggtgttg agagtggtg 19

<210> SEQ ID NO 352
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 352
aatacaccat cattattgg 19

<210> SEQ ID NO 353
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 353
aatacaccay cattattgg 19

<210> SEQ ID NO 354
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 354
aatacaccac cattattgg 19

<210> SEQ ID NO 355
<211> LENGTH: 19
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 355
ccaataatga tggtgtatt 19

<210> SEQ ID NO 356
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 356
ccaataatgr tggtgtatt 19

<210> SEQ ID NO 357
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 357
ccaataatgg tggtgtatt 19

<210> SEQ ID NO 358
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 358
tgggccagat agcggggct 19

<210> SEQ ID NO 359
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 359
tgggccagay agcggggct 19

<210> SEQ ID NO 360
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 360
tgggccagac agcggggct 19

<210> SEQ ID NO 361
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide -continued

<400> SEQUENCE: 361
agccccgcta tctggccca 19

<210> SEQ ID NO 362
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 362
agccccgctr tctggccca 19

<210> SEQ ID NO 363
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 363
agccccgctg tctggccca 19

<210> SEQ ID NO 364
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 364
ttatttactg catattctg 19

<210> SEQ ID NO 365
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 365
ttatttactr catattctg 19

<210> SEQ ID NO 366
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 366
ttatttacta catattctg 19

<210> SEQ ID NO 367
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide -continued

<400> SEQUENCE: 367
cagaatatgc agtaaataa 19

<210> SEQ ID NO 368
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 368
cagaatatgy agtaaataa 19

<210> SEQ ID NO 369
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 369
cagaatatgt agtaaataa 19

<210> SEQ ID NO 370
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 370
tctggctgcc gatctgcta 19

<210> SEQ ID NO 371
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 371
tctggctgcy gatctgcta 19

<210> SEQ ID NO 372
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 372
tctggctgct gatctgcta 19

<210> SEQ ID NO 373
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 373

-continued tagcagatcg gcagccaga 19

<210> SEQ ID NO 374
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 374
tagcagatcr gcagccaga 19

<210> SEQ ID NO 375
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 375
tagcagatca gcagccaga 19

<210> SEQ ID NO 376
<211> LENGTH: 7
<212> TYPE: PRT
<213> ORGANISM: Homo sapiens

<400> SEQUENCE: 376

Glu Leu Arg Lys Thr Lys Ala
1 5

<210> SEQ ID NO 377
<211> LENGTH: 7
<212> TYPE: PRT
<213> ORGANISM: Homo sapiens

<400> SEQUENCE: 377

Glu Leu Arg Lys Pro Arg Leu
1 5

<210> SEQ ID NO 378
<211> LENGTH: 7
<212> TYPE: PRT
<213> ORGANISM: Homo sapiens

<400> SEQUENCE: 378

Met Glu Gln Glu Lys Asp Asn
1 5

<210> SEQ ID NO 379
<211> LENGTH: 3
<212> TYPE: PRT
<213> ORGANISM: Homo sapiens

<400> SEQUENCE: 379

Met Glu Gln
1

<210> SEQ ID NO 380
<211> LENGTH: 7
<212> TYPE: PRT
<213> ORGANISM: Homo sapiens -continued

<400> SEQUENCE: 380

Gln Asp Arg Ser His Met Pro
1 5

<210> SEQ ID NO 381
<211> LENGTH: 7
<212> TYPE: PRT
<213> ORGANISM: Homo sapiens

<400> SEQUENCE: 381

Gln Asp Arg Ile His Met Pro
1 5

<210> SEQ ID NO 382
<211> LENGTH: 19
<212> TYPE: DNA
<213> ORGANISM: Homo sapiens

<400> SEQUENCE: 382
ttgagaaaaa ccaagggtg 19

<210> SEQ ID NO 383
<211> LENGTH: 19
<212> TYPE: DNA
<213> ORGANISM: Homo sapiens
<220> FEATURE:
<221> NAME/KEY: modified_base
<222> LOCATION: (10)
<223> OTHER INFORMATION: This base may or may not be present

<400> SEQUENCE: 383
ttgagaaaaa ccaagggtg 19

<210> SEQ ID NO 384
<211> LENGTH: 18
<212> TYPE: DNA
<213> ORGANISM: Homo sapiens

<400> SEQUENCE: 384
ttgagaaaac caagggtg 18

<210> SEQ ID NO 385
<211> LENGTH: 19
<212> TYPE: DNA
<213> ORGANISM: Homo sapiens

<400> SEQUENCE: 385
cacccttggt ttttctcaa 19

<210> SEQ ID NO 386
<211> LENGTH: 19
<212> TYPE: DNA
<213> ORGANISM: Homo sapiens
<220> FEATURE:
<221> NAME/KEY: modified_base
<222> LOCATION: (10)
<223> OTHER INFORMATION: This base may or may not be present

<400> SEQUENCE: 386
cacccttggt ttttctcaa 19

<210> SEQ ID NO 387
<211> LENGTH: 18
<212> TYPE: DNA
<213> ORGANISM: Homo sapiens -continued

<400> SEQUENCE: 387 caccccttggt tttctcaa 18

<210> SEQ ID NO 388
<211> LENGTH: 19
<212> TYPE: DNA
<213> ORGANISM: Homo sapiens

<400> SEQUENCE: 388
cacttctagg aaaaggaca 19

<210> SEQ ID NO 389
<211> LENGTH: 19
<212> TYPE: DNA
<213> ORGANISM: Homo sapiens

<400> SEQUENCE: 389
cacttctagk aaaaggaca 19

<210> SEQ ID NO 390
<211> LENGTH: 19
<212> TYPE: DNA
<213> ORGANISM: Homo sapiens

<400> SEQUENCE: 390
cacttctagt aaaaggaca 19

<210> SEQ ID NO 391
<211> LENGTH: 19
<212> TYPE: DNA
<213> ORGANISM: Homo sapiens

<400> SEQUENCE: 391 tgtcctttc ctagttgtg 19

<210> SEQ ID NO 392
<211> LENGTH: 19
<212> TYPE: DNA
<213> ORGANISM: Homo sapiens

<400> SEQUENCE: 392 tgtcctttm ctagttgtg 19

<210> SEQ ID NO 393
<211> LENGTH: 19
<212> TYPE: DNA
<213> ORGANISM: Homo sapiens

<400> SEQUENCE: 393
tgtcctttta ctagttgtg 19

<210> SEQ ID NO 394
<211> LENGTH: 19
<212> TYPE: DNA
<213> ORGANISM: Homo sapiens

<400> SEQUENCE: 394
aggataggag ccacatgcc 19

<210> SEQ ID NO 395
<211> LENGTH: 19
<212> TYPE: DNA

-continued

<213> ORGANISM: Homo sapiens

<400> SEQUENCE: 395
aggataggak ccacatgcc 19

<210> SEQ ID NO 396
<211> LENGTH: 19
<212> TYPE: DNA
<213> ORGANISM: Homo sapiens

<400> SEQUENCE: 396
aggataggat ccacatgcc 19

<210> SEQ ID NO 397
<211> LENGTH: 19
<212> TYPE: DNA
<213> ORGANISM: Homo sapiens

<400> SEQUENCE: 397
ggcatgtggc tcctatcct 19

<210> SEQ ID NO 398
<211> LENGTH: 19
<212> TYPE: DNA
<213> ORGANISM: Homo sapiens

<400> SEQUENCE: 398
ggcatgtggm tcctatcct 19

<210> SEQ ID NO 399
<211> LENGTH: 19
<212> TYPE: DNA
<213> ORGANISM: Homo sapiens

<400> SEQUENCE: 399
ggcatgtgga tcctatcct 19

<210> SEQ ID NO 400
<211> LENGTH: 2097
<212> TYPE: DNA
<213> ORGANISM: Homo sapiens

<400> SEQUENCE: 400
cattttaatc cactggtgct agaattatta actaaattaa tgtttatttt gaaagtcact 60
gattagatta atccacaagt attgaatttt agtcaatctt ggtggcccgg tttaactgga 120
tgttttgctt aaaaggaagg cagcaagatg caggggttat ggtttccagc cccagcttgg 180
tcacttgcat tctgtgtgtc cttagctaaa gtactgaatc tccatggtct aactttctcc 240
tctctaaact gggaataatt ttacagtggg caaagataat tgagagaata aaaagagatg 300
tgatgagtgt gaaaattctc tgtaaatttg tcataatgtc tataaacata atcgataaaa 360
cattgtataa ctgggtctaa tattttctta atgaaagagc tggaaataac tgtactggtc 420
aatttagaat aaaggtaatc ttttcagagc atgcctttgt atacacactt tgttattagt 480
gatctagtaa tgttcataaa tccagttgta tttagatctt catgaccatt gactatcagt 540
tcccatttca ggtctgcaca ttgcagtggt tctgtgccct gggtccattc agtgatttcc 600
ctgtgttcca tcttctgttg aatccacaac tgttgttctg tgtataattt ctcttccttg 660
ctgtgtatga ttacattcta ttatttgtaa caataacaga ccaaaaacaa tagaagcagc 720
catgtctgga ggtgactgga aggtggagaa gccatagatt ttcaagccct gtgccataaa 780

-continued

```
ttatgtgaga ttggcccttt ccttaatagt gctgaacaac tttcacttgt gaggtgatgc    840
agaggggaga actctaattt ttatttcttc ttttgagcgt ctccggtcct cttatcctta    900
taaacaaata acggacttct atttaatgtg aagcctgttg ctttctgaac agagtcaagg    960
tggcgtatct tcagagtaac taatgtctgg ggtttgtttt gtttttctaa aattgttctt   1020
gagccagctg tggtgtaagt ggtaatgaac cccaatgggt atcagaagat ctctgctcaa   1080
atcccggttt taccggcaat gagctgtgtg gcactgacag gtgtcctgtt ctcccagagt   1140
ttctttccca atttgaaaaa taaaaaatga taatctttat actccagtct cttttaatga   1200
tgaatataca tttatatata tacttttata tatttaatat aatatttaat agtataaata   1260
tgtatttatg ttattattat gtaataatgt atgtaacact ccctgctaat tcagtttgtc   1320
tctttgacat gtaaagtaaa taatcaccta ttattataat aatgtaataa taacacaaat   1380
attattatgt aataacatat atatttatgt atattgttta tatacattta aatatatata   1440
aatatacatt tattagctaa taatttgata tatgtatggt aattcaacat gtatgagtta   1500
tattcactat ttcatgttta ggcagctgta ttttaagtga actatactaa atatttgaaa   1560
ggcttttgtt atcaagggct aagtctccta tttttttgata tagcattaca atgtacattt   1620
tttatacaca aaatatagaa tacactgatt tccctcaagg tcataaattc ccaactggtc   1680
attaatctga gaatattgaa ttttgagtat attctaacat agaatcattt acttcagtgt   1740
ttctccatca tcacagcaca ttggaacaac cagggacttt taattaaaaa tacctgggct   1800
ccaatccaat acaattaaac cagaatctcc tagattggca ctggaaagaa ggagtaggac   1860
aaaagaacat tttatttcta tccatgggcc aaagtccact cagaaaaaaa gtataaattg   1920
gatctaggtg attgtttact ttacatgtca aagagacaca cactaaatta gcagggagtg   1980
ttataaaaac tttggagtgc aagctcacag ctgtcttaat aagaagagaa ggcttcaatg   2040
gaacctttg tggtcctggt gctgtgtctc tcttttatgc ttctcttttc actctgg      2097
```

```
<210> SEQ ID NO 401
<211> LENGTH: 440
<212> TYPE: DNA
<213> ORGANISM: Homo sapiens

<400> SEQUENCE: 401

cagagctgta ggagaaggaa gctccctcct ggccccactc ctcttcctat tattggaaat     60
atgctacaga tagatgttaa ggacatctgc aaatctttca ccaatgtaag tctgccttat    120
gttcctccag ccaattgcaa agggtaagtt atttgactgc tatttttaga caaaatatat    180
tcctggaagc acactattat aatagatcat tgtaaagcaa aatactccct ctgaacttct    240
ttgatgtttc ttttgtcttc ctattttttt ttttttttga gacggagtct cgctctattg    300
cccaggctgg agtgcagtgg cactatctcc actcactgca agctctgcct cccaggttca    360
caccattctc ctgcctcagc ctcccccgag taactgggac tacaggtgcc ctccaccatg    420
cccggctaat tttttgtatg                                                440

<210> SEQ ID NO 402
<211> LENGTH: 383
<212> TYPE: DNA
<213> ORGANISM: Homo sapiens

<400> SEQUENCE: 402

agtttcttca tttttaaaac aggtcaaatg aatgtgctga atgtgttgaa gtgaggatga     60
```

-continued actgtgtgat ttgtgtacca attgcctggg tcattgcgtg gcacatcaca ggccatctat 120
aagtggcagc tataacaatc accatcacat ttatgtacaa aattcagaaa tatcgaatct 180
atgtgtggca aatatgaaca ttaaaaaata caatgaaaat gtcagtctga atcatacata 240
gtatttggag caaatagcga cttattttgc tgctatttgc atttcctttc ccagttctca 300
aaagtctatg gtcctgtgtt caccgtgtat tttggcatga atcccatagt ggtgtttcat 360
ggatatgagg cagtgaagga agc 383

<210> SEQ ID NO 403
<211> LENGTH: 463
<212> TYPE: DNA
<213> ORGANISM: Homo sapiens

<400> SEQUENCE: 403
tactaaagga cttggtaggt gcacatattt ctgtgtcagc tttggtaact ggggtgaggg 60
ggatggaaaa cagagcccta aaaagcttct cagcagagct tagcctatct gcatggctgc 120
cgagtgttgc agcactttct tccttggctg tgaattctcc cagtttctgc cccttttttt 180
attaggaatc atttccagca atggaaagag atggaaggag atccggcgtt tctccctcac 240
aaccttgcgg aattttggga tggggaagag gagcattgag gaccgtgttc aagaggaagc 300
tcactgcctt gtggaggagt tgagaaaaac caagggtggg tgactctact ctgcgtcatt 360
gaccttaaca gttacctgtc ttcactagtg acgtccttgg aaacatttca ggggtggcca 420
ggtcttcatt gcgcatcctg gttgtcagcc ctcaggtggt gga 463

<210> SEQ ID NO 404
<211> LENGTH: 243
<212> TYPE: DNA
<213> ORGANISM: Homo sapiens

<400> SEQUENCE: 404
atgctcaact catatttaag gtaaaagtaa tgtgtttatt tcatccatgc tgattttttt 60
tggacacatg gggaatttgt aagatatgtt taaaatttct aaatttcctt tatgtcttaa 120
cagatgcaaa tcttttaaat atttattttt taataatttt tttaaaaatt tttaaatctt 180
tagcttcacc ctgtgatccc actttcatcc tgggctgtgc tccctgcaat gtgatctgct 240
ccg 243

<210> SEQ ID NO 405
<211> LENGTH: 370
<212> TYPE: DNA
<213> ORGANISM: Homo sapiens

<400> SEQUENCE: 405
tcaggattct gaactcccca tggatccagg taaggccaag attttatttt ccttggaaac 60
catttattca aggttgtagg gaagacttgg tttaaaaatg agaaaattga tactaaaatg 120
cttttataca ataaaaatga tgtatgagtg aagaaaataa ttaccacctt tgatttcctg 180
ttcaaaattt tcagcctcca atctttaggt acagaaaatt gctatatgtg cacaataaaa 240
atttccccat cagaagtgca aggggtcagg gaattccctt tcctagccaa gcaaagctgt 300
gaacagatgg cacctggaaa attgggtcac tcccacccta atactgtgct tttctagtgg 360
tcttagtaaa 370

<210> SEQ ID NO 406
<211> LENGTH: 294

-continued

<212> TYPE: DNA
<213> ORGANISM: Homo sapiens

<400> SEQUENCE: 406
tgggagatat acctaatgta tatgacgagt tattgggtgc agtacaccaa cctggcacat 60
gtatacatat gtgacaaacc tgcactttgt gcacatatac cctagaactt aaagtataat 120
aaaaaatgta tatatgtata aaaatttccc ttcaaaatgg acatgatgtc ttattcatat 180
ttatagttat aatttcaatc agggcttggt gtaagataca tatatcttat gacatgttta 240
tatttaatat tcttttctct tttaggtctg caataatttc cctctactca ttga 294

<210> SEQ ID NO 407
<211> LENGTH: 327
<212> TYPE: DNA
<213> ORGANISM: Homo sapiens

<400> SEQUENCE: 407
acaacaaagt gcttaaaaat gttgctctta cacgaagtta cattagggag aaagtaaaag 60
aacaccaagc atcactggat gttaacaatc ctcgggactt tatcgattgc ttcctgatca 120
aaatggagca ggtaagatat tagcaacaga tcagtatttt gatttcttgt ccattttgtg 180
attcatcgaa tccttctgta atttactaag gatgtttaaa tgatcaggcc agtaatgctt 240
gacaagcatc ttaattactt attgtattta tgggcctgca ctaaacatca tggaaaatac 300
aaaattgtcc aatggctaga atgcata 327

<210> SEQ ID NO 408
<211> LENGTH: 346
<212> TYPE: DNA
<213> ORGANISM: Homo sapiens

<400> SEQUENCE: 408
ataacacaaa ttgaagtaag acagggcatc ggtatacttc tgcttttatt tctggggaaa 60
gaaatattct gtgtgactaa cctaagcagc gaatgatttc atgaatggaa cttgtaggtc 120
tgtcaggaaa taaagtttga gtcaactgat ctgcagtttc tgccatacca cacagttgct 180
ttttctaata ctgtactgtc cagtatctct tttggctaac tttaaaaaat agtatgtttt 240
ttaaaattta gtgtatttag atatactggc acataatttg tcagataatt gcatgaaatc 300
acttctagga aaaggacaac caaaagtcag aattcaatat tgaaaa 346

<210> SEQ ID NO 409
<211> LENGTH: 199
<212> TYPE: DNA
<213> ORGANISM: Homo sapiens

<400> SEQUENCE: 409
tcctgctcct gctgaagcac ccagaggtca caggtaggac cacagatgat gaacaaagtg 60
aatttcagaa caatgctgag aagatggtgc cagtatcctc caccttgttt ctctcagaga 120
aggctcattc tttaaatttc tgtgtcatca gctgtaatct gtctaaattt gatgacacaa 180
tttaaaatga catctttgt 199

<210> SEQ ID NO 410
<211> LENGTH: 247
<212> TYPE: DNA
<213> ORGANISM: Homo sapiens

<400> SEQUENCE: 410

-continued

```
tatattatgg taattctttt tatatggctg gttgtacttc tggacatgta actcatgttt     60

gtaatgttgc tgggattttt atatcatgtt aatgtggcca tgaattgcta tgacaaatgt    120

tccatatatc ttcgtttcca tcagttcttt cttgtgtctt gtcagctaaa gtccaggaag    180

agattgatca tgtaattggc agacacagga gcccctgcat gcaggatagg agccacatgc    240

cttacac                                                              247


<210> SEQ ID NO 411
<211> LENGTH: 175
<212> TYPE: DNA
<213> ORGANISM: Homo sapiens

<400> SEQUENCE: 411

gccccatgca gtgaccactg atactaagtt cagaaactac ctcatcccca aggtaagctt     60

gtttctctta cactatattt ctgtacttct gaaatttcca tagtgctggt ttggttccaa    120

ccctctaaca acacaagatg agagaagtgc aaaactcata catgtggcag cttga         175


<210> SEQ ID NO 412
<211> LENGTH: 226
<212> TYPE: DNA
<213> ORGANISM: Homo sapiens

<400> SEQUENCE: 412

ccaccactgg ccttaagctg atccatgtaa attactgtgt ctggctggac ctgagtttcc     60

tcatctatag atcaacgtta tggcgctacg tgatgtccac tacttctcct cacttctgga    120

cttctttata aatcagatta tctgttttgt tacttccagg gcacaaccat aatggcatta    180

ctgacttccg tgctacatga tgacaaagaa tttcctaatc caaata                   226


<210> SEQ ID NO 413
<211> LENGTH: 300
<212> TYPE: DNA
<213> ORGANISM: Homo sapiens

<400> SEQUENCE: 413

tttcctaatc caaatatctt tgaccctggc cactttctag ataagaatgg caactttaag     60

aaaagtgact acttcatgcc tttctcagca ggtaatagaa actcgtttcc atttgtattt    120

aaaggaaaga gagaactttt tggaattagt tggaatttac atggcacctc ctctggggct    180

ggtagaattg ctatttgtcc atgatcaaga gcaccactct taacacccat gtgctccacc    240

ctcacaatac accatcatta ttgggccaga tagcggggct tgcaggagtt aactctgttg    300


<210> SEQ ID NO 414
<211> LENGTH: 248
<212> TYPE: DNA
<213> ORGANISM: Homo sapiens

<400> SEQUENCE: 414

aatatgtctc tttttgtaca tttgtttgtc ccaccatcca ttaatcaatc catcatgtca     60

tccatccatt catccacatg ttcattcatc tacccaatca ttaatcaatt atttactgca    120

tattctgttt gtgcaagtca caaatgactg tttgtcacag tcacagttaa acacaaggag    180

taactacttc ctttctttgt tatcttcagg aaaacgaatt tgtgcaggag aaggacttgc    240

ccgcatgg                                                             248


<210> SEQ ID NO 415
<211> LENGTH: 300
```

-continued

<212> TYPE: DNA
<213> ORGANISM: Homo sapiens

<400> SEQUENCE: 415
tctgcttcat ccctgtctga agaatgctag cccatctggc tgccgatctg ctatcacctg 60
caactctttt tttatcaagg acattcccac tattatgtct tctctgacct ctcatcaaat 120
cttcccattc actcaatatc ccataagcat ccaaactcca ttaaggagag ttgttcaggt 180
cactgcacaa atatatctgc aattattcat actctgtaac acttgtatta attgctgcat 240
atgctaatac ttttctaatg ctgacttttt aatatgttat cactgtaaaa cacagaaaag 300

<210> SEQ ID NO 416
<211> LENGTH: 1866
<212> TYPE: DNA
<213> ORGANISM: Homo sapiens

<400> SEQUENCE: 416
agtgcaagct cacagctgtc ttaataagaa gagaaggctt caatggaacc ttttgtggtc 60
ctggtgctgt gtctctcttt tatgcttctc ttttcactct ggagacagag ctgtaggaga 120
aggaagctcc ctcctggccc cactcctctt cctattattg gaaatatgct acagatagat 180
gttaaggaca tctgcaaatc tttcaccaat ttctcaaaag tctatggtcc tgtgttcacc 240
gtgtattttg gcatgaatcc catagtggtg tttcatggat atgaggcagt gaaggaagcc 300
ctgattgata atggagagga gttttctgga agaggcaatt ccccaatatc tcaaagaatt 360
actaaaggac ttggaatcat ttccagcaat ggaaagagat ggaaggagat ccggcgtttc 420
tccctcacaa ccttgcggaa ttttgggatg ggaagagga gcattgagga ccgtgttcaa 480
gaggaagctc actgccttgt ggaggagttg agaaaaacca aggcttcacc ctgtgatccc 540
actttcatcc tgggctgtgc tccctgcaat gtgatctgct ccgttgtttt ccagaaacga 600
tttgattata aagatcagaa ttttctcacc ctgatgaaaa gattcaatga aaacttcagg 660
attctgaact ccccatggat ccaggtctgc aataatttcc ctctactcat tgattgtttc 720
ccaggaactc acaacaaagt gcttaaaaat gttgctctta cacgaagtta cattagggag 780
aaagtaaaag aacaccaagc atcactggat gttaacaatc ctcgggactt tatcgattgc 840
ttcctgatca aaatggagca ggaaaaggac aaccaaaagt cagaattcaa tattgaaaac 900
ttggttggca ctgtagctga tctatttgtt gctggaacag agacaacaag caccactctg 960
agatatggac tcctgctcct gctgaagcac ccagaggtca cagctaaagt ccaggaagag 1020
attgatcatg taattggcag acacaggagc ccctgcatgc aggataggag ccacatgcct 1080
tacactgatg ctgtagtgca cgagatccag agatacagtg accttgtccc caccggtgtg 1140
ccccatgcag tgaccactga tactaagttc agaaactacc tcatccccaa gggcacaacc 1200
ataatggcat tactgacttc cgtgctacat gatgacaaag aatttcctaa tccaaatatc 1260
tttgaccctg gccactttct agataagaat ggcaacttta agaaaagtga ctacttcatg 1320
cctttctcag caggaaaacg aatttgtgca ggagaaggac ttgcccgcat ggagctattt 1380
ttatttctaa ccacaatttt acagaacttt aacctgaaat ctgttgatga tttaaagaac 1440
ctcaatacta ctgcagttac caaagggatt gtttctctgc caccctcata ccagatctgc 1500
ttcatccctg tctgaagaat gctagcccat ctggctgctg atctgctatc acctgcaact 1560
ctttttttat caaggacatt cccactatta tgtcttctct gacctctcat caaatcttcc 1620
cattcactca atatcccata agcatccaaa ctccattaag gagagttgtt caggtcactg 1680

-continued

```
cacaaatata tctgcaatta ttcatactct gtaacacttg tattaattgc tgcatatgct   1740

aatactttc taatgctgac tttttaatat gttatcactg taaaacacag aaaagtgatt   1800

aatgaatgat aatttagatc catttctttt gtgaatgtgc taaataaaaa gtgttattaa   1860

ttgcta                                                              1866


<210> SEQ ID NO 417
<211> LENGTH: 490
<212> TYPE: PRT
<213> ORGANISM: Homo sapiens

<400> SEQUENCE: 417

Met Glu Pro Phe Val Val Leu Val Leu Cys Leu Ser Phe Met Leu Leu
1               5                   10                  15

Phe Ser Leu Trp Arg Gln Ser Cys Arg Arg Arg Lys Leu Pro Pro Gly
            20                  25                  30

Pro Thr Pro Leu Pro Ile Ile Gly Asn Met Leu Gln Ile Asp Val Lys
        35                  40                  45

Asp Ile Cys Lys Ser Phe Thr Asn Phe Ser Lys Val Tyr Gly Pro Val
    50                  55                  60

Phe Thr Val Tyr Phe Gly Met Asn Pro Ile Val Val Phe His Gly Tyr
65                  70                  75                  80

Glu Ala Val Lys Glu Ala Leu Ile Asp Asn Gly Glu Glu Phe Ser Gly
                85                  90                  95

Arg Gly Asn Ser Pro Ile Ser Gln Arg Ile Thr Lys Gly Leu Gly Ile
            100                 105                 110

Ile Ser Ser Asn Gly Lys Arg Trp Lys Glu Ile Arg Arg Phe Ser Leu
        115                 120                 125

Thr Asn Leu Arg Asn Phe Gly Met Gly Lys Arg Ser Ile Glu Asp Arg
    130                 135                 140

Val Gln Glu Glu Ala His Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Val Val Phe Gln Lys Arg Phe Asp Tyr Lys Asp Gln
            180                 185                 190

Asn Phe Leu Thr Leu Met Lys Arg Phe Asn Glu Asn Phe Arg Ile Leu
        195                 200                 205

Asn Ser Pro Trp Ile Gln Val Cys Asn Asn Phe Pro Leu Leu Ile Asp
    210                 215                 220

Cys Phe Pro Gly Thr His Asn Lys Val Leu Lys Asn Val Ala Leu Thr
225                 230                 235                 240

Arg Ser Tyr Ile Arg Glu Lys Val Lys Glu His Gln Ala Ser Leu Asp
                245                 250                 255

Val Asn Asn Pro Arg Asp Phe Met Asp Cys Phe Leu Ile Lys Met Glu
            260                 265                 270

Gln Glu Lys Asp Asn Gln Lys Ser Glu Phe Asn Ile Glu Asn Leu Val
        275                 280                 285

Gly Thr Val Ala Asp Leu Phe Val Ala Gly Thr Glu Thr Thr Ser Thr
    290                 295                 300

Thr Leu Arg Tyr Gly Leu Leu Leu Leu Leu Lys His Pro Glu Val Thr
305                 310                 315                 320

Ala Lys Val Gln Glu Glu Ile Asp His Val Ile Gly Arg His Arg Ser
                325                 330                 335
```

-continued

```
Pro Cys Met Gln Asp Arg Ser His Met Pro Tyr Thr Asp Ala Val Val
            340                 345                 350

His Glu Ile Gln Arg Tyr Ser Asp Leu Val Pro Thr Gly Val Pro His
        355                 360                 365

Ala Val Thr Thr Asp Thr Lys Phe Arg Asn Tyr Leu Ile Pro Lys Gly
    370                 375                 380

Thr Thr Ile Met Ala Leu Leu Thr Ser Val Leu His Asp Asp Lys Glu
385                 390                 395                 400

Phe Pro Asn Pro Asn Ile Phe Asp Pro Gly His Phe Leu Asp Lys Asn
                405                 410                 415

Gly Asn Phe Lys Lys Ser Asp Tyr Phe Met Pro Phe Ser Ala Gly Lys
            420                 425                 430

Arg Ile Cys Ala Gly Glu Gly Leu Ala Arg Met Glu Leu Phe Leu Phe
        435                 440                 445

Leu Thr Thr Ile Leu Gln Asn Phe Asn Leu Lys Ser Val Asp Asp Leu
    450                 455                 460

Lys Asn Leu Asn Thr Thr Ala Val Thr Lys Gly Ile Val Ser Leu Pro
465                 470                 475                 480

Pro Ser Tyr Gln Ile Cys Phe Ile Pro Val
                485                 490
```

POLYMORPHISMS IN THE HUMAN GENE FOR CYTOCHROME P450 POLYPEPTIDE 2C8 AND THEIR USE IN DIAGNOSTIC APPLICATIONS

The present invention relates to a polymorphic CYP2C8 polynucleotide. Moreover, the invention relates to genes or vectors comprising the polynucleotides of the invention and to a host cell genetically engineered with the polynucleotide or gene of the invention. Further, the invention relates to methods for producing molecular variant polypeptides or fragments thereof, methods for producing cells capable of expressing a molecular variant polypeptide and to a polypeptide or fragment thereof encoded by the polynucleotide or the gene of the invention or which is obtainable by the method or from the cells produced by the method of the invention. Furthermore, the invention relates to an antibody which binds specifically the polypeptide of the invention. Moreover, the invention relates to a transgenic non-human animal. The invention also relates to a solid support comprising one or a plurality of the above mentioned polynucleotides, genes, vectors, polypeptides, antibodies or host cells. Furthermore, methods of identifying a polymorphism, identifying and obtaining a pro-drug or drug or an inhibitor are also encompassed by the present invention. In addition, the invention relates to methods for producing of a pharmaceutical composition and to methods of diagnosing a disease. Further, the invention relates to a method of detection of the polynucleotide of the invention. Furthermore, comprised by the present invention are a diagnostic and a pharmaceutical composition. Even more, the invention relates to uses of the polynucleotides, genes, vectors, polypeptides or antibodies of the invention. Finally, the invention relates to a diagnostic kit.

Cytochrome P450 enzymes are metabolic enzymes differentially expressed in several tissues. Cytochrome P450 2C mRNA was detected in abundance in hepatic tissue, to a lesser extend in extrahepatic tissues, e.g. kidney, adrenal gland, brain, uterus, mammary gland, ovary and duodenum, but neither in testes nor ovary (Klose, J Biochem Mol Toxicol 13 (1999), 289-95). Of the CYP2C subfamily, clustered on chromosome 10q24.1 (Gray, Genomics 28 (1995), 328-32), CYP2C9 and 2C19 are those which gained major interest due to their prominent role in metabolizing therapeutic drugs. Differential breakdown of their substrates led to the identification of alleles for poor (PM) or extensive metabolizers (EM). Nevertheless, the existence of minor CYP2C8 genes was known and characterized to display about 90% amino acid homology (Goldstein, Pharmacogenetics 4 (1994), 285-99). Only recently, the genomic sequence of CYP2C8, spanning a 31 kb region, was published. Interestingly, the gene is involved in intergenic splicing with CYP2C18 composed of 9 exons (Finta, Genomics 63 (2000), 433-8).

Arachidonic acid is one major endogenous substrate for CYP2C8 and specifically epoxidated to equivalent forms of 11, 12- and 14, 15-epoxides. Concerning xenobiotical substrates CYP2C8 represents the isoform with the narrowest substrate specificity. The anticancer drug TAXOL (paclitaxel), also well known to be a substrate for MDR-1 (Mechetner, Clin Cancer Res. 4 (1998), 389-398), is known to be the prototype. Several other drugs, e.g. verapamil (Tracy, Br J Clin Pharmacol. 47 (1999), 545-52) and rosiglitazone (Malinowski, Clin Ther. 22 (2000), 1151-68) are preferable substrates for CYP2C8 in comparison to other CYP2Cs or CYP3As. Drugs like benzphetamine, retinoic acid, tolbutamide, benzo(a)pyrene, carbamazepine and R-ibuprofen represent a minor contribution of CYP2C8 (Wrighton, J Clin Invest. 80 (1987), 1017-22; Relling, J Pharmacol Exp Ther. 252 (1990), 442-7; Hamman, Biochem Pharmacol. 54 (1997), 33-41; Kerr, Biochem Pharmacol. 47 (1994), 1969-79; Yun, Cancer Res. 52 (1992), 1868-74; Leo, Arch Biochem Biophys 259 (1987), 241-9). So far, the enzymatic induction has only be observed by phenobarbital and rifampicin (Morel, Eur J. Biochem. 191 (1990), 437-44). Thum and Borlak (Thum and Borlak, Br J Pharmacol 130 (2000), 1745-52) found a strong correlation between tissue specific gene expression and enzyme activity. Increased CYP2C8 mRNA expression within the right heart ventricle might explain for the lack of efficacy of cardioselective drugs like verapamil. In a porcine system, Fisslthaler (Fisslthaler, Nature 401 (1999), 493-7; Fisslthaler, Semin Perinatol 24 (2000), 15-9; Fisslthaler, Circ Res. 88 (2001), 44-51) could show that CYP2C8 meets all criteria for the coronary endothelium-derived hyperpolarisation factor synthase acting on vascular smooth muscle cells prior to dilation.

Since the mRNA has been published, first single nucleotide polymorphisms (SNPs) in exons 3, 5 and 8 were reported in an abstract (Goldstein, Microsomes and Oxidation, Stresa (2000), Italy): an exchange in position 139 of Arg to Lys (exon 3) could be linked to a SNP in exon 8 (Lys399Arg), occurring primarily in Caucasians, and correlated to poor metabolizing phenotype (PM). Exon 5 displays a mutation (Iso269Phe) that is associated with poor metabolizing enzyme restricted to African-Americans. The regulation of the 2Cs is supposed to be modified by polymorphisms in the untranslated region. Regarding CYP2C8, two previously unidentified transcription regulatory factor sites for C/EBP and HPF-1, but no relevant SNPs were identified by Goldstein and coworkers (Goldstein, Microsomes and Oxidation, Stresa Italy (2000), Italy) in that region.

However, means and methods for reliable and improved diagnosing and treating a variety of diseases and disorders or for predicting and overcoming undesired drug effects or interactions based on dysfunctions or dysregulations of cytochrome 2C8 variants were not available yet but are nevertheless highly desirable. Thus, the technical problem underlying the present invention is to comply with the above specified needs.

The solution to this technical problem is achieved by providing the embodiments characterized in the claims.

Figure 1:
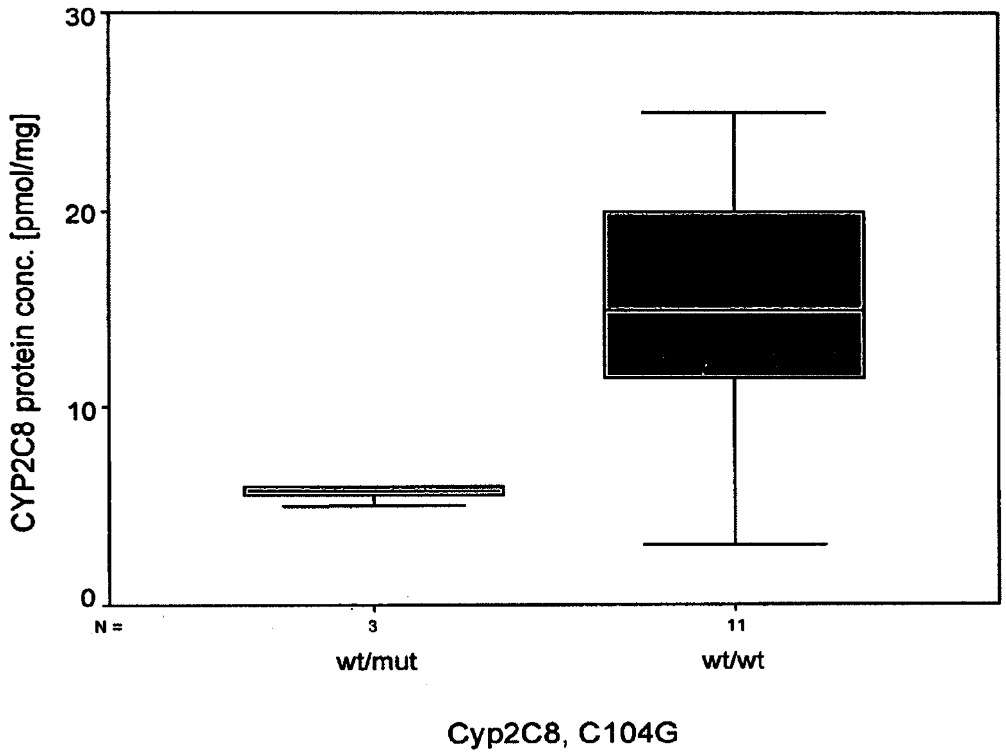
FIG. 1

Correlation of the SNP C104G (Exon 5, 1264M) with reduced protein levels of CYP2C8. Expression levels of 14 individuals were determined by Western Blot analysis and LC-MS using verapamil as specific substrate. The boxplots show the distribution of samples according to the genotype at amino acid position 264. The genotype-phenotype correlation is significant (p=0.037, N=14).

FIG. 2

Correlation of the SNP −370 relative to the start codon ATG with increased expression levels as detected by western blotting, using the drug TAXOL (paclitaxel) as specific substrate. As shown in the boxplots the genotype-phenotype correlation is significant between homozygous wild type and heterozygous mutant samples (p=0.044, N=20). (One homozygous sample was analyzed and yielded expression levels >400).

FIG. 3

Correlation of the SNP at position −370 in the untranslated region based on deviates from mean values of CYP2C8 expression levels from two independent sample collectives (N=62). The phenotype of the patients was determined by LC/MS and Western Blot. The phenotype-genotype correlation is significant as shown in the boxplots (p=0.017 for homozygous vs wildtype and p=0.071 for heterozygous vs wildtype).

FIG. 4

Correlation of the allele including the linked SNPs G-1207A, delAT-640/41 (both in the promoter), G270A (exon 3), and A206G (exon 8) with a poor metabolizer phenotype (PM). However, no homozygous individuals for this allele could yet be phenotyped. The data shown in the box plot do only show a trend (p=0,071; N=18) but no significance.

FIG. 5

Transfection of LS174T cells with either a CYP2C8 wild type promoter construct or two SNP(s) containing promoter fragments (G-1207A and −640 to 641delAT or T-370G). Using the eukaryotic pGL3 expression vector mean values of six independent transfection assays were analysed following normalisation of 2C8 wild type activity to 100%.

FIG. 6

Computer modeled CYP2C8 enzyme structure of the protein variants Thr 159 Pro (frameshift), Glu 274 Stop and Gly 365 Ser. Dark grey represents the unchanged structure of the variant protein, the light grey prepresents the missing amino acids of the CYP2C8 variant structure. The circle indicates the active site of the enzyme with the altered amino acid Gly 365 Ser in dark.

FIG. 7A-D

Reference or wild type GenBank sequences for the polynucleotides, polypeptide and mRNA according to the present invention (SEQ ID NOS: 400-417, respectively, in order of appearance).

Accordingly, the present invention relates to a polynucleotide comprising a polynucleotide selected from the group consisting of:

(a) a polynucleotide having the nucleic acid sequence of SEQ ID NO: 54, 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150, 153, 156, 159, 162, 165, 168, 171, 174, 177, 180, 183, 186, 189, 192, 195, 198, 201, 210, 213, 216, 219, 222, 225, 228, 231, 234, 237, 240, 243, 246, 249, 252, 255, 258, 261, 264, 267, 270, 273, 276, 279, 282, 285, 288, 291, 306, 309, 318, 321, 324, 327, 330, 333, 342, 345, 348, 351, 354, 357, 360, 363, 366, 369, 384, 387, 390, 393, 396 or 399;

(b) a polynucleotide encoding a polypeptide having the amino acid sequence of SEQ ID NO: 6, 8, 10, 12, 18, 377, 379 or 381;

(c) a polynucleotide capable of hybridizing to a CYP2C8 gene, wherein said polynucleotide is having at a position corresponding to position 411, 560, 713, 817, 824, 831, 879, 886, 1058, 1627, 1668, 1767, 1887, 1905 or 1952 (GenBank accession No: AF136830.1), at a position corresponding to position 171 or 258 (GenBank accession No: AF136832.1), at a position corresponding to position 122, 150, 182, 334, 339 or 378 (GenBank accession No: AF136833.1), at a position corresponding to position 162, 163, 243 (GenBank accession No: AF136834.2) or at position 583 (GenBank accession No: NM_000770.1), at a position corresponding to position 13 or 180 (GenBank accession No: AF136835.1), at a position corresponding to position 116, 132, 172 or 189 (GenBank accession No: AF136836.1), at a position corresponding to position 42 or 101 (GenBank accession No: AF136837.1), at a position corresponding to position 309 (GenBank accession No: AF136838.1), at a position corresponding to position 1135 (GenBank accession No: NM_000770.1), at a position corresponding to position 232 (GenBank accession No: AF136840.1), at a position corresponding to position 206 (GenBank accession No: AF136842.1), at a position corresponding to position 30, 87, 167, 197, 212, 221, 255 or 271 (GenBank accession No: AF136843.1), at a position corresponding to position 118 (GenBank accession No: AF136844.1), at a position corresponding to position 44 (GenBank accession No: AF136845.1) of the cytochrome 2C8 gene (GenBank accession No: GI: 13787189) a nucleotide substitution, at a position corresponding to position 306 to 307, 1271 to 1273 or 1397 to 1398 of the CYP2C8 gene (GenBank accession No: AF136830.1), at a position corresponding to position 329 of the CYP2C8 gene (GenBank accession No: AF136833.1), at a position corresponding to position 87 of the CYP2C8 gene (GenBank accession No: AF136834.2) a deletion of one or more nucleotides or at a position corresponding to position 1785/1786 of the CYP2C8 gene (GenBank accession No: AF136830.1) or at a position corresponding to position 180/181 of the CYP2C8 gene (GenBank accession No: AF136833.1) an insertion of one or more nucleotides;

(d) a polynucleotide capable of hybridizing to a CYP2C8 gene, wherein said polynucleotide is having at a position corresponding to position 411, 817, 824, 831, 879, 1058, 1767 or 1887 of the CYP2C8 gene (GenBank accession No: AF136830.1) an A, at a position corresponding to position 560 or 1668 of the CYP2C8 gene (GenBank accession No: AF136830.1) a G, at a position corresponding to position 713 or 886 of the CYP2C8 gene (GenBank accession No: AF136830.1) a T, at a position corresponding to position 1627, 1905 or 1952 of the CYP2C8 gene (GenBank accession No: AF136830.1) a C, at a position corresponding to position 258 of the CYP2C8 gene (GenBank accession No: AF136832.1) a T, at a position corresponding to position 171 of the CYP2C8 gene (GenBank accession No: AF136832.1) a C, at a position corresponding to position 122, 150 or 334 of the CYP2C8 gene (GenBank accession No: AF136833.1) an A, at a position corresponding to position 182 or 378 of the CYP2C8 gene (GenBank accession No: AF136833.1) a C, at a position corresponding to position 162, 163, 243 [identical to position corresponding to position 583 of the CYP2C8 gene (GenBank accession No: NM_000770.1) of the CYP2C8 gene (GenBank accession No: AF136834.2) an A, at a position corresponding to position 180 of the CYP2C8 gene (GenBank accession No: AF136835.1) an A, at a position corresponding to position 13 of the CYP2C8 gene (GenBank accession No: AF136835.1) a G, at a position corresponding to position 116 or 132 of the CYP2C8 gene (GenBank accession No: AF136836.1) a G, at a position corresponding to position 172 of the CYP2C8 gene (GenBank accession No: AF136836.1) a G, at a position corresponding to position 189 of the CYP2C8 gene (GenBank accession No: AF136836.1) a C, at a position corresponding to position 42 or 101 of the CYP2C8 gene (GenBank accession No: AF136837.1) a G, at a position corresponding to position 1135 of the CYP2C8 gene (GenBank accession No: GI: 13787189) an A, at a position corresponding to position 309 of the CYP2C8 gene (GenBank accession No: AF136838.1) a T, at a position corresponding to position 232 (GenBank accession No: 136840.1) a T, at a position corresponding to position 30 or 212 of the CYP2C8 gene (GenBank accession No: AF136843.1) a T, at a position corresponding to position 87 of the CYP2C8 gene (GenBank accession No: AF136843.1) a G, at a position corresponding to position 167 or 197 of the CYP2C8 gene (GenBank accession No: AF136843.1) an A, at a position corresponding to position 221, 255 or 271 of the CYP2C8 gene (GenBank accession No: AF136843.1) a C, at a position corresponding to position 118 of the CYP2C8 gene (GenBank accession No: AF136844.1) an A, at a position corresponding to position 44 of the CYP2C8 gene (GenBank accession No: AF136845.1) a T;

(e) a polynucleotide encoding a molecular CYP2C8 variant polypeptide or fragment thereof, wherein said polypeptide comprises an amino acid substitution at a position corresponding to any one of position 159, 181, 209, 244, 263, 274, 343 or 365 of the CYP2C8 polypeptide (GI: 13787189); and (f) a polynucleotide encoding a molecular CYP2C8 variant polypeptide or fragment thereof, wherein said polypeptide comprises an amino acid substitution of T to P at position corresponding to position 159 (frameshift), V to I at a position corresponding to position 181, N to S at a position corresponding to position 209, I to V at a position corresponding to position 244, F to L at a position corresponding to position 263, E to Stop at a position corresponding to position 274, G to S at a position corresponding to position 365 or S to I at a position corresponding to position 343 of the CYP2C8 polypeptide (GenBank accession No: Gl: 13787189).

In the context of the present invention the term "polynucleotides" or the term "polypeptides" refers to different variants of a polynucleotide or polypeptide. Said variants comprise a reference or wild type sequence of the polynucleotides or polypeptides of the invention as well as variants which differ therefrom in structure or composition. Reference or wild type sequences for the polynucleotides are GenBank accession No: NM_000770.1 for mRNA. Reference or wild type sequence for the polynucleotide of the invention is for the 5'UTR: GenBank accession No: AF136830.1; for exon 1: GenBank accession No: AF136831.1; for exon 2: GenBank accession No: AF136832.1 and AF136833.1; for exon 3: GenBank accession No: AF136833.1; for exon 4: GenBank accession No: AF136834.2 and AF136835.1; for exon 5: GenBank accession No: AF136836.1 and AF136837.1; for exon 6: GenBank accession No: AF136838.1 and AF136839.1; for exon 7: GenBank accession No: AF136840.1 and AF136841.1; for exon 8: GenBank accession No: AF136842.1 and AF136843.1; for exon 9/3'UTR: GenBank accession No: AF136844.1 and AF136845.1; partly in combination with NM_000770.1 (mRNA). Reference or wild type sequence for the polypeptide of the CYP2C8 gene is GenBank accession No: GI: 13787189. In the context of the present invention the term "5'UTR" refers to the untranslated region 5' to the ATG start codon including the 5'-upstream region encompassing the promoter. The term "3'UTR" refers to the untranslated region 3' to the Stop codon.

The differences in structure or composition usually occur by way of nucleotide or amino acid substitution(s), addition(s) and/or deletion(s). Preferred substitution in accordance with the present invention are a T to G substitution at a position corresponding to position 1668 (GenBank accession No: AF136830.1), a G to A substitution at a position corresponding to position 831 (GenBank accession No: AF136830.1), a G to T substitution at a position corresponding to position 309 (GenBank accession No: AF136838.1) and 232 (GenBank accession No: AF136840.1) of the CYP2C8 gene. Preferred deletions in accordance with the invention are an AT deletion at a position corresponding to position 1397 to 1398 (GenBank accession No: AF136830.1) and a deletion of at least one A at a position corresponding to position 329 (GenBank accession No: AF136833.1) of the CYP2C8 gene.

In accordance with the present invention it has also been found that a deletion of the nucleotide A at a position corresponding to position 329 (GenBank accession No: AF136833.1) of the CYP2C8 gene leads to an altered C-terminus of the protein encoding a CYP2C8 polypeptide wherein said polypeptide comprises an amino acid substitution of T to P at a position corresponding to position 159 of the CYP2C8 polypeptide (GenBank accession No: GI: 13787189). In accordance with the present invention it has also been found that a substitution of a G to a T at a position corresponding to position 309 (GenBank accession No: AF136838.1) of the CYP2C8 gene leads to a polypeptide wherein said polypeptide comprises an amino acid substitution of E to a premature termination (stop) at a position corresponding to position 274 of the CYP2C8 polypeptide (GenBank accession No: GI: 13787189) and a substitution of the nucleotide G to an A at a position corresponding to position 1135 (GenBank accession No: NM_000770.1) of the CYP2C8 gene leads to a polypeptide wherein said polypeptide comprises an amino acid substitution of G to S at a position corresponding to position 365 of the CYP2C8 polypeptide (GenBank accession No: GI: 13787189). This will alter the structure or confirmation of the protein and will abolish the activity of the drug metabolizing enzyme.

Preferably, said nucleotide substitution(s), addition(s) or deletion(s) comprised by the present invention result(s) in one or more changes of the corresponding amino acid(s) of the polypeptides of the invention.

The variant polynucleotides and polypeptides also comprise fragments of said polynucleotides or polypeptides of the invention. The polynucleotides and polypeptides as well as the aforementioned fragments thereof of the present invention are characterized as being associated with a CYP2C8 dysfunction or dysregulation comprising, e.g., insufficient and/or altered metabolism. Said dysfunctions or dysregulations referred to in the present invention cause a disease or disorder or a prevalence for said disease or disorder. Preferably, as will be discussed below in detail, said disease is a deficiency in the metabolism of certain drugs which are metabolized by CYP2C8, e.g. TAXOL (paclitaxel), Verapamil, or any other disease caused by a dysfunction or dysregulation due to a polynucleotide or polypeptides of the invention, also referred to as CYP2C8 gene associated diseases in the following.

The term "hybridizing" as used herein refers to polynucleotides which are capable of hybridizing to the polynucleotides of the invention or parts thereof which are associated with a CYP2C8 dysfunction or dysregulation. Thus, said hybridizing polynucleotides are also associated with said dysfunctions and dysregulations. Preferably, said polynucleotides capable of hybridizing to the polynucleotides of the invention or parts thereof which are associated with CYP2C8 dysfunctions or dysregulations are at least 70%, at least 80%, at least 95% or at least 100% identical to the polynucleotides of the invention or parts thereof which are associated with CYP2C8 dysfunctions or dysregulations. Therefore, said polynucleotides may be useful as probes in Northern or Southern Blot analysis of RNA or DNA preparations, respectively, or can be used as oligonucleotide primers in PCR analysis dependent on their respective size. Also comprised by the invention are hybridizing polynucleotides which are useful for analyzing DNA-Protein interactions via, e.g., electrophoretic mobility shift analysis (EMSA). Preferably, said hybridizing polynucleotides comprise at least 10, more preferably at least 15 nucleotides in length while a hybridizing polynucleotide of the present invention to be used as a probe preferably comprises at least 100, more preferably at least 200, or most preferably at least 500 nucleotides in length.

It is well known in the art how to perform hybridization experiments with nucleic acid molecules, i.e. the person skilled in the art knows what hybridization conditions s/he has to use in accordance with the present invention. Such hybridization conditions are referred to in standard text books such as Molecular Cloning A Laboratory Manual, Cold Spring Harbor Laboratory (1989) N.Y. Preferred in accordance with the present inventions are polynucleotides which are capable of hybridizing to the polynucleotides of the invention or parts thereof which are associated with a CYP2C8 dysfunction or dysregulation under stringent hybridization conditions, i.e. which do not cross hybridize to unrelated polynucleotides such as polynucleotides encoding a polypeptide different from the CYP2C8 polypeptides of the invention.

The term "corresponding" as used herein means that a position is not only determined by the number of the preceding nucleotides and amino acids, respectively. The position of a given nucleotide or amino acid in accordance with the present invention which may be deleted, substituted or comprise one or more additional nucleotide(s) may vary due to deletions or additional nucleotides or amino acids elsewhere in the gene or the polypeptide. Thus, under a "corresponding position" in accordance with the present invention it is to be understood that nucleotides or amino acids may differ in the indicated number but may still have similar neighboring nucleotides or amino acids. Said nucleotides or amino acids which may be exchanged, deleted or comprise additional nucleotides or amino acids are also comprised by the term "corresponding position". Said nucleotides or amino acids may for instance together with their neighbors form sequences which may be involved in the regulation of gene expression, stability of the corresponding RNA or RNA editing, as well as encode functional domains or motifs of the protein of the invention.

By, e.g., "position 1271 to 1273" it is meant that said polynucleotide comprises one or more deleted nucleotides which are deleted between positions 1271 and position 1273 of the corresponding wild type version of said polynucleotide. The same applies mutatis mutandis to all other position numbers referred to in the above embodiment which are drafted in the same format.

By, e.g., "position 180/181" it is meant that said polynucleotide comprises one or more additional nucleotide(s) which are inserted between positions 180 and position 181 of the corresponding wild type version of said polynucleotide. The same applies mutatis mutandis to all other position numbers referred to in the above embodiment which are drafted in the same format, i.e. two consecutive position numbers separated by a slash (/).

In accordance with the present invention, the mode and population distribution of genetic variations in the CYP2C8 gene has been analyzed by sequence analysis of relevant regions of the human said gene from many different individuals. It is a well known fact that genomic DNA of individuals, which harbor the individual genetic makeup of all genes, including the CYP2C8 gene, can easily be purified from individual blood samples. These individual DNA samples are then used for the analysis of the sequence composition of the alleles of the CYP2C8 gene that are present in the individual which provided the blood sample. The sequence analysis was carried out by PCR amplification of relevant regions of said genes, subsequent purification of the PCR products, followed by automated DNA sequencing with established methods (e.g. ABI dye terminator cycle sequencing).

One important parameter that had to be considered in the attempt to determine the individual genotypes and identify novel variants of the CYP2C8 gene by direct DNA-sequencing of PCR-products from human blood genomic DNA is the fact that each human harbors (usually, with very few abnormal exceptions) two gene copies of each autosomal gene (diploidy). Because of that, great care had to be taken in the evaluation of the sequences to be able to identify unambiguously not only homozygous sequence variations but also heterozygous variations. The details of the different steps in the identification and characterization of novel polymorphisms in the CYP2C8 gene (homozygous and heterozygous) are described in the examples below.

Over the past 20 years, genetic heterogeneity has been increasingly recognized as a significant source of variation in drug response. Many scientific communications (Meyer, Ann. Rev. Pharmacol. Toxicol. 37 (1997), 269-296 and West, J. Clin. Pharmacol. 37 (1997), 635-648) have clearly shown that some drugs work better or may even be highly toxic in some patients than in others and that these variations in patient's responses to drugs can be related to molecular basis. This "pharmacogenomic" concept spots correlations between responses to drugs and genetic profiles of patient's (Marshall, Nature Biotechnology, 15 (1997), 954-957; Marshall, Nature Biotechnology, 15 (1997), 1249-1252). In this context of population variability with regard to drug therapy, pharmacogenomics has been proposed as a tool useful in the identification and selection of patients which can respond to a particular drug without side effects. This identification/selection can be based upon molecular diagnosis of genetic polymorphisms by genotyping DNA from leukocytes in the blood of patient, for example, and characterization of disease (Bertz, Clin. Pharmacokinet. 32 (1997), 210-256; Engel, J. Chromatogra. B. Biomed. Appl. 678 (1996), 93-103). For the founders of health care, such as health maintenance organizations in the US and government public health services in many European countries, this pharmacogenomics approach can represent a way of both improving health care and reducing overheads because there is a large cost to unnecessary drugs, ineffective drugs and drugs with side effects.

The mutations in the variant genes of the invention sometime result in amino acid deletion(s), insertion(s) and in particular in substitution(s) either alone or in combination. It is of course also possible to genetically engineer such mutations in wild type genes or other mutant forms. Methods for introducing such modifications in the DNA sequence of said genes are well known to the person skilled in the art; see, e.g., Sambrook, Molecular Cloning A Laboratory Manual, Cold Spring Harbor Laboratory (1989) N.Y.

For the investigation of the nature of the alterations in the amino acid sequence of the polypeptides of the invention may be used such as BRASMOL that are obtainable from the Internet. Furthermore, folding simulations and computer redesign of structural motifs can be performed using other appropriate computer programs (Olszewski, Proteins 25 (1996), 286-299; Hoffman, Comput. Appl. Biosci. 11 (1995), 675-679). Computers can be used for the conformational and energetic analysis of detailed protein models (Monge, J. Mol. Biol. 247 (1995), 995-1012; Renouf, Adv. Exp. Med. Biol. 376 (1995), 37-45). These analysis can be used for the identification of the influence of a particular mutation on metabolizing, binding and/or transport of drugs.

Usually, said amino acid deletion, addition or substitution in the amino acid sequence of the protein encoded by the polynucleotide of the invention is due to one or more nucleotide substitution, insertion or deletion, or any combinations thereof. Preferably said nucleotide substitution, insertion or deletion may result in an amino acid substitution of F to L at position corresponding to position 263 of the CYP2C8 polypeptide (GenBank accession No: GI: 13787189). The polypeptides encoded by the polynucleotides of the invention have altered biological or immunological properties due to the mutations referred to in accordance with the present invention. Examples for said altered properties are stability of the polypeptides which may be effected or an altered substrate specificity or even a complete loss of the capability of metabolizing certain drugs.

The mutations in the CYP2C8 gene detected in accordance with the present invention are listed in Table 2. The methods of the mutation analysis followed standard protocols and are described in detail in the Examples. In general such methods are to be used in accordance with the present invention for evaluating the phenotypic spectrum as well as the overlapping clinical characteristics of diseases or conditions related to dysfunctions or dysregulations and diseases related to the poor or extensive metabolism (PM or EM) certain drugs.

Advantageously, the characterization of said mutants may form the basis of the development of a diagnostic assay that is able to predict a patients efficacy to metabolize a drug for instance in anticancer treatment (TAXOL (paclitaxel)) or cardiovascular deficiencies (verapamil). Said methods encompass for example haplotype analysis, single-strand conformation polymorphism analysis (SSCA), PCR and direct sequencing. On the basis of thorough clinical characterization of many patients the phenotypes can then be correlated to these mutations.

Also comprised by the polynucleotides referred to in the present invention are polynucleotides which comprise at least two of the polynucleotides specified herein above, i.e. polynucleotides having a nucleotide sequence which contains all four mutations comprised by the above polynucleotides or listed in Table 2 below (haplotype: positions 831, 1397 to 1398 of GenBank accession No: AF136830.1, position 270 of GenBank accession No: AF136833.1, and position 206 of (GenBank accession No: AF136842.1). In accordance with the present invention it is also preferred to detect only one of the above mentioned polymorphisms of the haplotype, said one polymorphism being indicative for the presence of the other polymorphisms of the haplotype. Thus, in order to detect the presence of the above mentioned haplotype it is sufficient to determine the presence of any one of the polymorphisms comprised by said haplotype. Moreover, the polynucleotides referred to above allow the study of synergistic effects of said mutations in the CYP2C8 gene and/or a polypeptide encoded by said polynucleotide on the pharmacological profile of drugs in patients who bear such mutant forms of the gene or similar mutant forms that can be mimicked by the above described proteins. It is expected that the analysis of said synergistic effects provides deeper insights into the onset of CYP2C8 dysfunctions or dysregulations or diseases related to altered drug transport as described supra. From said deeper insight the development of diagnostic and pharmaceutical compositions related to CYP2C8 dysfunctions or dysregulations or diseases related to impaired drug metabolism will greatly benefit.

As is evident to the person skilled in the art, the genetic knowledge deduced from the present invention can now be used to exactly and reliably characterize the genotype of a patient. Advantageously, diseases or a prevalence for a disease which are associated with CYP2C8 dysfunction or dysregulation, e.g. diseases associated with arachidonic acid metabolism referred to herein can be predicted and preventive or therapeutical measures can be applied accordingly. Moreover in accordance with the foregoing, in cases where a given drug takes an unusual effect, a suitable individual therapy can be designed based on the knowledge of the individual genetic makeup of a subject with respect to the polynucleotides of the invention and improved therapeutics can be developed as will be further discussed below.

In general, the CYP2C8 "status", defined by the expression level and activity of the CYP2C8 protein, can be variable in normal tissue, due to genetic variations/polymorphisms. The identification of polymorphisms associated with altered CYP2C8 expression and/or activity is important for the prediction of drug metabolism and subsequently for the prediction of therapy outcome, including side effects of medications. Therefore, analysis of CYP2C8 variations indicative of CYP2C8 function, is a valuable tool for therapy with drugs, which are substrates of CYP2C8 and has, thanks to the present invention, now become possible.

In line with the foregoing, preferably, the polynucleotide of the present invention is associated with an incompatibility or a disease related to arachidonic acid metabolism, cancer or cardiovascular diseases.

The term "cancer" used herein is very well known and characterized in the art. Several variants of cancer exist and are comprised by said term as meant in accordance with the invention. For a detailed list of symptoms which are indicative for cancer it is referred to text book knowledge, e.g. Pschyrembel. The term "cardiovascular disease" as used herein refers to those diseases known in the art and described in detail in standard text books, such as Pschyrembel or Stadman. Examples for cardiovascular diseases are hypertension or atherosclerosis. The inefficacy or complete loss to epoxidate arachidonoic acid is referred to as disease of the arachidonic acid metabolism.

In a further embodiment the present invention relates to a polynucleotide which is DNA or RNA.

The polynucleotide of the invention may be, e.g., DNA, cDNA, genomic DNA, RNA or synthetically produced DNA or RNA or a recombinantly produced chimeric nucleic acid molecule comprising any of those polynucleotides either alone or in combination. Preferably said polynucleotide is part of a vector, particularly plasmids, cosmids, viruses and bacteriophages used conventionally in genetic engineering that comprise a polynucleotide of the invention. Such vectors may comprise further genes such as marker genes which allow for the selection of said vector in a suitable host cell and under suitable conditions.

The invention furthermore relates to a gene comprising the polynucleotide of the invention.

It is well known in the art that genes comprise structural elements which encode an amino acid sequence as well as regulatory elements which are involved in the regulation of the expression of said genes. Structural elements are represented by exons which may either encode an amino acid sequence or which may encode for RNA which is not encoding an amino acid sequence but is nevertheless involved in RNA function, e.g. by regulating the stability of the RNA or the nuclear export of the RNA.

Regulatory elements of a gene may comprise promoter elements or enhancer elements both of which could be involved in transcriptional control of gene expression. It is very well known in the art that a promoter is to be found upstream of the structural elements of a gene. Regulatory elements such as enhancer elements, however, can be found distributed over the entire locus of a gene. Said elements could be reside, e.g., in introns, regions of genomic DNA which separate the exons of a gene. Promoter or enhancer elements correspond to polynucleotide fragments which are capable of attracting or binding polypeptides involved in the regulation of the gene comprising said promoter or enhancer elements. For example, polypeptides involved in regulation of said gene comprise the so called transcription factors. Said introns may comprise further regulatory elements which are required for proper gene expression. Introns are usually transcribed together with the exons of a gene resulting in a nascent RNA transcript which contains both, exon and intron sequences. The intron encoded RNA sequences are usually removed by a process known as RNA splicing. However, said process also requires regulatory sequences present on a RNA transcript said regulatory sequences may be encoded by the introns.

In addition, besides their function in transcriptional control and control of proper RNA processing and/or stability, regulatory elements of a gene could be also involved in the control of genetic stability of a gene locus. Said elements control, e.g., recombination events or serve to maintain a certain structure of the DNA or the arrangement of DNA in a chromosome.

Therefore, single nucleotide polymorphisms can occur in exons of a gene which encode an amino acid sequence as discussed supra as well as in regulatory regions which are involved in the above discussed process. The analysis of the nucleotide sequence of a gene locus in its entirety including, e.g., introns is in light of the above desirable. The polymorphisms comprised by the polynucleotides of the present invention can influence the expression level of CYP2C8 protein via mechanisms involving enhanced or reduced transcription of the CYP2C8 gene, stabilization of the gene's RNA transcripts and alteration of the processing of the primary RNA transcripts.

Therefore, in a furthermore preferred embodiment of the gene of the invention a nucleotide deletion, addition and/or substitution results in altered expression of the variant gene compared to the corresponding wild type gene.

In another embodiment the present invention relates to a vector comprising the polynucleotide of the invention or the gene of the invention.

Said vector may be, for example, a phage, plasmid, viral or retroviral vector. Retroviral vectors may be replication competent or replication defective. In the latter case, viral propagation generally will occur only in complementing host/cells.

The polynucleotides or genes of the invention may be joined to a vector containing selectable markers for propagation in a host. Generally, a plasmid vector is introduced in a precipitate such as a calcium phosphate precipitate, or in a complex with a charged lipid or in carbon-based clusters. Should the vector be a virus, it may be packaged in vitro using an appropriate packaging cell line prior to application to host cells.

In a more preferred embodiment of the vector of the invention the polynucleotide is operatively linked to expression control sequences allowing expression in prokaryotic or eukaryotic cells or isolated fractions thereof.

Expression of said polynucleotide comprises transcription of the polynucleotide, preferably into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g., the sac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pCDM8, pRc/CMV, pcDNA1, pcDNA3 (In-vitrogene), pSPORT1 (GIBCO BRL). Preferably, said vector is an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994). Alternatively, the polynucleotides and vectors of the invention can be reconstituted into liposomes for delivery to target cells.

The term "isolated fractions thereof" refers to fractions of eukaryotic or prokaryotic cells or tissues which are capable of transcribing or transcribing and translating RNA from the vector of the invention. Said fractions comprise proteins which are required for transcription of RNA or transcription of RNA and translation of said RNA into a polypeptide. Said isolated fractions may be, e.g., nuclear and cytoplasmic fractions of eukaryotic cells such as of reticulocytes.

The present invention furthermore relates to a host cell genetically engineered with the polynucleotide of the invention, the gene of the invention or the vector of the invention.

Said host cell may be a prokaryotic or eukaryotic cell; see supra. The polynucleotide or vector of the invention which is present in the host cell may either be integrated into the genome of the host cell or it may be maintained extrachromosomally. In this respect, it is also to be understood that the recombinant DNA molecule of the invention can be used for "gene targeting" and/or "gene replacement", for restoring a mutant gene or for creating a mutant gene via homologous recombination; see for example Mouellic, Proc. Natl. Acad. Sci. USA, 87 (1990), 47124716; Joyner, Gene Targeting, A Practical Approach, Oxford University Press.

The host cell can be any prokaryotic or eukaryotic cell, such as a bacterial, insect, fungal, plant, animal, mammalian or, preferably, human cell. Preferred fungal cells are, for example, those of the genus *Saccharomyces*, in particular those of the species *S. cerevisiae*. The term "prokaryotic" is meant to include all bacteria which can be transformed or transfected with a polynucleotide for the expression of a variant polypeptide of the invention. Prokaryotic hosts may include gram negative as well as gram positive bacteria such as, for example, *E. coli*, *S. typhimurium*, *Serratia marcescens* and *Bacillus subtilis*. A polynucleotide coding for a mutant form of variant polypeptides of the invention can be used to transform or transfect the host using any of the techniques commonly known to those of ordinary skill in the art. Methods for preparing fused, operably linked genes and expressing them in bacteria or animal cells are well-known in the art (Sambrook, supra). The genetic constructs and methods described therein can be utilized for expression of variant polypeptides of the invention in, e.g., prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. The transformed prokaryotic hosts can be grown in fermentors and cultured according to techniques known in the art to achieve optimal cell growth. The proteins of the invention can then be isolated from the grown medium, cellular lysates, or cellular membrane fractions. The isolation and purification of the microbially or otherwise expressed polypeptides of the invention may be by any conventional means such as, for example, preparative chromatographic separations and immunological separations such as those involving the use of monoclonal or polyclonal antibodies.

Thus, in a further embodiment the invention relates to a method for producing a molecular variant CYP2CB polypeptide or fragment thereof comprising culturing the above described host cell; and recovering said protein or fragment from the culture.

In another embodiment the present invention relates to a method for producing cells capable of expressing a molecular variant CYP2C8 polypeptide comprising genetically engineering cells with the polynucleotide of the invention, the gene of the invention or the vector of the invention.

The cells obtainable by the method of the invention can be used, for example, to test drugs according to the methods described in D. L. Spector, R. D. Goldman, L. A. Leinwand, Cells, a Lab manual, CSH Press 1998. Furthermore, the cells can be used to study known drugs and unknown derivatives thereof for their ability to complement the deficiency caused by mutations in the CYP2C8 gene. For these embodiments the host cells preferably lack a wild type allele, preferably both alleles of the CYP2C8 gene and/or have at least one mutated from thereof. Ideally, the gene comprising an allele as comprised by the polynucleotides of the invention could be introduced into the wild type locus by homologous replacement. Alternatively, strong overexpression of a mutated allele over the normal allele and comparison with a recombinant cell line overexpressing the normal allele at a similar level may be used as a screening and analysis system. The cells obtainable by the above-described method may also be used for the screening methods referred to herein below.

Furthermore, the invention relates to a polypeptide or fragment thereof encoded by the polynucleotide of the invention, the gene of the invention or obtainable by the method described above or from cells produced by the method described above. In this context it is also understood that the variant polypeptide of the invention can be further modified by conventional methods known in the art. By providing said variant proteins according to the present invention it is also possible to determine the portions relevant for their biological activity or inhibition of the same. The terms "polypeptide" and "protein" as used herein are exchangeable. Moreover, what is comprised by said terms is standard textbook knowledge.

The present invention furthermore relates to an antibody which binds specifically to the polypeptide of the invention.

Advantageously, the antibody specifically recognizes or binds an epitope containing one or more amino acid substitution(s) as defined above. Antibodies against the variant polypeptides of the invention can be prepared by well known methods using a purified protein according to the invention or a (synthetic) fragment derived therefrom as an antigen. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals. In a preferred embodiment of the invention, said antibody is a monoclonal antibody, a polyclonal antibody, a single chain antibody, human or humanized antibody, primatized, chimerized or fragment thereof that specifically binds said peptide or polypeptide also including bispecific antibody, synthetic antibody, antibody fragment, such as Fab, Fv or scFv fragments etc., or a chemically modified derivative of any of these. Furthermore, antibodies or fragments thereof to the aforementioned polypeptides can be obtained by using methods which are described, e.g., in Harlow and Lane "Antibodies, A Laboratory Manual", CSH Press, Cold Spring Harbor, 1988. These antibodies can be used, for example, for the immunoprecipitation and immunolocalization of the variant polypeptides of the invention as well as for the monitoring of the presence of said variant polypeptides, for example, in recombinant organisms, and for the identification of compounds interacting with the proteins according to the invention. For example, surface plasmon resonance as employed in the BIAcore system can be used to increase the efficiency of phage antibodies which bind to an epitope of the protein of the invention (Schier, Human Antibodies Hybridomas 7 (1996), 97-105; Malmborg, J. Immunol. Methods 183 (1995), 7-13).

In a preferred embodiment the antibody of the present invention specifically recognizes an epitope containing one or more amino acid substitution(s) resulting from a nucleotide exchange as defined supra.

Antibodies which specifically recognize modified amino acids such as phospho-Tyrosine residues are well known in the art. Similarly, in accordance with the present invention antibodies which specifically recognize even a single amino acid exchange in an epitope may be generated by the well known methods described supra.

In light of the foregoing, in a more preferred embodiment the antibody of the present invention is monoclonal or polyclonal.

The invention also relates to a transgenic non-human animal comprising at least one polynucleotide of the invention, the gene of the invention or the vector of the invention as described supra.

The present invention also encompasses a method for the production of a transgenic non-human animal comprising introduction of a polynucleotide or vector of the invention into a germ cell, an embryonic cell, stem cell or an egg or a cell derived therefrom. The non-human animal can be used in accordance with the method of the invention described below and may be a non-transgenic healthy animal, or may have a disease or disorder, preferably a disease caused by at least one mutation in the gene of the invention. Such transgenic animals are well suited for, e.g., pharmacological studies of drugs in connection with variant forms of the above described variant polypeptides since these polypeptides or at least their functional domains are conserved between species in higher eukaryotes, particularly in mammals. Production of transgenic embryos and screening of those can be performed, e.g., as described by A. L. Joyner Ed., Gene Targeting, A Practical Approach (1993), Oxford University Press. The DNA of the embryos can be analyzed using, e.g., Southern blots with an appropriate probe or based on PCR techniques. A transgenic non-human animal in accordance with the invention may be a transgenic mouse, rat, hamster, dog, monkey, rabbit, pig, frog, nematode such as *Caenorhabditis elegans*, fruitfly such as *Drosophila melanogaster* or fish such as torpedo fish or zebrafish comprising a polynucleotide or vector of the invention or obtained by the method described above, preferably wherein said polynucleotide or vector is stably integrated into the genome of said non-human animal, preferably such that the presence of said polynucleotide or vector leads to the expression of the variant polypeptide of the invention. It may comprise one or several copies of the same or different polynucleotides or genes of the invention. This animal has numerous utilities, including as a research model for cardiovascular research and therefore, presents a novel and valuable animal in the development of therapies, treatment, etc. for diseases caused by cardiovascular diseases. Accordingly, in this instance, the mammal is preferably a laboratory animal such as a mouse or rat.

Thus, in a preferred embodiment the transgenic non-human animal of the invention is a mouse, a rat or a zebrafish.

Numerous reports revealed that said animals are particularly well suited as model organisms for the investigation of the drug metabolism and its deficiencies or cancer. Advantageously, transgenic animals can be easily created using said model organisms, due to the availability of various suitable techniques well known in the art.

The invention also relates to a solid support comprising one or a plurality of the polynucleotide, the gene, the vector, the polypeptide, the antibody or the host cell of the invention in immobilized form.

The term "solid support" as used herein refers to a flexible or non-flexible support that is suitable for carrying said immobilized targets. Said solid support may be homogenous or inhomogeneous. For example, said solid support may consist of different materials having the same or different properties with respect to flexibility and immobilization, for instance, or said solid support may consist of one material exhibiting a plurality of properties also comprising flexibility and immobilization properties. Said solid support may comprise glass-, polypropylene- or silicon-chips, membranes oligonucleotide-conjugated beads or bead arrays.

The term "immobilized" means that the molecular species of interest is fixed to a solid support, preferably covalently linked thereto. This covalent linkage can be achieved by different means depending on the molecular nature of the molecular species. Moreover, the molecular species may be also fixed on the solid support by electrostatic forces, hydrophobic or hydrophilic interactions or Van-der-Waals forces. The above described physico-chemical interactions typically occur in interactions between molecules. For example, biotinylated polypeptides may be fixed on a avidin-coated solid support due to interactions of the above described types. Further, polypeptides such as antibodies, may be fixed on an antibody coated solid support. Moreover, the immobilization is dependent on the chemical properties of the solid support. For example, the nucleic acid molecules can be immobilized on a membrane by standard techniques such as UV-crosslinking or heat.

In a preferred embodiment of the invention said solid support is a membrane, a glass- or polypropylene- or silicon-chip, are oligonucleotide-conjugated beads or a bead array, which is assembled on an optical filter substrate.

Moreover, the present invention relates to an in vitro method for identifying a polymorphism said method comprising the steps of:

(a) isolating a polynucleotide or the gene of the invention from a plurality of subgroups of individuals, wherein one subgroup has no prevalence for a CYP2C8 associated disease and at least one or more further subgroup(s) do have prevalence for a CYP2C8 associated disease; and
(b) identifying a polymorphism by comparing the nucleic acid sequence of said polynucleotide or said gene of said one subgroup having no prevalence for a CYP2C8 associated disease with said at least one or more further subgroup(s) having a prevalence for a CYP2C8 associated disease.

The term "prevalence" as used herein means that individuals are be susceptible for one or more disease(s) which are associated with CYP2C8 dysfunction or dysregulation or could already have one or more of said disease(s). Thereby, one CYP2C8 associated disease can be used to determine the susceptibility for another CYP2C8 associated disease. Moreover, symptoms which are indicative for a prevalence for developing of a disease are very well known in the art and have been sufficiently described in standard textbooks such as Pschyrembel.

Advantageously, polymorphisms according to the present invention which are associated with CYP2C8 dysfunction or dysregulation or one or more disease(s) based thereon should be enriched in subgroups of individuals which have a prevalence for said diseases versus subgroups which have no prevalence for said diseases. Thus, the above described method allows the rapid and reliable detection of polymorphism which are indicative for one or more CYP2C8 associated disease(s) or a susceptibility therefor. Advantageously, due to the phenotypic preselection a large number of individuals having no prevalence might be screened for polymorphisms in general. Thereby, a reference sequences comprising polymorphisms which do not correlate to one or more CYP2C8 associated disease(s) can be obtained. Based on said reference sequences it is possible to efficiently and reliably determine the relevant polymorphisms.

In a further embodiment the present invention relates to a method for identifying and obtaining a pro-drug or a drug capable of modulating the activity of a molecular variant of a CYP2C8 polypeptide comprising the steps of:

(a) contacting the polypeptide, the solid support of the invention, a cell expressing a molecular variant gene comprising a polynucleotide of the invention, the gene or the vector of the invention in the presence of components capable of providing a detectable signal in response to drug activity with a compound to be screened for pro-drug or drug activity; and
(b) detecting the presence or absence of a signal or increase or decrease of a signal generated from the pro-drug or the drug activity, wherein the absence, presence, increase or decrease of the signal is indicative for a putative pro-drug or drug.

The term "compound" in a method of the invention includes a single substance or a plurality of substances which may or may not be identical.

Said compound(s) may be chemically synthesized or produced via microbial fermentation but can also be comprised in, for example, samples, e.g., cell extracts from, e.g., plants, animals or microorganisms. Furthermore, said compounds may be known in the art but hitherto not known to be useful as an inhibitor, respectively. The plurality of compounds may be, e.g., added to the culture medium or injected into a cell or non-human animal of the invention.

If a sample containing (a) compound(s) is identified in the method of the invention, then it is either possible to isolate the compound from the original sample identified as containing the compound, in question or one can further subdivide the original sample, for example, if it consists of a plurality of different compounds, so as to reduce the number of different substances per sample and repeat the method with the subdivisions of the original sample. It can then be determined whether said sample or compound displays the desired properties, for example, by the methods described herein or in the literature (Spector et al., Cells manual; see supra). Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical. The methods of the present invention can be easily performed and designed by the person skilled in the art, for example in accordance with other cell based assays described in the prior art or by using and modifying the methods as described herein. Furthermore, the person skilled in the art will readily recognize which further compounds may be used in order to perform the methods of the invention, for example, enzymes, if necessary, that convert a certain compound into a precursor. Such adaptation of the method of the invention is well within the skill of the person skilled in the art and can be performed without undue experimentation.

Compounds which can be used in accordance with the present invention include peptides, proteins, nucleic acids, antibodies, small organic compounds, ligands, peptidomimetics, PNAs and the like. Said compounds may act as agonists or antagonists of the invention. Said compounds can also be functional derivatives or analogues of known drugs. Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, New York, USA. Furthermore, said derivatives and analogues can be tested for their effects according to methods known in the art or as described. Furthermore, peptide mimetics and/or computer aided design of appropriate drug derivatives and analogues can be used, for example, according to the methods described below. Such analogs comprise molecules that may have the basis structure of known CYP2C8 substrates, inhibitors and/or modulators.

Appropriate computer programs can be used for the identification of interactive sites of a putative inhibitor and the polypeptides of the invention by computer assistant searches for complementary structural motifs (Fassina, Immunomethods 5 (1994), 114-120). Further appropriate computer systems for the computer aided design of protein and peptides are described in the prior art, for example, in Berry, Biochem. Soc. Trans. 22 (1994), 1033-1036; Wodak, Ann. N.Y. Acad. Sci. 501 (1987), 1-13; Pabo, Biochemistry 25 (1986), 5987-5991. The results obtained from the above-described computer analysis can be used in combination with the method of the invention for, e.g., optimizing known inhibitors, analogs, antagonists or agonists. Appropriate peptidomimetics and other inhibitors can also be identified by the synthesis of peptidomimetic combinatorial libraries through successive chemical modification and testing the resulting compounds, e.g., according to the methods described herein. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715. Furthermore, the three-dimensional and/or crystallographic structure of said compounds and the polypeptides of the invention can be used for the design of peptidomimetic drugs (Rose, Biochemistry 35 (1996), 12933-12944; Rutenber, Bioorg. Med. Chem. 4 (1996), 1545-1558). It is very well known how to obtain said compounds, e.g. by chemical or biochemical standard techniques. Thus, also comprised by the method of the invention are means of making or producing said compounds. In summary, the present invention provides methods for identifying and obtaining compounds which can be used in specific doses for the treatment of specific forms of CYP2C8 associated diseases.

The above definitions apply mutatis mutandis to all of the methods described in the following.

In a further embodiment the present invention relates to a method for identifying and obtaining an inhibitor of the activity of a molecular variant of a CYP2C8 polypeptide comprising the steps of:

(a) contacting the protein, the solid support of the invention or a cell expressing a molecular variant gene comprising a polynucleotide or the gene or the vector of the invention in the presence of components capable of providing a detectable signal in response to drug activity with a compound to be screened for inhibiting activity; and
(b) detecting the presence or absence of a signal or increase or decrease of a signal generated from the inhibiting activity, wherein the absence or decrease of the signal is indicative for a putative inhibitor.

In a preferred embodiment of the method of the invention said cell is a cell, obtained by the method of the invention or can be obtained from the transgenic non-human animal as described supra.

In a still further embodiment the present invention relates to a method of identifying and obtaining a pro-drug or drug capable of modulating the activity of a molecular variant of a CYP2C8 polypeptide comprising the steps of:

(a) contacting the host cell, the cell obtained by the method of the invention, the polypeptide or the solid support of the invention with the first molecule known to be bound by a CYP2C8 polypeptide to form a first complex of said polypeptide and said first molecule;
(b) contacting said first complex with a compound to be screened, and
(c) measuring whether said compound displaces said first molecule from said first complex.

Advantageously, in said method said measuring step comprises measuring the formation of a second complex of said protein and said inhibitor candidate. Preferably, said measuring step comprises measuring the amount of said first molecule that is not bound to said protein.

In a particularly preferred embodiment of the above-described method of said first molecule is a agonist or antagonist or a substrate and/or a inhibitor and/or a modulator of the polypeptide of the invention, e.g., with a radioactive or fluorescent label.

In a still another embodiment the present invention relates to a method of identifying and obtaining an inhibitor capable of modulating the activity of a molecular variant of a CYP2C8 polypeptide comprising the steps of:

(a) contacting the host cell or the cell obtained by the method of the invention, the protein or the solid support of the invention with the first molecule known to be bound by the CYP2C8 polypeptide to form a first complex of said protein and said first molecule;
(b) contacting said first complex with a compound to be screened, and
(c) measuring whether said compound displaces said first molecule from said first complex.

In a preferred embodiment of the method of the invention said measuring step comprises measuring the formation of a second complex of said protein and said compound.

In another preferred embodiment of the method of the invention said measuring step comprises measuring the amount of said first molecule that is not bound to said protein.

In a more preferred embodiment of the method of the invention said first molecule is labeled.

The invention furthermore relates to a method for the production of a pharmaceutical composition comprising the steps of the method as described supra; and the further step of formulating the compound identified and obtained or a derivative thereof in a pharmaceutically acceptable form.

The therapeutically useful compounds identified according to the methods of the invention can be formulated and administered to a patient as discussed above. For uses and therapeutic doses determined to be appropriate by one skilled in the art and for definitions of the term "pharmaceutical composition" see infra.

Furthermore, the present invention encompasses a method for the preparation of a pharmaceutical composition comprising the steps of the above-described methods; and formulating a drug or pro-drug in the form suitable for therapeutic application and preventing or ameliorating the disorder of the subject diagnosed in the method of the invention.

Drugs or pro-drugs after their in vivo administration are metabolized in order to be eliminated either by excretion or by metabolism to one or more active or inactive metabolites (Meyer, J. Pharmacokinet. Biopharm. 24 (1996), 449-459). Thus, rather than using the actual compound or inhibitor identified and obtained in accordance with the methods of the present invention a corresponding formulation as a pro-drug can be used which is converted into its active in the patient. Precautionary measures that may be taken for the application of pro-drugs and drugs are described in the literature; see, for review, Ozama, J. Toxicol. Sci. 21 (1996), 323-329).

In a preferred embodiment of the method of the present invention said drug or prodrug is a derivative of a medicament as defined hereinafter.

The present invention also relates to a method of diagnosing a disorder related to the presence of a molecular variant of the CYP2C8 gene or susceptibility to such a disorder comprising determining the presence of a polynucleotide or the gene of the invention in a sample from a subject.

In accordance with this embodiment of the present invention, the method of testing the status of a disorder or susceptibility to such a disorder can be effected by using a polynucleotide gene or nucleic acid of the invention, e.g., in the form of a Southern or Northern blot or in situ analysis. Said nucleic acid sequence may hybridize to a coding region of either of the genes or to a non-coding region, e.g. intron. In the case that a complementary sequence is employed in the method of the invention, said nucleic acid molecule can again be used in Northern blots. Additionally, said testing can be done in conjunction with an actual blocking, e.g., of the transcription of the gene and thus is expected to have therapeutic relevance. Furthermore, a primer or oligonucleotide can also be used for hybridizing to one of the above mentioned CYP2C8 gene or corresponding mRNAs. The nucleic acids used for hybridization can, of course, be conveniently labeled by incorporating or attaching, e.g., a radioactive or other marker. Such markers are well known in the art. The labeling of said nucleic acid molecules can be effected by conventional methods.

Additionally, the presence or expression of variant CYP2C8 gene can be monitored by using a primer pair that specifically hybridizes to either of the corresponding nucleic acid sequences and by carrying out a PCR reaction according to standard procedures. Specific hybridization of the above mentioned probes or primers preferably occurs at stringent hybridization conditions. The term "stringent hybridization conditions" is well known in the art; see, for example, Sambrook et al., "Molecular Cloning, A Laboratory Manual" second ed., CSH Press, Cold Spring Harbor, 1989; "Nucleic Acid Hybridisation, A Practical Approach", Hames and Higgins eds., IRL Press, Oxford, 1985. Furthermore, the mRNA, cRNA, cDNA or genomic DNA obtained from the subject may be sequenced to identify mutations which may be characteristic fingerprints of mutations in the polynucleotide or the gene of the invention. The present invention further comprises methods wherein such a fingerprint may be generated by RFLPs of DNA or RNA obtained from the subject, optionally the DNA or RNA may be amplified prior to analysis, the methods of which are well known in the art. RNA fingerprints may be performed by, for example, digesting an RNA sample obtained from the subject with a suitable RNA-Enzyme, for example RNase $T_1$, RNase $T_2$ or the like or a ribozyme and, for example, electrophoretically separating and detecting the RNA fragments as described above. Further modifications of the above-mentioned embodiment of the invention can be easily devised by the person skilled in the art, without any undue experimentation from this disclosure; see, e.g., the examples. An additional embodiment of the present invention relates to a method wherein said determination is effected by employing an antibody of the invention or fragment thereof. The antibody used in the method of the invention may be labeled with detectable tags such as a histidine flags or a biotin molecule.

The invention relates to a method of diagnosing a disorder related to the presence of a molecular variant of a CYP2C8 gene or susceptibility to such a disorder comprising determining the presence of a polypeptide or the antibody of the invention in a sample from a subject.

In a preferred embodiment of the above described method said disorder is a cancer or cardiovascular disease.

In a preferred embodiment of the present invention, the above described method is comprising PCR, ligase chain reaction, restriction digestion, direct sequencing, nucleic acid amplification techniques, hybridization techniques or immunoassays. Said techniques are very well known in the art.

Moreover, the invention relates to a method of detection of the polynucleotide or the gene of the invention in a sample comprising the steps of (a) contacting the solid support described supra with the sample under conditions allowing interaction of the polynucleotide or the gene of the invention with the immobilized targets on a solid support and;

(b) determining the binding of said polynucleotide or said gene to said immobilized targets on a solid support.

The invention also relates to an in vitro method for diagnosing a disease comprising the steps of the method described supra, wherein binding of said polynucleotide or gene to said immobilized targets on said solid support is indicative for the presence or the absence of said disease or a prevalence for said disease.

The invention furthermore relates to a diagnostic composition comprising the polynucleotide, the gene, the vector, the polypeptide or the antibody of the invention.

In addition, the invention relates to a pharmaceutical composition comprising the polynucleotide, the gene, the vector, the polypeptide or the antibody of the invention. These pharmaceutical compositions comprising, e.g., the antibody may conveniently be administered by any of the routes conventionally used for drug administration, for instance, orally, topically, parenterally or by inhalation. Acceptable salts comprise acetate, methylester, HCl, sulfate, chloride and the like. The compounds may be administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment.

Furthermore, the use of pharmaceutical compositions which comprise antisense-oligonucleotides which specifically hybridize to RNA encoding mutated versions of the polynucleotide or gene according to the invention or which comprise antibodies specifically recognizing a mutated polypeptide of the invention but not or not substantially the functional wild-type form is conceivable in cases in which the concentration of the mutated form in the cells should be reduced.

In another embodiment the present invention relates to the use of the polynucleotide, the gene, the vector, the polypeptide, the polynucleotides having at a position corresponding to position 270 (exon 3) and 206 (exon 8) (GenBank accession No: AF136833.1 and AF136842.1, respectively) of the CYP2C8 gene (GenBank accession No: GI: 13787189) an A instead of a G in position 270 and a G instead of an A in position 206, or the antibody of the invention for the preparation of a diagnostic composition for diagnosing a disease.

Thanks to the present invention the particular drug selection, dosage regimen and corresponding patients to be treated can be determined in accordance with the present invention. The dosing recommendations will be indicated in product labeling by allowing the prescriber to anticipate dose adjustments depending on the considered patient group, with information that avoids prescribing the wrong drug to the wrong patients or at the wrong dose.

In a further embodiment the present invention relates to the use of the polynucleotide, the gene, the vector, the polypeptide, the polynucleotides having at a position corresponding to position 117 in exon 5 (GenBank accession No: AF136837.1) of the CYP2C8 gene (GenBank accession No: GI: 13787189) a T instead of an A, or the antibody of the invention for the preparation of a pharmaceutical composition for treating a disease.

In a more preferred embodiment of the use of the present invention said disease is an incompatibility or disease related to arachidonic acid metabolism, cancer or cardiovascular disease.

Finally, the present invention relates to a diagnostic kit for detection of a single nucleotide polymorphism comprising the polynucleotide, the gene, the vector, the polypeptide, the antibody, the host cell, the transgenic non-human animal or the solid support of the invention.

The kit of the invention may contain further ingredients such as selection markers and components for selective media suitable for the generation of transgenic cells and animals. The kit of the invention can be used for carrying out a method of the invention and could be, inter alia, employed in a variety of applications, e.g., in the diagnostic field or as research tool. The parts of the kit of the invention can be packaged individually in vials or other appropriate means depending on the respective ingredient or in combination in suitable containers or multicontainer units. Manufacture of the kit follows preferably standard procedures which are known to the person skilled in the art. The kit may be used for methods for detecting expression of a mutant form of the polypeptides, genes or polynucleotides in accordance with any one of the above-described methods of the invention, employing, for example, immunoassay techniques such as radio-immunoassay or enzyme-immunoassay or preferably nucleic acid hybridization and/or amplification techniques such as those described herein before and in the Examples as well as pharmacokinetic studies when using non-human transgenic animals of the invention.

The invention will now be described by reference to the following biological Examples which are merely illustrative and are not constructed as a limitation of the scope of the present invention.

EXAMPLES

Example 1

Isolation of Genomic DNA from Human Blood, Generation and Purification of CYP2C8 Gene Fragments Genomic DNA was obtained by standard ion exchange chromatography techniques (Qiagen kits for isolation of genomic DNA from blood). Blood from all the individuals tested (volunteers from Parexel, Berlin and the Institute for Clinical Pharmacology, Stuttgart) was obtained under consideration of all legal, medical and bureaucratical requirements. Further samples from other ethnic populations (e.g. Caucasian, Japanese, African-American) were purchased from commercial sources.

By using polymerase chain reaction (PCR) with specific oligonucleotide primers, two for each fragment, defined DNA-fragments containing specific parts of the human CYP2C8 gene were obtained. These specific oligonucleotide primers were designed to bind to sequences upstream and downstream of the various exons as well as in the 5 prime region of the CYP2C8 gene. The resulting DNA fragments did not contain codogenic parts alone but also sequences covering the intronic parts located at the exon-intron boundaries. These sites are known to be important for correct processing and subsequent expression of the protein encoding mRNA, a process called "splicing". Commercially synthesized oligonucleotide primer pairs that were purified by affinity chromatography were optimized for each of the 9 exon and 4 promoter fragments of the human CYP2C8 gene. The sequences for each primer are listed in table 1.

Polymerase chain reactions were performed under conditions that were optimized for each of the nine fragments and a promoter region covering about 2 kb upstream of the initiation codon for mRNA translation. PCRs were carried out for all exons in a volume of 50 μl. 10-50 ng of template DNA were added to standard PCR-buffer containing 1.5 mM $MgCl_2$, 200 μM dNTPs and 1 U Taq-polymerase (all from Qiagen, Hilden) as well as 10-40 pMol of primers (MWG Biotech, Munich). All PCR reactions were performed on identical conditions at a Perkin Elmer thermocycler (Modell 9700) with an initial denaturation step of 94° C. for 2 min, followed by 34 cycles for PCR-fragment generation with 45 s denaturation at 94° C., 45 s of annealing at 62° C. and 1 min at 72° C. for elongation. The exact location of the primers and size of the desired fragments are also listed in table 1.

The defined DNA fragments containing specific parts of the CYP2C8 gene, exon as well as some intron sequences at the inton-exon boundaries were processed to remove nonincorporated nucleotides and buffer components that might otherwise interfere with the subsequent determination of the individual CYP2C8 genotype by direct cycle sequencing. For this purification, standard ion exchange chromatography techniques were used (Qiagen kits for PCR-fragment purification). For all fragments sufficient yields of purified fragments, suitable for direct DNA sequencing analysis were obtained. Aliquots of purified fragments were subjected to direct sequence analysis of the CYP2C8 gene in an ABI 3700 capillary sequencer.

Example 2

Identification of Different CYP2C8 Alleles by Sequence Determination in Various Individuals For sequence analysis of relevant regions of the human CYP2C8 gene from many different individuals, PCR amplifications of the relevant regions of the gene were carried out (pimers see table 1) following purification of the PCR products and sequencing with established methods (ABI dye terminator cycle sequencing). Since the individual genetic makeup is represented by two copies of any gene (diploidy), great care has to be taken in the evaluation of the sequences not to unambiguously identify homozygous, but also heterozygous sequence variation. Therefore, in cases where no clear discrimination could be detected, forward and reverse sequencing was performed. Moreover, for the discovery of complete and defined alleles, e.g. in linkage equilibrium, it is necessary to cover all exons as well as the promoter region to provide a comprehensive basis for the phenotype prediction of individual SNPs.

For the evaluation of CYP2C8 variations in the human population, sequence analyses of the relevant regions, including a 2 kb pormoter fragment and all exons of the gene were carried out from genomic DNA of each 48 Caucasian, Japanese and African-American individuals. The sequences were subjected to a computer analysis programme (Phredphrap™, Perkin Elmer) and inspected manually for the occurrence of DNA sequences deviating from recently published CYP2C8 sequences that were considered to represent the “wild type” sequences in this work.

Because population genetics enables a calculation of the expected frequency of homozygous vs. heterozygous alleles of a defined gene (Hardy Weinberg formula: 2p e2+2pq+2q e2=1), it was possible to confirm predicted distributions of homozygous vs. heterozygous alleles and deviations from the experimental findings. This serves as experimental control that a detected sequence variation indeed represents a novel allele.

Several new CYP2C8 sequence variations were discovered and experimentally confirmed using this approach which are shown in table 2. 18 polymorphisms are located in the 5' untranslated region/promoter of the gene (GenBank accession No: AF136830.1). 22 new polymorphisms could be found in sequences of introns 1, 2, 3, 4 and 8 (GenBank accession Nos: AF136832.1, AF136833.1, AF136835.1 AF136843.1 and AF136844.1) and one in the 3' untranslated region of the gene (GenBank accession No: AF136845.1).

Furthermore, three particular nucleotide changes in exon 3 (position 334 at exon/intron boundary, GenBank accession No: 163833.1) and exon 8 (position 30 and 87, GenBank accession No: AF1368.43.1) were detected that do not change the amino acid sequence. In exon 3 (position 329, GenBank accession No: AF136833.1), exon 4 (position 243, GenBank accession No: AF136842.2 and position 13 of GenBank accession No: AF136835.1), exon 5 (position 42, 101 and 104, GenBank accession No: AF136837.1), exon 6 (position 309, GenBank accession No: AF136838.1) and 7 (position 1135, GenBank accession No: NM_000770.1 and position 232, GenBank accession No: AF136840.1) nine SNPs could be identified that change the protein sequence as shown in table 4, where the deviative amino acid is typed in a bold style. These novel, and already published CYP2C8 SNPs serve as markers for the characterization of the CYP2C8 status in patients.

The positions of the novel CYP2C8 SNPs, including the exact novel sequence context are listed in table 2. The deviative base in the sequence is typed underlined and in a bold style.

Example 3

Figure 4:
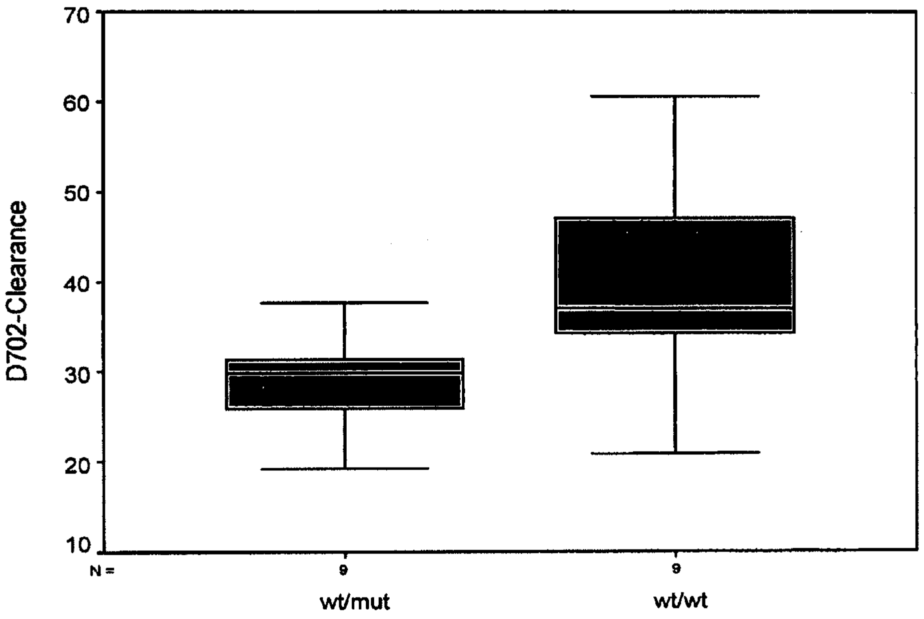

Determination of the CYP2C8 Promoter Allele Containing G-1207A, delAT −640 to −641 as a Pharmacogenetic Factor Influencing Drug Levels The anticancer drug TAXOL (paclitaxel) can be considered to be the prototype for CYP2C8 and it's isoform 6-hydroxypaclitaxel as diagnostic substrate. Furthermore, verapamil represents another specific substrate for CYP2C8 that is methylated to different metabolites, e.g D-702 and D-703 or desalkylated to D-617 (i.e. a substrate of CYP3A4). The generation of a specific metabolite used to selectively proof the functional activity of CYP2C8 (LC-MS) is shown in FIG. 4. In parallel, the amount of enzyme is determined by western blotting (see example 9).

Using these analytical tools, phenotypically characterized samples that have been treated with TAXOL (paclitaxel) (N=22) or verapamil (N=15, 44) were subjected to genotyping. Either of the collectives showed that two SNPs G-1207A, delAT-640 to −641 of the 5' untranslated region are in linkage disequilibrium and, in combination with SNPs G270A (exon 3) and A206G (exon 8), represent a new allele (haplotype) that is mainly defined by the presence of the two novel promoter SNPs G-1207A and delAT-640 to −641. FIG. 4 shows that this allele is responsible for the reduced level of metabolized substrate.

Example 4

Functional Consequences of the Identification of CYP2C8 Promoter Polymorphisms The eukaryotic promoter region of a gene is composed of several regulatory elements, e.g enhancer, silencer and other responsive elements. Here, single nucleotide polymorphisms exhibit significant influence. Regarding cytochrome P450-enzymes induction mechanisms, e.g. transcription factors like C/EBP, HPFs or barbiebox-sites identified in CYP2C9 (Klose, J Biochem Mol Toxicol 13 (1999), 289-95) are important since temporary expression is required. SNPs change or interfere with such elements and can alter promoter action and/or transcription activity. The novel SNP identified at position −1207 most probably abolishes transcription factor binding that has selectively been shown for the binding of tissue specific sterol regulatory element binding protein 1 (SREBP-1, Valleft, J Biol. Chem. 271 (1996), 12247-53). Reduced expression has been shown if position −1207 does not correspond to the wild type. The correlation of this new allele with CYP2C8 enzyme activity is displayed in FIG. 4. The linkage with another unidentified SNPs further downstream in the promoter region of CYP2C8 (delAT −640 to −641) confers new value to the allele in respect to diagnostic applications.

Example 5

Figure 3:
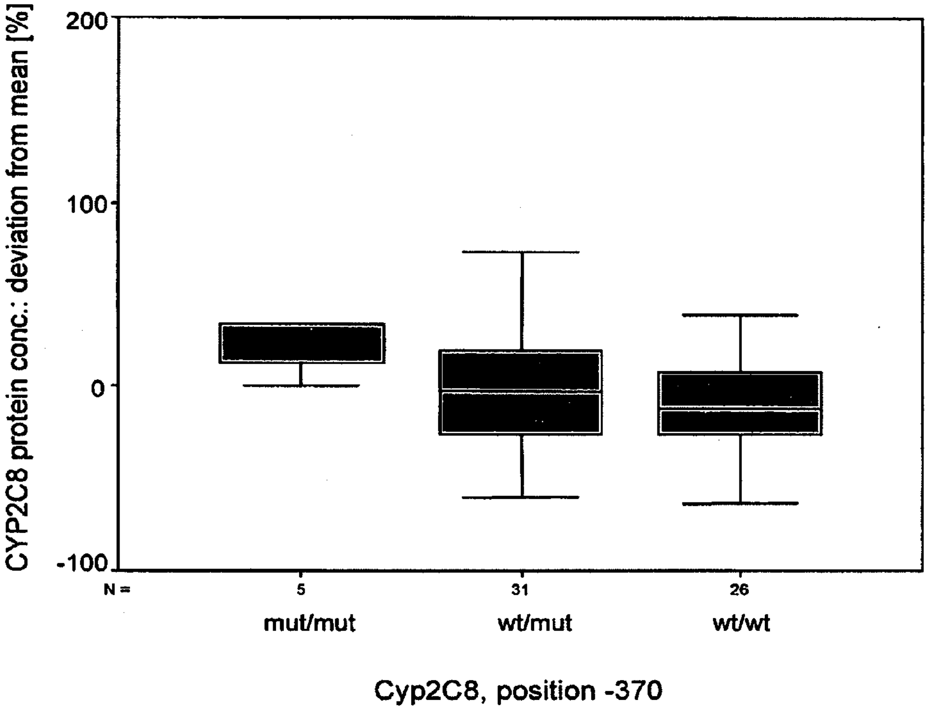

Determination of the CYP2C8 Promoter Polymorphism T-370G as a Pharmacogenetic Factor Influencing Drug Levels Another polymorphism located further downstream at position 1668 in the 5-prime untranslated region (position −370 relative to the ATG-start codon) could be identified to significantly increase the expression level as shown in FIG. 3. This allele refers to as an extensive metabolizing phenotype (EM) that was confirmed by investigation of phenotypically characterized samples. In several cases, single nucleotide polymorphisms G-1207A, delAT −640 to −641 occur in combination with T-370G. LC-MS results from these samples show that individuals carrying the T-370G alone have an increased CYP2C8-activity as compared to those heterozygous for the polymorphisms G-1207A, delAT −640 to −641 allele. Concerning the application in a diagnostic assay these data clearly show the influence of position T-370G on the expression levels of CYP2C8, i.e. the latter SNP is responsible for a change from poor (PM) to intermediate/extensive metabolism (IM/EM) as demonstrated in example 9/table 6.

Figure 2:
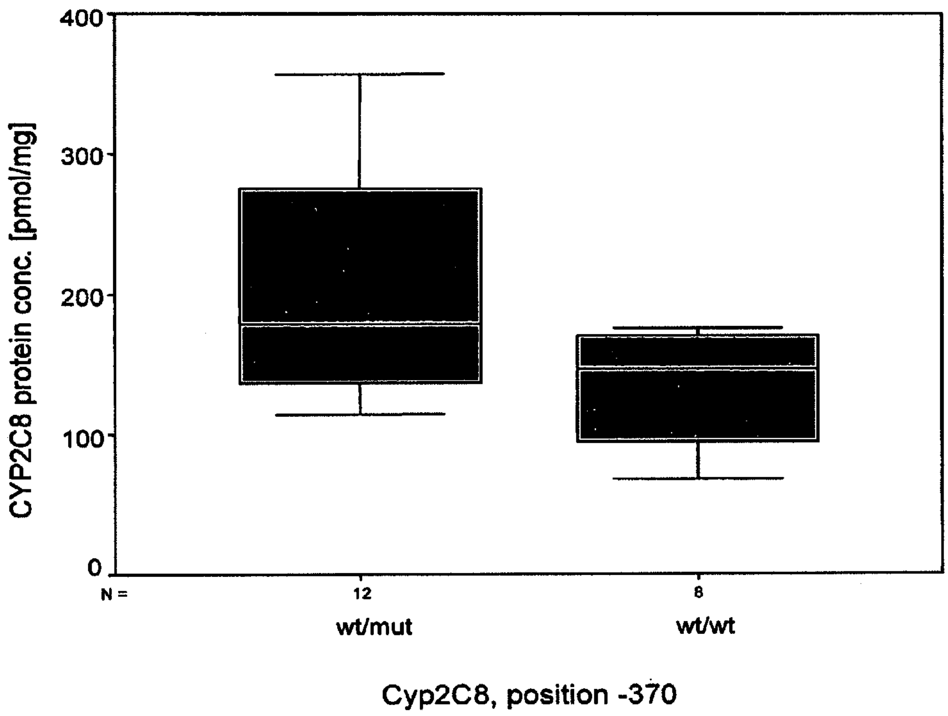

Independently, a further validation was carried out by genotyping 22 samples corresponding to individual liver extracts, in which the metabolism of TAXOL (paclitaxel) was assessed. The data confirm results as presented in examples 8 and 9. FIG. 2 shows the significant correlation between a heterogeneous polymorphism at position −370G and the increase of CYP2C8 protein levels. The liver extract from a sample homogeneous for position −370 displayed the highest CYP2C8-protein level (>400 pmol/mg protein). This is an additional independent result that supports the significant correlation in FIG. 2.

Example 6

Determination of the CYP2C8 Polymorphism at Amino Acid Position 264 (Exon 5) as a Pharmacogenetic Factor Influencing Drug Levels In another embodiment the present invention relates to a polymorphism in exon 5 at position C104G (GenBank accession No: AF136837.1). This change correlates with a reduced protein concentration analyzed from genotyped samples (FIG. 1) that could be due to less stable mRNA or protein. The polypeptides encoded by the polynucleotides of the invention may have altered biological or immunological properties due to the polymorphisms referred to in accordance with the present invention. Examples for said altered properties are stability of the polypeptides which may be effected or the incapability to effectively metabolize certain drugs.

Example 7

Using Restriction Fragment Length Polymorphism (RFLP) Analysis to Detect SNPs Relevant in Phenotypic Prediction CYP2C8-polymorphisms can be detected not only by sequencing but also by various other means. As one alternative to the sequencing methodology, genotyping can be performed with PCR fragments to be processed by one restriction endonuclease specifically cutting at a region, composed of a unique sequence of 4-6 nucleotides. Due to the limited length of a PCR-fragment sometimes advantage can be taken of this specificity if it discriminates mutant and wild type, i.e. resulting in digested or un digested fragments (Table 5). Regarding the present invention this was the case for fragments of the promoter region 4 (position −370, double cutter AcsI for wild type and single cutter in the mutant), that indicates the respective allele, exon 3 (position 275, single cutter SapI for CYP2C8-mutant), and exon 5 (position 104, single cutter ClaI for wild type). Depending of the fragments' specific SNP-region the restriction pattern unambiguously reflects either the wild type, the heterozygous or homozygous mutant. As defined by the primers listed in table 1, the exons screened for result in the following RFLP-fragments:

TABLE 5

| SNP position | | Length (bp) | Genotype | | |
|---|---|---|---|---|---|
| (PCR-fragment) | Enzyme | uncut | wt/wt (bp) | wt/mut (bp) | mut/mut (bp) |
| # −370, (5'UTR) | Acs1 | 483 | 33/150/300 | 33/150/183/300 | 183/300 |
| # 270, (exon 3) | Sapl | 328 | 328 | 149/179/328 | 149/179 |
| # 104, (exon 5) | Clal | 584 | 192/392 | 192/392/584 | 584 |

Example 7

Identification of New CYP2C8 Polymorphisms by Sequence Analysis of a Collection of Various Individuals from Different Ethnic Groups The screen for SNPs in the CYP2C8 gene in the genomes of different ethnic groups yielded a number of polymorphisms listed in table 2. 48 samples were analyzed from each of the ethnic populations Caucasian, Japanese and African-American, respectively. Within this collection, the large number of SNPs in the untranslated region could be considered to potentially influence the protein level.

Furthermore, several polymorphisms show extensive inter ethnical discrepancies (Table 3) between various ethnical groups. The 57 new polymorphisms identified in the CYP2C8 gene will complement the existing knowledge and contribute to a more comprehensive understanding of the gene, avoiding problems in drug response and, concerning other ethnical groups, thus facilitating "bridging studies" that could be of interest when projecting data from these embodiment.

Example 8

Figure 5:
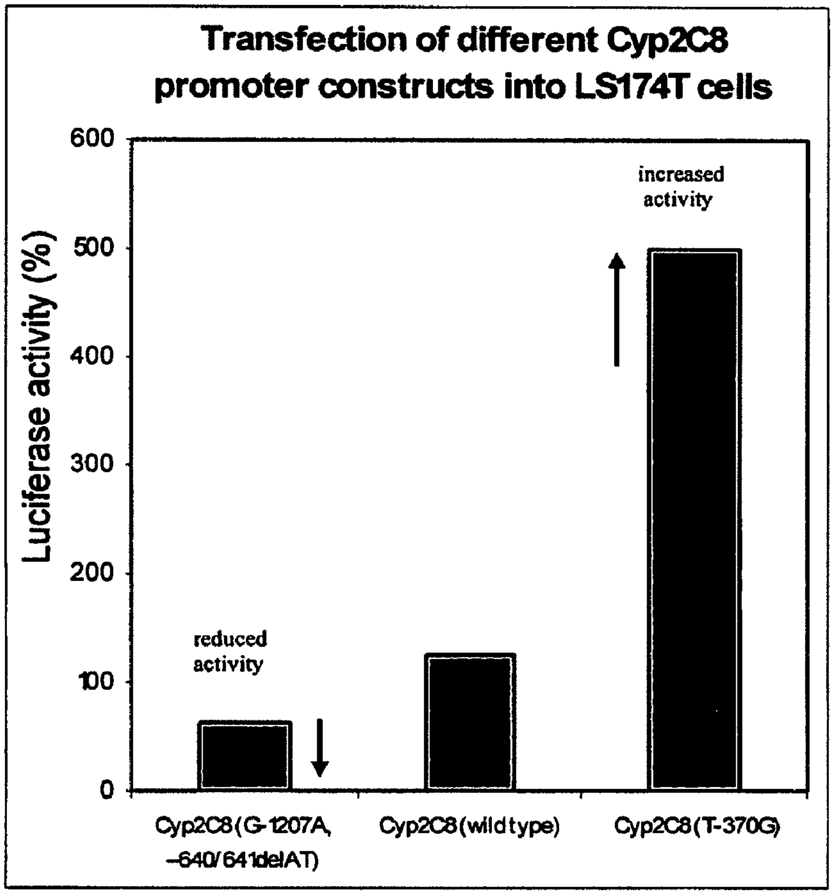

Characterization of Promoter SNPs by Transfection of Promoter-Reporter Plasmids into Human Cells Three promoter SNPs were tested for their contribution to different expression levels by transfection assays using the LS174T cell line. Promoter fragments containing the wild type or the SNPs at positions corresponding to positions G-1207A and delAT −640 to −641 (GenBank accession No: AF136830.1) or at position corresponding to position T-370G (GenBank accession No: AF136830.1) were introduced into a commercial mammalian expression vector. The plasmid harbours standard sequences for the propagation in eukaryotic cells including the reporter gene luciferase that is controlled by the integrated promoter sequence. Following sequence verification of each DNA-insert, cells were cotransfected with β-galactosidase, harvested after 48 h and analysed for luciferase activity. Promoter activities (%) are shown in FIG. 5 following normalization to the transfection efficacy as determined by β-galactosidase detection. The data are in full agreement with the observations from phenotypically characterized samples. A DNA-construct that contains the 1207G>A and −640 to −641 delAT polymorphisms (FIG. 5) showed decreased transcription for the CYP2C8-promoter levels compared to the wild type. In contast, the reporter plasmid revealed increasing levels of luciferase protein under control of a CYP2C8-promoter containing a polymorphism corresponding to position −370.

Example 9

Protein Quantification of Samples Containing SNPs at Promoter Position G-1207A, delAT −640 to −641, T-370G and C104G (exon 5, amino acid Position 264) of CYP2C8

Protein extracts have been prepared from human liver samples. The protein levels of CYP2C8 were analysed by western blot using samples genotyped for SNPs G-1207A, delAT −640 to −641, T-370G (all GenBank accession No: AF136830.1) and C104G (GenBank accession No: AF136837.1). Table 5 shows the effects of different genotypes on the expression levels of CYP2C8 (pmol/mg) normalized for the wild type (=100%). Results are in total agreement with the functional data described by the promoter-reporter assays in example 8. The promoter SNP in position T-370G confers to increased levels of the CYP2C8 protein (150%), whereas polymorphisms G-1207A and delAT −640 to −641 in contrast show a reduced protein expression (72%). In combination with SNPs G-1207A and delAT −640 to −641, or C104G alone the polymorphism T-370G differentially influences protein levels as indicated by arrow. Here, the presence of two SNPs with significant frequency leads to combined effects. Therefore, considerations for reliable phenotype prediction as a result from genotyping must depend on multiple SNP-analyses. The data indicate that the SNP in position −370, which by itself is responsible for up regulation of the CYP2C8-protein level, shows no significant CYP2C8 increase if it is combined with SNPs G-1207A and delAT −640 to −641 (5'UTR), which by themselves reduce the expression. The combined expression level of 119% is barely higher than in the homozygous wildtype situation. Vice versa, in combination with the C104G allele (exon 5) the increased expression due to the SNP at position −370 is compensated by the SNP C104G to normal expression levels (97%) compared to the wild type. This reflects the strong impact of SNP C104G alone on the protein level (see FIG. 1). The SNP C104G therefore represents an allele for down regulation.

TABLE 6

| Genotype (by detection of listed SNPs) | CYP 2C8-levels (%) | Effects |
|---|---|---|
| Wild type | 100 | No |
| G-1207A, delAT −640 to −641 (5'UTR) | 72 | ↓ |
| T-370G (5'UTR) | 150 | ↑ |
| G-1207A, delAT −640 to −641 and T-370G (5'UTR) | 119 | ↑↓ |
| T-370G (5'UTR) and aa I264M (exon 5) | 97 | ↑↓ |

No sample with aa change I264M or G-1207A, delAT −640 to −641 (5'UTR) and I264M was detected.

Example 10

Pharmacogenetic Relevance of the CYP2C8 Polymorphisms at Position 329 (exon 3, Thr 159 Pro), 309 (exon 6, Glu 274 stop) and 1135 (exon 7, Gly 365 Ser)

Figure 6:
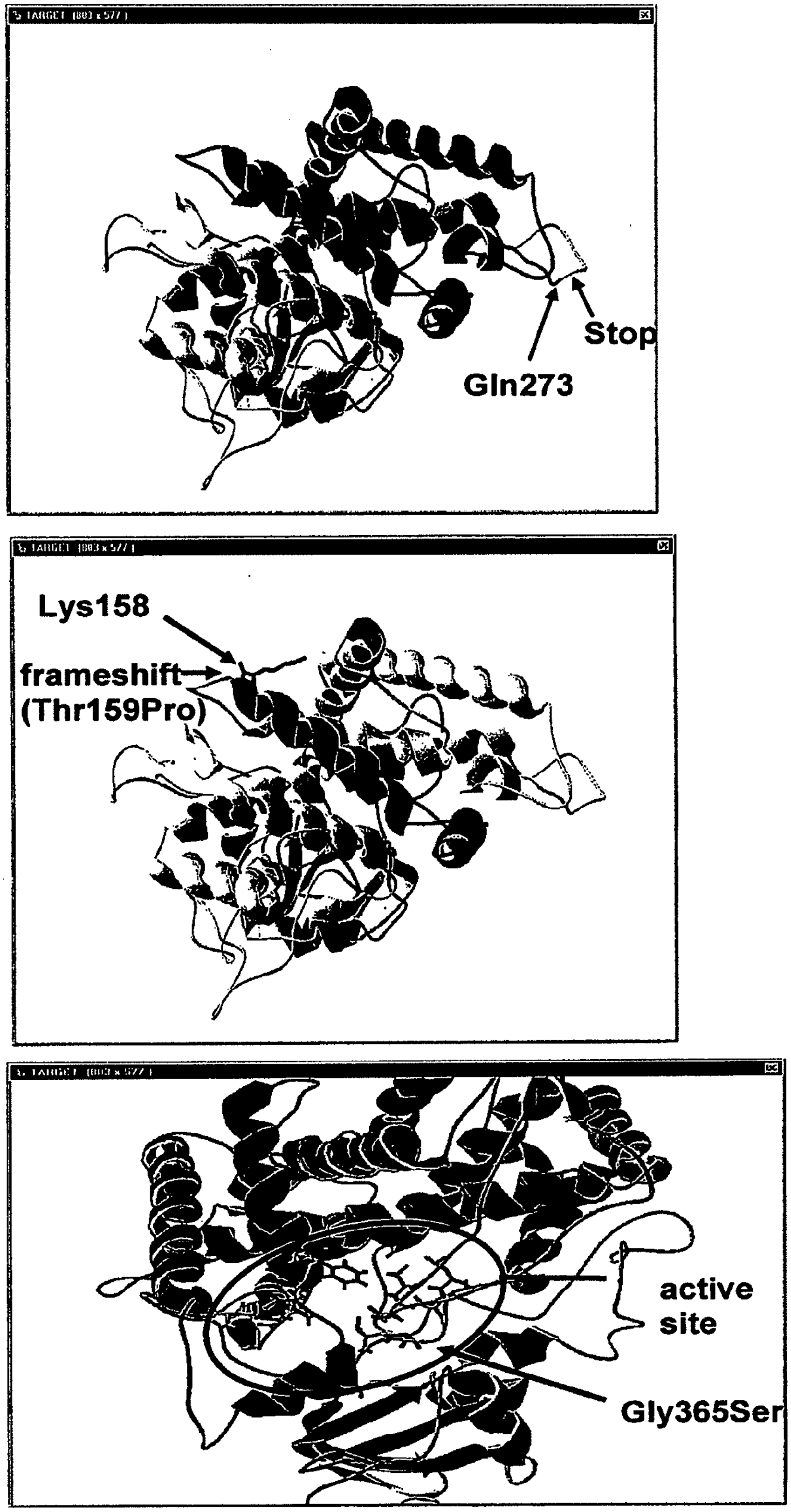

In another embodiment the present invention relates to a polymorphisms in exon 3, exon 6 and 7 at positions 329 (GenBank accession No: AF136833.1), 309 (GenBank accession No: AF136838.1) rand 1135 (GenBank accession No: NM_000770.1) respectively. The delA change in position 329 causes a frameshift abolishing the C-terminal part of the protein. The G309T change in position 309 results in a premature termination at amino acid position 274 of the protein. Both variant transcripts encode for polypeptides that will loose their function and are therefore most likely poor metabolizer alleles (FIG. 6). In another embodiment the present invention relates to a polymorphism at position G1135A in exon 7 (GenBank accession No: NM_000770.1). This substitution results in a change from Glycin to Serin at position 365 within the active site of the CYP2C8 enzyme (FIG. 6). Because the active site of wildtype CYP2C8 contains hydrophobic amino acids to enable the hydrohpilic substrate to efficiently enter the substrate pocket, this amino acid exchange to a hydrophilic residue will severely interfere with substrate binding and subsequent metabolism.

Table 1 Primer sequences for the generation of CYP2C8 PCR-fragments (SEQ ID NOS: 25-51, respectively, in order of appearance)

TABLE 1

Primer sequences for the generation of CYP2C8 PCR-fragments (SEQ ID NOS: 25-51, respectively, in order of appearance) All primer locations refer to different contigs of HTGS-Database, GenBank Acc. No. AL359672.10 PCR-fragments at the 5'UTR are overlapping.

| PCR-fragment name | PCR-fragm. size (bp) | Contig spec. exon location | Primer position | | Primer Sequence (5' - 3') |
|---|---|---|---|---|---|
| Contig | | 115244-120972 (5629 bp) | | | |
| 5'UTR Fragm. 1 | 537 | 534 | 120439-120416 | forward: | ATT TTA GTC AAT CTT GGT GGC CCG |
| | | | 119902-119926 | reverse: | TTC AAC AGA AGA TGG AAC ACA GGG A |
| 5'UTR Fragm. 2 | 545 | | 120004-119980 | forward: | TCA TGA CCA TTG ACT ATC AGT TCC C |
| | | | 119460-119483 | reverse: | TGA TAC CCA TTG GGG TTC ATT ACC |
| 5'UTR Fragm. 3 | 751 | | 119576-119552 | forward: | AAC AGA GTC AAG GTG GCG TAT CTT C |
| | | | 118826-118854 | reverse: | CAA TAT TCT CAG ATT AAT GAC CAG TTG GG |
| Sequencing primer | | | 118938-118963 | | AGA CTT AGC CCT TGA TAA CAA AAG CC |
| 5'UTR Fragm. 4 | 483 | -2486 | 119008-118982 | forward: | GTT TAG GCA GCT GTA TTT TAA GTG AAC |
| | | | 118526-118550 | reverse: | ACT CCA AAG TTT TTA TAA CAC TCC C |
| Exon 1 | 472 | 2487-2654 | 118687-118664 | forward: | GGC ACT GGA AAG AAG GAG TAG GAC |
| | | | 118216-118242 | reverse: | GAT CTA TTA TAA TAG TGT GCT TCC AGG |
| Exon 2 | 457 | 4198-4360 | 116999-116978 | forward: | TTG TGT ACC AAT TGC CTG GGT C |
| | | | 116543-116566 | reverse: | TTT TTA GGG CTC TGT TTT CCA TCC |
| Exon 3 | 328 | 4532-4681 | 116531-116508 | forward: | GAG CTT AGC CTA TCT GCA TGG CTG |
| | | | 116204-116223 | reverse: | ACC TGG CCA CCC CTG AAA TG |
| Contig | | 78619-85206 (6588 bp) | | | |
| Exon 4 Alternative | 541 | 1378-1538 AF136834.2 | 83947-83970 44-67 | forward: | TCC ATG CTG ATT TTT TTT GGA CAC |
| | | | 83429-83450 | reverse: | CTG ACC CCT TGC ACT TCT GAT G |
| Contig | | 138518-143654 (5137 bp) | | | |
| Exon 5 | 583 | 1319-1495 | 139593-139617 | forward: | TGA CGA GTT ATT GGG TGC AGT ACA C |
| | | | 140176-140154 | reverse: | TTC CAT GAT GTT TAG TGC AGG CC |
| Contig | | 85307-115243 (29937 bp) | | | |
| Exon 6 | 519 | 8875-9016 | 93884-93903 | forward: | TTG AAG TAA GAC AGG GCA TCG G |
| | | | 94402-93379 | reverse: | AGA AAC AAG GTG GAG GAT ACT GGC |
| Exon 7 | 328 | 11749-11936 | 96986-97009 | forward: | GGC CAT GAA TTG CTA TGA CAA ATG |
| | | | 97313-97290 | reverse: | GGT TGG AAC CAA ACC AGC ACT ATG |
| Exon 8 | 462 | 15788-15929 | 100976-100997 | forward: | CTG GCT GGA CCT GAG TTT CCT C |
| | | | 101437-101418 | reverse: | TTA ACT CCT GCA AGC CCC GC |
| Exon 9/3'UTR | 543 | 17526-17707 | 102630-102652 | forward: | GTA CAT TTG TTT GTC CCA CCA TCC |
| | | | 103172-103149 | reverse: | TGC AGT GAC CTG AAC AAC TCT CCT |

Table 2 SNPs identified in the CYP2C8 gene (SEQ ID NOS: 52-213, 382-387, 214-303, 388-393, 304-309, 394-399 and 310-375, respectively, in order of appearance)

TABLE 2

SNPs identified in the CYP2C8 gene (SEQ ID NOS: 52-213, 382-387, 214-303, 388-393, 304-309, 394-399 and 310-375, respectively, in order of appearance

| PCR-fragm Location | GenBank Acc. No | variant position (relative to ATG) | wild type (f) and (r) | wild type/mutant (f) and (r) | mutant/mutant (f) and (r) |
|---|---|---|---|---|---|
| 5'UTR-fragm 1 | AF136830.1 | #306 to 307 (= -1731 to -1732) | f:GATGTGATG**AG**TGTGAAAAT<br>r:ATTTTCACA**CT**CATCACATC | f:GATGTGATG(**AG**)TGTGAAAAT<br>r:ATTTTCACA(**CT**)CATCACATC | f:GATGTGATGTGTGAAAAT<br>r:ATTTTCACACATCACATC |
| 5'UTR-fragm 1 | AF136830.1 | #411 = -1627) | f:GGAAATAAC**T**GTACTGGTC<br>r:GACCAGTAC**A**GTTATTTCC | f:GGAAATAAC**T/A**GTACTGGTC<br>r:GACCAGTAC**A/T**GTTATTTCC | f:GGAAATAAC**A**GTACTGGTC<br>r:GACCAGTAC**T**GTTATTTCC |
| 5'UTR-fragm 1 | AF136830.1 | #560 (= -1478) | f:GGTCTGCAC**A**TTGCAGTGG<br>r:CCACTGCAA**T**GTGCAGACC | f:GGTCTGCAC**A/G**TTGCAGTGG<br>r:CCACTGCAA**C/T**GTGCAGACC | f:GGTCTGCAC**G**TTGCAGTGG<br>r:CCACTGCAA**C**GTGCAGACC |
| 5'UTR-fragm 2 | AF136830.1 | #713 (-1325) | f:AAAACAATA**G**AAGCAGCCA<br>r:TGGCTGCTT**C**TATTGTTTT | f:AAAACAATA**G/T**AAGCAGCCA<br>r:TGGCTGCTT**A/C**TATTGTTTT | f:AAAACAATA**T**AAGCAGCCA<br>r:TGGCTGCTT**A**TATTGTTTT |
| 5' UTR-fragm 2 | AF136830.1 | #817 (= -1221) | f:AGTGCTGAA**C**AACTTTCAC<br>r:GTGAAAGTT**G**TTCAGCACT | f:AGTGCTGAA**C/A**AACTTTCAC<br>r:GTGAAAGTT**T/G**TTCAGCACT | f:AGTGCTGAA**A**AACTTTCAC<br>r:GTGAAAGTT**T**TTCAGCACT |
| 5'UTR-fragm 2 | AF136830.1 | #824 (= -1214) | f:AACAACTTT**C**ACTTGTGAG<br>r:CTCACAAGT**G**AAAGTTGTT | f:AACAACTTT**C/A**ACTTGTGAG<br>r:CTCACAAGT**T/G**AAAGTTGTT | f:AACAACTTT**A**ACTTGTGAG<br>r:CTCACAAGT**T**AAAGTTGTT |
| 5'UTR-fragm 2 | AF136830.1 | #831 (= -1207) | f:TTCACTTGT**G**AGGTGATGC<br>r:GCATCACCT**C**ACAAGTGAA | f:TTCACTTGT**G/A**AGGTGATGC<br>r:GCATCACCT**T/C**ACAAGTGAA | f:TTCACTTGT**A**AGGTGATGC<br>r:GCATCACCT**T**ACAAGTGAA |
| 5'UTR-fragm 2 | AF136830.1 | #879 (= -1159) | f:CTTTTGAGC**G**TCTCCGGTC<br>r:GACCGGAGA**C**GCTCAAAAG | f:CTTTTGAGC**G/A**TCTCCGGTC<br>r:GACCGGAGA**T/C**GCTCAAAAG | f:CTTTTGAGC**A**TCTCCGGTC<br>r:GACCGGAGA**T**GCTCAAAAG |
| 5'UTR-fragm 2 | AF136830.1 | 886 (= -1152) | f:GCGTCTCCG**G**TCCTCTTAT<br>r:ATAAGAGGA**C**CGGAGACGC | f:GCGTCTCCG**G/T**TCCTCTTAT<br>r:ATAAGAGGA**A/C**CGGAGACGC | f:GCGTCTCCG**T**TCCTCTTAT<br>r:ATAAGAGGA**A**CGGAGACGC |
| 5'UTR-fragm 3 | AF136830.1 | #1058 = -980) | f:ACCCCAATG**G**GTATCAGAA<br>r:TTCTGATAC**C**CATTGGGGT | f:ACCCCAATG**G/A**GTATCAGAA<br>r:TTCTGATAC**T/C**CATTGGGGT | f:ACCCCAATG**A**GTATCAGAA<br>r:TTCTGATAC**T**CATTGGGGT |
| 5'UTR-fragm 3 | AF136830.1 | #1271 to 1273 (= -765) to (-767) | f:GTATTTATG**TTA**TTATTATGT<br>r:ACATAATAA**TAA**CATAAATAC | f:GTATTTATG(**TTA**) TTATTATGT<br>r:ACATAATAA(**TAA**) CATAAATAC | f:GTATTTATGTTATTATGT<br>r:ACATAATAACATAAATAC |
| 5'UTR-fragm 3 | AF136830.1 | #1397 to 1398 (= -640) to (-641) | f:TGTAATAAC**AT**ATATATTTA<br>r:TAAATATAT**AT**GTTATTACA | f:TGTAATAAC(**AT**)ATATATTTA<br>r:TAAATATAT(**AT**)GTTATTACA | f:TGTAATAACATATATTTA<br>r:TAAATATATGTTATTACA |
| 5'UTR-fragm 4 | AF136830.1 | #1627 (= -411) | f:TTTTTTATA**T**ACAAAATAT<br>r:ATATTTTGT**A**TATAAAAAA | f:TTTTTTATA**T/C**ACAAAATAT<br>r:ATATTTTGT**G/A**TATAAAAAA | f:TTTPTTATA**C**ACAAAATAT<br>r:ATATTTTGT**G**TATAAAAAA |
| 5'UTR-fragm 4 | AF136830.1 | #1668 (= -370) | f:GGTCATAAA**T**TCCCAACTG<br>r:CAGTTGGGA**A**TTTATGACC | f:GGTCATAAA**T/G**TCCCAACTG<br>r:CAGTTGGGA**C/A**TTTATGACC | f:GGTCATAAA**G**TCCCAACTG<br>r:CAGTTGGGA**C**TTTATGACC |
| 5'UTR-fragm 4 | AF136830.1 | #1767 = -271) | f:ACATTGGAA**C**AACCAGGGA<br>r:TCCCTGGTT**G**TTCCAATGT | f:ACATTGGAA**C/A**AACCAGGGA<br>r:TCCCTGGTT**T/G**TTCCAATGT | f:ACATTGGAA**A**AACCAGGGA<br>r:TCCCTGGTT**T**TTCCAATGT |
| 5'UTR-fragm 4 | AF136830.1 | #1785/1786 (= -252) | f:AATTAAAAATACCTGGGC<br>r:GCCCAGGTATTTTTAATT | f:AATTAAAAA(**A**)TACCTGGGC<br>r:GCCCAGGTA(**T**)TTTTTAATT | f:AATTAAAAA**A**TACCTGGGC<br>r:GCCCAGGTA**T**TTTTTAATT |
| 5'UTR-fragm 4 | AF136830.1 | #1887 (= -151) | f:CTATCCATG**G**GCCAAAGTC<br>r:GACTTTGGC**C**CATGGATAG | f:CTATCCATG**G/A**GCCAAAGTC<br>r:GACTTTGGC**T/C**CATGGATAG | f:CTATCCATG**A**GCCAAAGTC<br>r:GACTTTGGC**T**CATGGATAG |
| 5'UTR-fragm 4 | AF136830.1 | #1905 (= -133) | f:CCACTCAGA**A**AAAAAGTAT<br>r:ATACTTTTT**T**TCTGAGTGG | f:CCACTCAGA**A/C**AAAAAGTAT<br>r:ATACTTTTT**G/T**TCTGAGTGG | f:CCACTCAGA**C**AAAAAGTAT<br>r:ATACTTTTT**G**TCTGAGTGG |
| 5'UTR-fragm 4 | AF136830.1 | #1952 (= -86) | f:ACATGTCAA**A**GAGACACAC<br>r:GTGTGTCTC**T**TTGACATGT | f:ACATGTCAA**A/C**GAGACACAC<br>r:GTGTGTCTC**G/T**TTGACATGT | f:ACATGTCAA**C**GAGACACAC<br>r:GTGTGTCTC**G**TTGACATGT |
| Intron 1 | AF136832.1 | #171 | f:ATTCAGAAA**T**ATCGAATCT<br>r:AGATTCGAT**A**TTTCTGAAT | f:ATTCAGAAA**T/C**ATCGAATCT<br>r:AGATTCGAT**G/A**TTTCTGAAT | f:ATTCAGAAA**C**ATCGAATCT<br>r:AGATTCGAT**G**TTTCTGAAT |
| Intron 1 | AF136832.1 | #258 | f:AGCAAATAG**C**GACTTATTT<br>r:AAATAAGTC**G**CTATTTGCT | f:AGCAAATAG**C/T**GACTTATTT<br>r:AAATAAGTC**A/G**CTATTTGCT | f:AGCAAATAG**T**GACTTATTT<br>r:AAATAAGTC**A**CTATTTGCT |
| Intron 2 | AF136833.1 | #122 | f:ATGGCTGCC**G**AGTGTTGCA<br>r:TGCAACACT**C**GGCAGCCAT | f:ATGGCTGCC**G/A**AGTGTTGCA<br>r:TGCAACACT**T/C**GGCAGCCAT | f:ATGGCTGCC**A**AGTGTTGCA<br>r:TGCAACACT**T**GGCAGCCAT |
| Intron 2 | AF136833.1 | #150 | f:TCCTTGGCT**G**TGAATTCTC<br>r:GAGAATTCA**C**AGCCAAGGA | f:TCCTTGGCT**G/A**TGAATTCTC<br>r:GAGAATTCA**T/C**AGCCAAGGA | f:TCCTTGGCT**A**TGAATTCTC<br>r:GAGAATTCA**T**AGCCAAGGA |
| Intron 2 | AF136833.1 | #180/181 | f:CCTTTTTTTATTAGGAAT<br>r:ATTCCTAATAAAAAAAGG | f:CCTTTTTTT(**T**)ATTAGGAAT<br>r:ATTCCTAAT(**A**)AAAAAAAGG | f:CCTTTTTTT**T**ATTAGGAAT<br>r:ATTCCTAAT**A**AAAAAAAGG |
| Intron 2 | AF136833.1 | #182 | f:CTTTTTTTA**T**TAGGAATCA<br>r:TGATTCCTA**A**TAAAAAAAG | f:CTTTTTTTA**T/C**TAGGAATCA<br>r:TGATTCCTA**G/A**TAAAAAAAG | f:CTTTTTTTA**C**TAGGAATCA<br>r:TGATTCCTA**G**TAAAAAAAG |
| Exon 3 | AF136833.1 | #270 | f:TGGGGAAGA**G**GAGCATTGA<br>r:TCAATGCTC**C**TCTTCCCCA | f:TCGGGAAGA**G/A**GAGCATTGA<br>r:TCAATGCTC**T/C**TCTTCCCCA | f:TGGGGAAGA**A**GAGCATTGA<br>r:TCAATGCTC**T**TCTTCCCCA |
| Exon 3 | AF136833.1 | #334 | f:AAAAACCAA**G**GGTGGGTGA<br>r:TCACCCACC**C**TTGGTTTTT | f:AAAAACCAA**G/A**GGTGGGTGA<br>r:TCACCCACC**T/C**TTGGTTTTT | f:AAAAACCAA**A**GGTGGGTGA<br>r:TCACCCACC**T**TTGGTTTTT |
| Exon 3 | AF136833.1 | #329 | f:TTGAGAAAA**A**CCAAGGGTG<br>r:CACCCTTGG**T**TTTTCTCAA | f:TTGAGAAAA(**A**)CCAAGGGTG<br>r:CACCCTTGG(**T**)TTTTCTCAA | f:TTGAGAAAACCAAGGGTG<br>r:CACCCTTGGTTTTCTCAA |
| Intron 3 | AF136833.1 | #378 | f:CAGTTACCT**G**TCTTCACTA<br>r:TAGTGAAGA**C**AGGTAACTG | f:CAGTTACCT**G/C**TCTTCACTA<br>r:TAGTGAAGA**G/C**AGGTAACTG | f:CAGTTACCT**C**TCTTCACTA<br>r:TAGTGAAGA**G**AGGTAACTG |
| Intron 3 | AF136834.2 | #87 | f:TGTAAGATA**T**GTTTAAAAT<br>r:ATTTTAAAC**A**TATCTTACA | f:TGTAAGATA(**T**)GTTTAAAAT<br>r:ATTTTAAAC(**A**)TATCTTACA | f:TGTAAGATAGTTTAAAAT<br>r:ATTTTAAACTATCTTACA |
| Intron 3 | AF136834.2 | #162 | f:ATAATTTTT**T**TAAAAATTT<br>r:AAATTTTTA**A**AAAAATTAT | f:ATAATTTTT**T/A**TAAAAATTT<br>r:AAATTTTTA**T/A**AAAAATTAT | f:ATAATTTTT**A**TAAAAATTT<br>r:AAATTTTTA**T**AAAAATTAT |
| Intron 3 | AF136834.2 | #163 | f:TAATTTTTT**T**AAAAATTTT<br>r:AAAATTTTT**A**AAAAAATTA | f:TAATTTTTT**T/A**AAAAATTTT<br>r:AAAATTTTT**T/A**AAAAAATTA | f:TAATTTTTT**A**AAAAATTTT<br>r:AAAATTTTT**T**AAAAAATTA |

TABLE 2-continued

SNPs identified in the CYP2C8 gene (SEQ ID NOS: 52-213, 382-387, 214-303, 388-393, 304-309, 394-399 and 310-375, respectively, in order of appearance

| PCR-fragm Location | GenBank Acc. No | variant position (relative to ATG) | wild type (f) and (r) | wild type/mutant (f) and (r) | mutant/mutant (f) and (r) |
|---|---|---|---|---|---|
| Exon 4 | AF136834.2 | #243 | f:ATCTGCTCCGTTGTTTTCC | f:ATCTGCTCCG/ATTGTTTTCC | f:ATCTGCTCCATTGTTTTCC |
| | NM_000770.1 | #583 | r:GGAAAACAACGGAGCAGAT | r:GGAAAACAAT/CGGAGCAGAT | r:GGAAAACAATGGAGCAGAT |
| Exon 4 | AF136835.1 | #13 | f:GGATTCTGAACTCCCCATG | f:GGATTCTGAA/GCTCCCCATG | f:GGATTCTGAGCTCCCCATG |
| | | | r:CATGGGGAGTTCAGAATCC | r:CATGGGGAGC/TTCAGAATCC | r:CATGGGGAGCTCAGAATCC |
| Intron 4 | AF136835.1 | #180 | f:TGATTTCCTGTTCAAAATT | f:TGATTTCCTG/ATTCAAAATT | f:TGATTTCCTATTCAAAATT |
| | | | r:AATTTTGAACAGGAAATCA | r:AATTTTGAAT/CAGGAAATCA | r:AATTTTGAATAGGAAATCA |
| Intron 4 | AF136836.1 | #116 | f:ACTTAAAGTATAATAAAAA | f:ACTTAAAGTA/GTAATAAAAA | f:ACTTAAAGTGTAATAAAAA |
| | | | r:TTTTTATTATACTTTAAGT | r:TTTTTATTAC/TACTTTAAGT | r:TTTTTATTACACTTTAAGT |
| Intron 4 | AF136836.1 | #132 | f:AAAATGTATATATGTATAA | f:AAAATGTATA/GTATGTATAA | f:AAAATGTATGTATGTATAA |
| | | | r:TTATACATATATACATTTT | r:TTATACATAC/TATACATTTT | r:TTATACATACATACATTTT |
| Intron 4 | AF136836.1 | #172 | f:ATGATGTCTTATTCATATT | f:ATGATGTCTT/CATTCATATT | f:ATGATGTCTCATTCATATT |
| | | | r:AATATGAATAAGACATCAT | r:AATATGAATG/AAGACATCAT | r:AATATGAATGAGACATCAT |
| Intron 4 | AF136836.1 | #189 | f:TTTATAGTTATAATTTCAA | f:TTTATAGTTA/GTAATTTCAA | f:TTTATAGTTGTAATTTCAA |
| | | | r:TTGAAATTATAACTATAAA | r:TTGAAATTAC/TAACTATAAA | r:TTGAAATTACAACTATAAA |
| Exon 5 | AF136837.1 | #42 | f:CGAAGTTACATTAGGGAGA | f:CGAAGTTACA/GTTAGGGAGA | f:CGAAGTTACGTTAGGGAGA |
| | | | r:TCTCCCTAATGTAACTTCG | r:TCTCCCTAAC/TGTAACTTCG | r:TCTCCCTAACGTAACTTCG |
| Exon 5 | AF136837.1 | #101 | f:TCGGGACTTTATCGATTGC | f:TCGGGACTTT/GATCGATTGC | f:TCGGGACTTGATCGATTGC |
| | | | r:GCAATCGATAAAGTCCCGA | r:GCAATCGATC/AAAGTCCCGA | r:GCAATCGATCAAGTCCCGA |
| Exon 5 | AF136837.1 | #104 | f:GGACTTTATCGATTGCTTC | f:GGACTTTATC/GGATTGCTTC | f:GGACTTTATGGATTGCTTC |
| | | | r:GAAGCAATCGATAAAGTCC | r:GAAGCAATCC/GATAAAGTCC | r:GAAGCAATCCATAAAGTCC |
| Exon 5 | AF136837.1 | #117 | f:TGCTTCCTGATCAAAATGG | f:TGCTTCCTGA/TTCAAAATGG | f:TGCTTCCTGTTCAAAATGG |
| | | | r:CCATTTTGATCAGGAAGCA | r:CCATTTTGAA/TCAGGAAGCA | r:CCATTTTGAACAGGAAGCA |
| Exon6 | AF136838.1 | #309 | f:CACTTCTAGGAAAAGGACA | f:CACTTCTAGG/TAAAAGGACA | f:CACTTCTAGTAAAAGGACA |
| | | | r:TGTCCTTTTCCTAGTTGTG | r:TGTCCTTTTC/ACTAGTTGTG | r:TGTCCTTTTACTAGTTGTG |
| Exon 7 | NM_000770.1 | #1135 | f:GTCCCCACCGGTGTGCCCC | f:GTCCCCACCG/AGTGTGCCCC | f:GTCCCCACCAGTGTGCCCC |
| | | | r:GGGGCACACCGGTGGGGAC | r:GGGGCACACT/CGGTGGGGAC | r:GGGGCACACTGGTOGGGAC |
| Exon 7 | AF136840.1 | #232 | f:AGGATAGGAGCCACATGCC | f:AGGATAGGAG/TCCACATGCC | f:AGGATAGGATCCACATGCC |
| | | | r:GGCATGTGGCTCCTATCCT | r:GGCATGTGGA/CTCCTATCCT | f:GGCATGTGGATCCTATCCT |
| Exon 8 | AF136842.1 | #206 | f:ATGATGACAAAGAATTTCC | f:ATGATGACAA/GAGAATTTCC | f:ATGATGACAGAGAATTTCC |
| | | | r:GGAAATTCTTTGTCATCAT | r:GGAAATTCTC/TTGTCATCAT | r:GGAAATTCTCTGTCATCAT |
| Exon 8 | AF136843.1 | #30 | f:TGACCCTGGCCACTTTCTA | f:TGACCCTGGC/TCACTTTCTA | f:TGACCCTGGTCACTTTCTA |
| | | | r:TAGAAAGTGGCCAGGGTCA | r:TAGAAAGTGA/GCCAGGGTCA | r:TAGAAAGTGACCAGGGTCA |
| Exon 8 | AF136843.1 | #87 | f:GCCTTTCTCAGCAGGTAAT | f:GCCTTTCTCA/GGCAGGTAAT | f:GCCTTTCTCGGCAGGTAAT |
| | | | r:ATTACCTGCTGAGAAAGGC | r:ATTACCTGCC/TGAGAAAGGC | r:ATTACCTGCCGAGAAAGGC |
| Intron 8 | AF136843.1 | #167 | f:TACATGGCACCTCCTCTGG | f:TACATGGCAC/ACTCCTCTGG | f:TACATGGCAACTCCTCTGG |
| | | | r:CCAGAGGAGGTGCCATGTA | r:CCAGAGGAGT/GTGCCATGTA | r:CCAGAGGAGTTGCCATGTA |
| Intron 8 | AF136843.1 | #197 | f:TTGCTATTTGTCCATGATC | f:TTGCTATTTG/ATCCATGATC | f:TTGCTATTTATCCATGATC |
| | | | r:GATCATGGACAAATAGCAA | r:GATCATGGAT/CAAATAGCAA | r:GATCATGGATAAATAGCAA |
| Intron 8 | AF136843.1 | #212 | f:GATCAAGAGCACCACTCTT | f:GATCAAGAGC/TACCACTCTT | f:GATCAAGAGTACCACTCTT |
| | | | r:AAGAGTGGTGCTCTTGATC | r:AAGAGTGGTA/TCTCTTGATC | r:AAGAGTGGTACTCTTGATC |
| Intron 8 | AF136843.1 | #221 | f:CACCACTCTTAACACCCAT | f:CACCACTCTT/CAACACCCAT | f:CACCACTCTCAACACCCAT |
| | | | r:ATGGGTGTTAAGAGTGGTG | r:ATGGGTGTTG/AAGAGTGGTG | r:ATGGGTGTTGAGAGTGGTG |
| Intron 8 | AF136843.1 | #255 | f:AATACACCATCATTATTGG | f:AATACACCAT/CCATTATTGG | f:AATACACCACCATTATTGG |
| | | | r:CCAATAATGATGGTGTATT | r:CCAATAATGG/ATGGTGTATT | r:CCAATAATGGTGGTGTATT |
| Intron 8 | AF136843.1 | #271 | f:TGGGCCAGATAGCGGGGCT | f:TGGGCCAGAT/CAGCGGGGCT | f:TGGGCCAGACAGCGGGGCT |
| | | | r:AGCCCCGCTATCTGGCCCA | r:AGCCCCGCTG/ATCTGGCCCA | r:AGCCCCGCTGTCTGGCCCA |
| Intron 8 | AF136844. 1 | #118 | f:TTATTTACTGCATATTCTG | f:TTATTTACTG/ACATATTCTG | f:TTATTTACTACATATTCTG |
| | | | r:CAGAATATGCAGTAAATAA | r:CAGAATATGA/GAGTAAATAA | r:CAGAATATGTAGTAAATAA |
| 3 UTR | AF136845.1 | #44 | f:TCTGGCTGCCGATCTGCTA | f:TCTGGCTGCC/TGATCTGCTA | f:TCTGGCTGCTGATCTGCTA |
| | | | r:TAGCAGATCGGCAGCCAGA | r:TAGCAGATCA/GGCAGCCAGA | r:TAGCAGATCAGCAGCCAGA |

TABLE 3

Comparison of allelic frequencies (%) from the populations analyzed (calculation based on Hardy-Weinberg law).

| SNP (−: rel. to ATG) (GenBank Acc. No ref. to, s. text) | Caucasian | Japanese | African-American | Location |
|---|---|---|---|---|
| (−1731)-(−1732) | 1.3 | n.d. | 11.7 | 5'UTR |
| −1627 | n.d. | n.d. | 16.6 | 5'UTR |
| −1478 | n.d. | n.d. | 2 | 5'UTR |
| −1325 | n.d. | n.d. | 1.4 | 5'UTR |
| −1221 | n.d. | 1.6 | n.d. | 5'UTR |
| −1214 | 4.3 | n.d. | n.d. | 5'UTR |
| −1207 | 13.5 | n.d. | 3.75 | 5'UTR |
| −1159 | n.d. | n.d. | 1.1 | 5'UTR |

TABLE 3-continued

Comparison of allelic frequencies (%) from the populations analyzed (calculation based on Hardy-Weinberg law).

| SNP (−: rel. to ATG) (GenBank Acc. No ref. to, s. text) | Caucasian | Japanese | African-American | Location |
|---|---|---|---|---|
| −1152 | 3.05 | n.d. | n.d. | 5'UTR |
| −980 | n.d. | n.d. | 1.2 | 5'UTR |
| (−765)-(−767) | n.d. | n.d. | n.d. | 5'UTR |
| (−640)-(−641) | 10.35 | n.d. | 4.5 | 5'UTR |
| −411 | 14 | 37.8 | 17.4 | 5'UTR |
| −370 | 19.2 | 29.7 | 3.2 | 5'UTR |
| −271 | 23.3 | 5.7 | 3.2 | 5'UTR |
| −248 | n.d. | n.d. | 3.2 | 5'UTR |

TABLE 3-continued

| Comparison of allelic frequencies (%) from the populations analyzed (calculation based on Hardy-Weinberg law). | | | | |
|---|---|---|---|---|
| SNP (−: rel. to ATG) (GenBank Acc. No ref. to, s. text) | Caucasian | Japanese | African-American | Location |
| −151 | n.d. | n.d. | 1.6 | 5'UTR |
| −133 | n.d. | n.d. | 2.2 | 5'UTR |
| −86 | n.d. | n.d. | 1.2 | 5'UTR |
| 171 | 1.4 | n.d. | n.d. | Intron 1 |
| 258 | n.d. | n.d. | 1.6 | Intron 1 |
| 122* | | | | Intron 2 |
| 150 | n.d. | n.d. | 11.6 | Intron 2 |
| 180-181 | 30.8 | 51.1 | 47.8 | Intron 2 |
| 182 | n.d. | n.d. | 2.3 | Intron 2 |
| 270 | 12 | n.d. | 4.5 | Exon 3 |
| 334 | n.d. | n.d. | 15.9 | Exon 3 |
| 378 | 14.6 | n.d. | 4.5 | Intron 3 |
| 87 | 6.1 | 1.3 | 3.2 | Intron 3 |
| 162 | 1.2 | n.d. | n.d. | Intron 3 |
| 163 | 24.2 | 2.6 | 25.8 | Intron 3 |
| 243§ | | | | Exon 4 |
| 13 | n.d. | n.d. | 1.6 | Exon 4 |
| 180 | 24.4 | 1.2 | 26.4 | Intron 4 |
| 116 | 29.6 | 46.4 | 7.4 | Intron 4 |
| 132 | 4.7 | n.d. | 7.4 | Intron 4 |
| 172 | 24.6 | 51.2 | 24.1 | Intron 4 |
| 189 | 2.6 | n.d. | n.d. | Intron 4 |
| 42 | n.d. | n.d. | 1.9 | Exon 5 |
| 101 | n.d. | 1.1 | n.d. | Exon 5 |
| 104 | 5 | n.d. | 1.7 | Exon 5 |
| 117 | n.d. | n.d. | 14.2 | Exon 5 |
| 1135 | n.d. | n.d. | 1.2 | Exon 7 |
| 206 | 11.4 | n.d. | 3.2 | Exon 8 |
| 30 | n.d. | 7.3 | n.d. | Exon 8 |
| 87 | n.d. | n.d. | 2.17 | Exon 8 |
| 167 | 6.3 | n.d. | 5.6 | Intron 8 |
| 197 | 23 | 51.2 | 41.1 | Intron 8 |
| 212 | 1.3 | n.d. | n.d. | Intron 8 |
| 221 | n.d. | 3.7 | n.d. | Intron 8 |
| 255 | n.d. | n.d. | 1.1 | Intron 8 |
| 271 | 2.1 | n.d. | 1.7 | Intron 8 |
| 118 | 26.4 | n.d. | 44.4 | Intron 8 |
| 44 | 22.3 | 53 | n.d. | 3'UTR |

*has been detected in a sample of a pre-screen (Caucasian sample).
§has been detected in a phenotyped sample (Caucasian sample).
n.d. - not detect in the samples analyzed.

Table 4 Listing of all amino acid changes in the coding regions (SEQ ID NOS: 1-2, 376-377, 3-16, 378-379, 17-18, 380-381 and 19-24, respectively, in order of appearance)

TABLE 4

| Listing of all amino acid changes in the coding regions | | |
|---|---|---|
| Met Gly Lys **Arg** Ser Ile Glu | s001.txt | Exon 3 |
| Met Gly Lys **Lys** Ser Ile Glu | s002.txt | |
| Glu Leu Arg Lys **Thr Lys Ala** | s376.txt | Exon 3/4 |
| Glu Leu Arg Lys **Pro Arg Leu** | s377.txt | |
| Arg Lys Thr **Lys** Ala Ser Pro | s003.txt | Exon 3/4 |
| Arg Lys Thr **Lys** Ala Ser Pro | s004.txt | |
| Ile Cys Ser **Val** Val Phe Gln | s005.txt | Exon 3 |
| Ile Cys Ser **Ile** Val Phe Gln | s006.txt | |
| Ala Ile Leu **Asn** Ser Pro Trp | s007.txt | Exon 4 |
| Ala Ile Leu **Ser** Ser Pro Trp | s008.txt | |
| Arg Ser Tyr **Ile** Arg Glu Lys | s009.txt | Exon 5 |
| Arg Ser Tyr **Val** Arg Glu Lys | s010.txt | |
| Pro Arg Asp **Phe** Ile Asp Cys | s011.txt | Exon 5 |
| Pro Arg Asp **Leu** Ile Asp Cys | s012.txt | |
| Arg Asp Phe **Ile** Asp Cys Phe | s013.txt | Exon 5 |
| Arg Asp Phe **Met** Asp Cys Phe | s014.txt | |
| Cys Phe Leu **Ile** Lys Met Glu | s015.txt | Exon 5 |
| Cys Phe Leu **Phe** Lys Met Glu | s016.txt | |
| Met Glu Gln **Glu** Lys Asp Asn | s378.txt | Exon 6 |
| Met Glu Gln **STOP** | s379.txt | |
| Val Pro Thr **Gly** Val Pro His | s017.txt | Exon 7 |
| Val Pro Thr **Ser** Val Pro His | s018.txt | |
| Gln Asp Arg **Ser** His Met Pro | s380.txt | Exon 7 |
| Gln Asp Arg **Ile** His Met Pro | s381.txt | |
| His Asp Asp **Lys** Glu Phe Pro | s019.txt | Exon 8 |
| His Asp Asp **Arg** Glu Phe Pro | s020.txt | |
| Phe Asp Pro **Gly** His Phe Leu | s021.txt | Exon 8 |
| Phe Asp Pro **Gly** His Phe Leu | s022.txt | |
| Met Pro Phe **Ser** Ala Gly Lys | s023.txt | Exon 8 |
| Met Pro Phe **Ser** Ala Gly Lys | s024.txt | |

The invention claimed is:

1. An in vitro method for determining whether a human subject is at risk for increased metabolism of a CYP2C8 substrate comprising the step of:

(a) detecting in a CYP2C8 polynucleotide in the genome of the human subject the nucleotide at the position corresponding to position 1668 of SEQ ID NO: 400, wherein the presence of at least one copy of a G at said position indicates that the human subject is at risk for said increased metabolism of the CYP2C8 substrate relative to metabolism of the CYP2C8 substrate of a human subject whose genome has two copies of a T at said position.

2. The method of claim 1 further comprising the step of detecting the presence of a polypeptide encoded by the CYP2C8 polynucleotide of the human subject.

3. The method of claim 1, wherein the detecting is performed using at least one of PCR, ligase chain reaction, restriction digestion, direct sequencing, nucleic acid amplification techniques, hybridization techniques and immunoassays.

4. The method according to claim 1, wherein the CYP2C8 substrate is paclitaxel.

* * * * *

UNITED STATES PATENT AND TRADEMARK OFFICE

CERTIFICATE OF CORRECTION

PATENT NO. : 7,871,767 B2
APPLICATION NO. : 10/479225
DATED : January 18, 2011
INVENTOR(S) : Penger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 628 days.

Signed and Sealed this
Twenty-sixth Day of July, 2011

David J. Kappos
*Director of the United States Patent and Trademark Office*